US008138140B2

(12) United States Patent
Stupp et al.

(10) Patent No.: US 8,138,140 B2
(45) Date of Patent: Mar. 20, 2012

(54) SELF-ASSEMBLING PEPTIDE AMPHIPHILES AND RELATED METHODS FOR GROWTH FACTOR DELIVERY

(75) Inventors: Samuel I. Stupp, Chicago, IL (US); Jack J. J. M. Donners, Chicago, IL (US); Gabriel A. Silva, Chicago, IL (US); Heather A. Behanna, Chicago, IL (US); Shawn G. Anthony, New Stanton, PA (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 12/466,691

(22) Filed: May 15, 2009

(65) Prior Publication Data

US 2009/0269847 A1 Oct. 29, 2009

Related U.S. Application Data

(62) Division of application No. 11/005,552, filed on Dec. 6, 2004, now Pat. No. 7,544,661.

(60) Provisional application No. 60/527,504, filed on Dec. 5, 2003.

(51) Int. Cl.
*A61K 38/00* (2006.01)
*A61K 38/04* (2006.01)
*C07K 5/00* (2006.01)
*C07K 7/00* (2006.01)
*C07K 16/00* (2006.01)

(52) U.S. Cl. .......... 514/1.1; 530/328; 530/329; 530/330

(58) Field of Classification Search ........................ None
See application file for complete search history.

(56) References Cited

U.S. PATENT DOCUMENTS

| | | | |
|---|---|---|---|
| 4,554,101 A | 11/1985 | Hopp | |
| 4,930,077 A | 5/1990 | Fan | |
| 5,114,713 A | 5/1992 | Sinigaglia | |
| 5,130,123 A | 7/1992 | Reynolds et al. | |
| 5,208,111 A | 5/1993 | Decher et al. | |
| 5,223,409 A | 6/1993 | Ladner et al. | |
| 5,622,699 A | 4/1997 | Ruoslahti et al. | |
| 5,670,483 A | 9/1997 | Zhang et al. | |
| 5,733,868 A | 3/1998 | Peterson et al. | |
| 5,843,780 A | 12/1998 | Thomson | |
| 5,853,830 A | 12/1998 | McCaulley et al. | |
| 5,871,767 A | 2/1999 | Dionne et al. | |
| 5,955,343 A | 9/1999 | Holmes et al. | |
| 5,993,541 A | 11/1999 | Litvin et al. | |
| 6,051,272 A | 4/2000 | Stupp et al. | |
| 6,085,206 A | 7/2000 | Domini et al. | |
| 6,096,863 A | 8/2000 | Fields et al. | |
| 6,114,038 A | 9/2000 | Castro et al. | |
| 6,156,321 A | 12/2000 | Thorpe et al. | |
| 6,181,909 B1 | 1/2001 | Burstein et al. | |
| 6,201,065 B1 | 3/2001 | Pathak et al. | |
| 6,207,218 B1 | 3/2001 | Layrolle et al. | |
| 6,265,539 B1 | 7/2001 | Arlinghaus | |
| 6,269,368 B1 | 7/2001 | Diamond | |
| 6,270,765 B1 | 8/2001 | Deo et al. | |
| 6,309,862 B1 | 10/2001 | Jarekrans et al. | |
| 6,391,297 B1 | 5/2002 | Halvorsen | |
| 6,444,723 B1 | 9/2002 | Kline | |
| 6,458,924 B2 | 10/2002 | Knudsen et al. | |
| 6,473,730 B1 | 10/2002 | McKeown et al. | |
| 6,548,048 B1 | 4/2003 | Cuthbertson et al. | |
| 6,548,630 B1 | 4/2003 | Zhang et al. | |
| 6,562,619 B1 | 5/2003 | Gearhart et al. | |
| 6,800,481 B1 | 10/2004 | Holmes et al. | |
| 6,855,329 B1 | 2/2005 | Shakesheff et al. | |
| 6,890,654 B2 | 5/2005 | Stupp et al. | |
| 7,371,719 B2 | 5/2008 | Stupp et al. | |
| 7,390,526 B2 | 6/2008 | Stupp et al. | |
| 7,452,679 B2 | 11/2008 | Stupp et al. | |
| 7,491,690 B2 | 2/2009 | Stupp et al. | |
| 7,534,761 B1 | 5/2009 | Stupp et al. | |
| 7,544,661 B2 | 6/2009 | Stupp et al. | |
| 7,554,021 B2 | 6/2009 | Stupp et al. | |
| 7,683,025 B2 | 3/2010 | Stupp et al. | |
| 7,745,708 B2 | 6/2010 | Stupp et al. | |
| 2002/0007217 A1 | 1/2002 | Jacob et al. | |
| 2002/0046018 A1 | 4/2002 | Marcu et al. | |
| 2002/0142277 A1 | 10/2002 | Burstein et al. | |
| 2002/0160471 A1 | 10/2002 | Kisiday et al. | |
| 2003/0050231 A1* | 3/2003 | Rosen et al. | 514/12 |
| 2003/0059906 A1 | 3/2003 | Hubbell et al. | |
| 2003/0092672 A1 | 5/2003 | Darcy et al. | |
| 2003/0176335 A1 | 9/2003 | Zhang et al. | |
| 2003/0187232 A1 | 10/2003 | Hubbell et al. | |
| 2004/0001893 A1 | 1/2004 | Stupp et al. | |

(Continued)

FOREIGN PATENT DOCUMENTS

CN 2007-483492 2/2007

(Continued)

OTHER PUBLICATIONS

Hui, Michael. May 24, 2004. "Heparin Binding Peptide Amphiphile and Transforming Growth Factor: A Novel Approach to Anti-Angiogenic Drug Delivery." The Second Annual Undergraduate Research Symposium. Retrieved from http://www.northwestern.edu/provost/students/research_symposium/program2004.pdf on Oct. 14, 2009. 45 pages.

Wayback Machine. http://www.archive.org/web/ entry, 1 page for http://www.northwestern.edu/provost/students/research_symposium/program2004.pdf retrieved on Oct. 14, 2009.

Clemetson, K. J., and J. M. Clemetson. 1998. "Integrins and Cardiovascular Disease." CMLS Cellular and Molecular Life Sciences. vol. 54, pp. 502-513.

Dupin, Elisabeth, and Nicole M. Le Douarin. 2003. "Development of Melanocyte Precursors from the Vertebrate Neural Crest." Oncogene. vol. 22, pp. 3016-3023.

Mardilovich, Anastasia, and Efrosini Kokkoli. 2004. "Biomimetic Peptide—Amphiphiles for Functional Biomaterials: The Role of GRGDSP and PHSRN." Biomacromolecules. vol. 5, No. 3, pp. 950-957.

(Continued)

*Primary Examiner* — Marcela M Cordero Garcia

(57) ABSTRACT

Amphiphilic peptide compounds comprising one or more epitope sequences for binding interaction with one or more corresponding growth factors, micellar assemblies of such compounds and related methods of use.

14 Claims, 1 Drawing Sheet

U.S. PATENT DOCUMENTS

| | | | |
|---|---|---|---|
| 2004/0018961 A1 | 1/2004 | Stupp et al. | |
| 2004/0022718 A1 | 2/2004 | Stupp et al. | |
| 2004/0068266 A1 | 4/2004 | Delmotte | |
| 2004/0214272 A1 | 10/2004 | La Rosa et al. | |
| 2004/0258726 A1 | 12/2004 | Stupp et al. | |
| 2005/0208589 A1 | 9/2005 | Stupp et al. | |
| 2005/0209145 A1 | 9/2005 | Stupp et al. | |
| 2005/0214257 A1 | 9/2005 | Zhao et al. | |
| 2005/0272662 A1 | 12/2005 | Stupp et al. | |
| 2006/0008544 A1 | 1/2006 | Myhill et al. | |
| 2006/0123505 A1 | 6/2006 | Kikuchi et al. | |
| 2006/0149036 A1 | 7/2006 | Stupp et al. | |
| 2006/0188555 A1 | 8/2006 | Cormier et al. | |
| 2006/0247165 A1 | 11/2006 | Stupp et al. | |
| 2007/0277250 A1 | 11/2007 | Stupp et al. | |
| 2008/0175883 A1* | 7/2008 | Hsu et al. | 424/423 |
| 2008/0248569 A1* | 10/2008 | Mata et al. | 435/375 |
| 2008/0299657 A1* | 12/2008 | Stupp et al. | 435/398 |
| 2009/0042804 A1 | 2/2009 | Hulvat et al. | |
| 2009/0098652 A1* | 4/2009 | Stupp et al. | 435/455 |
| 2009/0269847 A1 | 10/2009 | Stupp et al. | |
| 2010/0221224 A1 | 9/2010 | Stupp et al. | |
| 2011/0008890 A1 | 1/2011 | Stupp et al. | |

FOREIGN PATENT DOCUMENTS

| | | |
|---|---|---|
| CN | 1915438 | 2/2007 |
| JP | 403099096 A | 4/1991 |
| WO | WO 93/22343 | 11/1993 |
| WO | WO 94/02506 | 2/1994 |
| WO | 96/02260 A1 | 2/1996 |
| WO | WO 97/14713 A1 | 4/1997 |
| WO | WO 97/20639 A1 | 6/1997 |
| WO | WO 98/07752 A1 | 2/1998 |
| WO | 98/43686 A1 | 10/1998 |
| WO | WO 99/36107 A1 | 7/1999 |
| WO | WO 99/55383 A2 | 11/1999 |
| WO | WO 00/13710 A2 | 3/2000 |
| WO | WO 00/44808 A1 | 8/2000 |
| WO | WO 00/45831 A1 | 8/2000 |
| WO | WO 00/52145 A2 | 9/2000 |
| WO | WO 00/64481 A1 | 11/2000 |
| WO | WO 01/00650 A1 | 1/2001 |
| WO | 01/48148 A1 | 7/2001 |
| WO | 01/56628 A1 | 8/2001 |
| WO | WO 0155302 * | 8/2001 |
| WO | 02/20822 A2 | 3/2002 |
| WO | 02/39118 A1 | 5/2002 |
| WO | WO 02/062969 A2 | 8/2002 |
| WO | WO 03/040336 A2 | 5/2003 |
| WO | WO 03/054146 A2 | 7/2003 |
| WO | WO 03/070749 A2 | 8/2003 |
| WO | WO 03/084980 A2 | 10/2003 |
| WO | WO 03/090255 A2 | 10/2003 |
| WO | WO 2004/003561 A1 | 1/2004 |
| WO | WO 2004/018628 A2 | 3/2004 |
| WO | WO 2004/024778 A2 | 3/2004 |
| WO | WO 2004/046167 A2 | 6/2004 |
| WO | WO 2004/072104 A2 | 8/2004 |
| WO | WO 2004/091370 A2 | 10/2004 |
| WO | WO 2004/106359 A2 | 12/2004 |
| WO | WO 2005/003292 A2 | 1/2005 |
| WO | WO 2005/014619 A2 | 2/2005 |
| WO | WO 2005/056039 A1 | 6/2005 |
| WO | WO 2005/056576 A2 | 6/2005 |
| WO | 2006/079036 A2 | 7/2006 |
| WO | WO 2006/096614 A2 | 9/2006 |
| WO | 2008/131052 A2 | 10/2008 |

OTHER PUBLICATIONS

Cui, Honggang, Takahiro Muraoka, Andrew G. Cheetham, and Samuel I. Stupp. 2009. "Self-Assembly of Giant Peptide Nanobelts." Nano Letters. vol. 9, No. 3, pp. 945-951.

Niece, Krista L., Catherine Czeisler, Vibhu Sahni, Vicki Tysseling-Mattiace, Eugene T. Pashuck, John A. Kessler, and Samuel I. Stupp. 2008. "Modification of Gelation Kinetics in Bioactive Peptide Amphiphiles." Biomaterials. vol. 29, pp. 4501-4509.

Copping, Aaron M. and Vanda R. G. Pond. Dec. 9, 1950. "Folic Acid as a Growth-Factor for the Rat." Nature. No. 4232, p. 993.

Brown, Walter E. Dec. 15, 1962. "Octacalcium Phosphate and Hydroxyapatite." Nature. vol. 196, pp. 1048-1050.

Liang, W. Y. and A. D. Yoffe. Jan. 8, 1968. "Transmission Spectra of ZnO Single Crystals." Physical Review Letters. vol. 20, No. 2, pp. 59-62.

Greenfield, Norma and Gerald D. Fasman. Oct. 1969. "Computed Circular Dichroism Spectra for the Evaluation of Protein Conformation." Biochemistry. vol. 8, No. 10, pp. 4108-4116.

Hantke, Klaus and Volkmar Braun. 1973. "Covalent Binding of Lipid to Protein: Diglyceride and Amide-Linked Fatty Acid at the N-Terminal End of the Murein-Lipoprotein of the *Escherichia coli* Outer Membrane." Eur. J. Biochem. vol. 34, No. 2, pp. 284-296.

Balcerski, James S., E. S. Pysh, G. M. Bonora, and C. Toniolo. Jun. 9, 1976. "Vacuum Ultraviolet Circular Dichroism of β-Forming Alkyl Oligopeptides." Journal of the American Chemical Society. vol. 98, No. 12, pp. 3470-3473.

Jacobson, Bruce S. and Daniel Branton. Jan. 21, 1977. "Plasma Membrane: Rapid Isolation and Exposure of the Cytoplasmic Surface by Use of Positively Charged Beads." Science. vol. 195, No. 4275, pp. 302-304.

Biesecker, G., J. Ieuan Harris, J. C. Thierry, J. E. Walker, and A. J. Wonacott. Mar. 24, 1977. Nature. vol. 266, pp. 328-333.

Kelly, Margaret M., E. S. Pysh, G. M. Bonora, and C. Toniolo. May 11, 1977. "Vacuum Ultraviolet Circular Dichroism of Protected Homooligomers Derived from L-Leucine." Journal of the American Chemical Society. vol. 99, No. 10, pp. 3264-3266.

Blumenthal, N. C., A. S. Posner, L. D. Silverman, and L. C. Rosenberg. 1979. "Effect of Proteoglycans on in Vitro Hydroxyapatite Formation." Calcified Tissue International. vol. 27, No. 1, pp. 75-82.

Richardson, P. M., U. M. McGuinness, and A. J. Aguayo. Mar. 20, 1980. "Axons from CNS Neurones Regenerate into PNS Grafts." Nature. vol. 284, pp. 264-265.

Lim, Franklin and Anthony M. Sun. Nov. 21, 1980. "Microencapsulated Islets as Bioartificial Endocrine Pancreas." Science. vol. 210, No. 4472, pp. 908-910.

Jain, Rakesh K., Chhitar M. Gupta, and Nitya Anand. 1981. "Synthesis of Peptidylglycophospholipids, Novel Derivatives of Muramyl-Dipeptide." Tetrahedron Letters. vol. 22, No. 24, pp. 2317-2320.

Sarin, Virender K., Stephen B. H. Kent, James P. Tam, and R. B. Merrifield. 1981. "Quantitative Monitoring of Solid-Phase Peptide Synthesis by the Ninhydrin Reaction." Analytical Biochemistry. vol. 117, pp. 147-157.

Yannas, I. V., J. F. Burke, D. P. Orgill, E. M. Skrabut. Jan. 8, 1982. "Wound Tissue Can Utilize a Polymeric Template to Synthesize a Functional Extension of Skin." Science. vol. 215, No. 4529, pp. 174-176.

Montesano, R., L. Orci, and P. Vassalli. Nov. 1983. "In Vitro Rapid Organization of Endothelial Cells into Capillary-like Networks is Promoted by Collagen Matrices." The Journal of Cell Biology. vol. 97, pp. 1648-1652.

Pierschbacher, Michael D. and Erkki Ruoslahti. May 3, 1984. "Cell Attachment Activity of Fibronectin Can be Duplicated by Small Synthetic Fragments of the Molecule." Nature. vol. 309, pp. 30-33.

Landis, W. J. and J. R. Martin. Apr.-Jun. 1984. "X-Ray Photoelectron Spectroscopy Applied to Gold-Decorated Mineral Standards of Biological Interest." J. Vac. Sci. Technol. vol. A 2, No. 2, pp. 1108-1111.

Thompson, Nancy L., Adrienne A. Brian, and Harden M. McConnell. 1984. "Covalent Linkage of a Synthetic Peptide to a Fluorescent Phospholipid and its Incorporation into Supported Phospholipid Monolayers." Biochimica et Biophysica Acta. vol. 772, pp. 10-19.

Yamada, Kimiho, Hirotaka Ihara, Toshio Ide, Takanori Fukumoto, and Chuichi Hirayama. 1984. "Formation of Helical Super Structure from Single-Walled Bilayers by Amphiphiles with Oligo-L-Glutamic Acid-Head Group." Chemistry Letters. No. 10, pp. 1713-1716.

Addadi, L. and S. Weiner. Jun. 15, 1985. "Interactions Between Acidic Proteins and Crystals: Stereochemical Requirements in Biomineralization." Proceedings of the National Academy of Sciences of the United States of America. vol. 82, No. 12, pp. 4110-4114.

"Public Health Service Policy on Humane Care and Use of Laboratory Animals." Sep. 1986. Office for Protection from Research Risks (OPRR), National Institutes of Health.

Weiner, Stephen and Wolfie Traub. Oct. 1986. "Organization of Hydroxyapatite Crystals Within Collagen Fibrils." *FEBS Letters*. vol. 206, No. 2, pp. 262-266.

Mann, Stephen, John P. Hannington, and R. J. P. Williams. Dec. 11, 1986. "Phospholipid Vesicles as a Model System for Biomineralization." *Nature*. vol. 324, pp. 565-567.

Krimm, Samuel and Jagdeesh Bandekar. 1986. "Vibrational Spectroscopy and Conformation of Peptides, Polypeptides, and Proteins." *Advances in Protein Chemistry*. vol. 38, pp. 181-364.

de Groot, K., R. Geesink, C. P. A. T. Klein, and P. Serekian. Dec. 1987. "Plasma Sprayed Coatings of Hydroxylapatite." *Journal of Biomedical Materials Research*. vol. 21, No. 12, pp. 1375-1381.

Bresnahan, J. C., M. S. Beattie, F. D. Todd III, and D. H. Noyes. 1987. "A Behavioral and Anatomical Analysis of Spinal Cord Injury Produced by a Feedback-Controlled Impaction Device." *Experimental Neurology*. vol. 95, pp. 548-570.

Moscatelli, David. 1987. "High and Low Affinity Binding Sites for Basic Fibroblast Growth Factor on Cultured Cells: Absence of a Role for Low Affinity Binding in the Stimulation of Plasminogen Activator Production by Bovine Capillary Endothelial Cells." *Journal of Cellular Physiology*. vol. 131, pp. 123-130.

Lambert, Joseph B., Herbert F. Shurvell, David A. Lightner, and R. Graham Cooks. 1987. "Group Frequencies: Infrared and Raman." *Introduction to Organic Spectroscopy*. New York: Macmillan Publishing Company. pp. 169-182.

Cook, Stephen D., Kevin A. Thomas, John F. Kay, and Michael Jarcho. Jul. 1988. "Hydroxyapatite-Coated Titanium for Orthopedic Implant Applications." *Clinical Orthopaedics and Related Research*. No. 232, pp. 225-243.

Saksela, Olli, David Moscatelli, Andreas Sommer, and Daniel B. Rifkin. Aug. 1988. "Endothelial Cell-Derived Heparan Sulfate Binds Basic Fibroblast Growth Factor and Protects it from Proteolytic Degradation." *The Journal of Cell Biology*. vol. 107, pp. 743-751.

Cardin, Alan D. and H. J. R. Weintraub. Jan./Feb. 1989. "Molecular Modeling of Protein-Glycosaminoglycan Interactions." *Arteriosclerosis*. vol. 9, No. 1, pp. 21-32.

Oonishi, H., M. Yamamoto, H. Ishimaru, E. Tsuji, S. Kuskitani, M. Aono, and Y. Ukon. Mar. 1989. "The Effect of Hydroxyapatite Coating on Bone Growth into Porous Titanium Alloy Implants." *The Journal of Bone and Joint Surgery*. vol. 71-B, No. 2, pp. 213-216.

Friedmann, Theodore. Jun. 16, 1989. "Progress Toward Human Gene Therapy." *Science*. vol. 244, No. 4910, pp. 1275-1281.

Traub, Wolfie, Talmon Arad, and Stephen Weiner. Dec. 15, 1989. "Three-Dimensional Ordered Distribution of Crystals in Turkey Tendon Collagen Fibers." *Proceedings of the National Academy of Sciences of the United States of America*. vol. 86, No. 24, pp. 9822-9826.

Knorr, Reinhard, Arnold Trzeciak, Willi Bannwarth, and Dieter Gillessen. 1989. "New Coupling Reagents in Peptide Chemistry." *Tetrahedron Letters*. vol. 30, No. 15, pp. 1927-1930.

Sambrook, Joseph, Edward F. Fritsch, and Thomas Maniatis. 1989. "Genes Encoding Selectable Markers." *Molecular Cloning: A Laboratory Manual*. 2nd ed. New York: Cold Spring Harbor Laboratory Press. pp. 16.9-16.15.

Veis, A. 1989. "Biochemical Studies of Vertebrate Tooth Mineralization." *Biomineralization*. S. Mann, J. Webb, and R. J. P. Williams, editors. Weinheim, Federal Republic of Germany: VCH Verlagsgesellschaft and New York: VCH Publishers. pp. 189-222.

Schnell, Lisa and Martin E. Schwab. Jan. 18, 1990. "Axonal Regeneration in the Rat Spinal Cord Produced by an Antibody Against Myelin-Associated Neurite Growth Inhibitors." *Nature*. vol. 343, pp. 269-272.

Ahn, Sang Tae and Thomas A. Mustoe. Jan. 1990. "Effects of Ischemia on Ulcer Wound Healing: A New Model in the Rabbit Ear." *Annals of Plastic Surgery*. vol. 24, No. 1, pp. 17-23.

Van de Pol, Frans C. M. Dec. 1990. "Thin-Film ZnO—Properties and Applications." *Ceramic Bulletin*. vol. 69, No. 12, pp. 1959-1965.

Addadi, L., A. Berman, J. Moradian-Oldak, and S. Weiner. Dec. 28, 1990. "Tuning of Crystal Nucleation and Growth by Proteins: Molecular Interactions at Solid-Liquid Interfaces in Biomineralization." *Croatica Chemica Acta*. vol. 63, No. 3, pp. 539-544.

Sukenik, Chaim N., Natarajan Balachander, Lloyd A. Culp, Kristine Lewandowska, and Katherine Merritt. 1990. "Modulation of Cell Adhesion by Modification of Titanium Surfaces with Covalently Attached Self-Assembled Monolayers." *Journal of Biomedical Materials Research*. vol. 24, pp. 1307-1323.

Fields, C. G., D. H. Lloyd, R. L. Macdonald, K. M. Otteson, and R. L. Noble. Mar./Apr. 1991. "HBTU Activation for Automated Fmoc Solid-Phase Peptide Synthesis." *Peptide Research*. vol. 4, No. 2, pp. 95-101.

Murata, Masayuki, Satoshi Kagiwada, Sho Takahashi, and Shun-ichi Ohnishi. Aug. 5, 1991. "Membrane Fusion Induced by Mutual Interaction of the Two Charge-Reversed Amphiphilic Peptides at Neutral pH." *The Journal of Biological Chemistry*. vol. 56, No. 22, pp. 14353-14358.

Harris, Robin, Editor. 1991. *Electron Microscopy in Biology: A Practical Approach*. New York: Oxford University Press.

Jackson, David Y., David S. King, Jean Chmielewski, Sunil Singh, and Peter G. Schultz. 1991. "General Approach to the Synthesis of Short α-Helical Peptides." *Journal of the American Chemical Society*. vol. 113, pp. 9391-9392.

Polverini, Peter J., Noel P. Bouck, and Farzan Rastinejad. 1991. "Assay and Purification of Naturally Occurring Inhibitor of Angiogenesis." *Methods in Enzymology*. vol. 198, pp. 440-450.

Weiner, Stephen and Wolfie Traub. Feb. 1992. "Bone Structure: From Ångstroms to Microns." *The FASEB Journal*. vol. 6, pp. 879-885.

Nomizu, Motoyoshi, Atsushi Utani, Norio Shiraishi, Maura C. Kibbey, Yoshihiko Yamada, and Peter P. Roller. Jul. 15, 1992. "The All-D-Configuration Segment Containing the IKVAV Sequence of Laminin A Chain Has Similar Activities to the All-L-Peptide in Vitro and in Vivo." *The Journal of Biological Chemistry*. vol. 267, No. 20, pp. 14118-14121.

Addadi, Lia and Stephen Weiner. 1992. "Control and Design Principles in Biological Mineralization." *Angew. Chem. Int. Ed. Engl.* vol. 31, pp. 153-169.

Beresford, J. N., J. H. Bennett, C. Devlin, P. S. Leboy, and M. E. Owen. 1992. "Evidence for an Inverse Relationship Between the Differentiation of Adipocytic and Osteogenic Cells in Rat Marrow Stromal Cell Cultures." *Journal of Cell Science*. vol. 102, pp. 341-351.

Cook, Stephen D., Kevin A. Thomas, Jeanette E. Dalton, Todd K. Volkman, Thomas S. Whitecloud III, and John F. Kay. 1992. "Hydroxylapatite Coating of Porous Implants Improves Bone Ingrowth and Interface Attachment Strength." *Journal of Biomedical Materials Research*. vol. 26, pp. 989-1001.

Geahlen, Robert L., G. Marc Loudon, Lisa A. Paige, and David Lloyd. 1992. "A General Method for Preparation of Peptides Biotinylated at the Carboxy Terminus." *Analytical Biochemistry*. vol. 202, pp. 68-70.

Ghadiri, M. Reza, Christopher Soares, and Chong Choi. 1992. "Design of an Artificial Four-Helix Bundle Metalloprotein via a Novel Ruthenium(II)-Assisted Self-Assembly Process." *Journal of the American Chemical Society*. vol. 114, No. 10, pp. 4000-4002.

Kunitake, Toyoki. 1992. "Synthetic Bilayer Membranes: Molecular Design, Self-Organization, and Application." *Angew. Chem. Int. Ed. Engl.* vol. 31, pp. 709-726.

Stupp, Samuel I. and Glenn W. Ciegler. 1992. "Organoapatites: Materials for Artificial Bone. I. Synthesis and Microstructure." *Journal of Biomedical Materials Research*. vol. 26, pp. 169-183.

Surewicz, Witold K., Henry H. Mantsch, and Dennis Chapman. Jan. 19, 1993. "Determination of Protein Secondary Structure by Fourier Transform Infrared Spectroscopy: A Critical Assessment." *Biochemistry*. vol. 32, No. 2, pp. 389-394.

Zhang, Shuguang, Todd Holmes, Curtis Lockshin, and Alexander Rich. Apr. 15, 1993. "Spontaneous Assembly of a Self-Complementary Oligopeptide to Form a Stable Macroscopic Membrane." *Proceedings of the National Academy of Sciences of the United States of America*. vol. 90, No. 8, pp. 3334-3338.

Langer, Robert and Joseph P. Vacanti. May 14, 1993. "Tissue Engineering." *Science*. vol. 260, No. 5110, pp. 920-926.

Mulligan, Richard C. May 14, 1993. "The Basic Science of Gene Therapy." *Science*. vol. 260, No. 5110, pp. 926-932.

Massas, R., S. Pitaru, and M. M. Weinreb. Jun. 1993. "The Effects of Titanium and Hydroxyapatite on Osteoblastic Expression and Proliferation in Rat Parietal Bone Cultures." *Journal of Dental Research*. vol. 72, No. 6, pp. 1005-1008.

Archibald, Douglas D. and Stephen Mann. Jul. 29, 1993. "Template Mineralization of Self-Assembled Anisotropic Lipid Microstructures." *Nature*. vol. 364, pp. 430-433.

Atala, Anthony, Linda G. Cima, Wooseob Kim, Keith T. Paige, Joseph P. Vacanti, Alan B. Retik, and Charles A. Vacanti. Aug. 1993. "Injectable Alginate Seeded with Chondrocytes as a Potential Treatment for Vesicoureteral Reflux." *The Journal of Urology*. vol. 150, No. 2, pp. 745-747.

Nomizu, Motoyoshi, Keizo Yamamura, Hynda K. Kleinman, and Yoshihiko Yamada. Aug. 1, 1993. "Multimeric Forms of Tyr-Ile-Gly-Ser-Arg (YIGSR) Peptide Enhance the Inhibition of Tumor Growth and Metastasis." *Cancer Research*. vol. 53, pp. 3459-3461.

Ross-Murphy, S. B. and K. P. Shatwell. May-Aug. 1993. "Polysaccharide Strong and Weak Gels." *Biorheology*. vol. 30, Nos. 3 & 4, pp. 217-227.

Margalit, Hanah, Nurit Fischer, and Shmuel A. Ben-Sasson. Sep. 15, 1993. "Comparative Analysis of Structurally Defined Heparin Binding Sequences Reveals a Distinct Spatial Distribution of Basic Residues." *The Journal of Biological Chemistry*. vol. 268, No. 26, pp. 19228-19231.

Kibbey, Maura C., Mathias Jucker, Benjamin S. Weeks, Rachael L. Neve, Wiliam E. Van Nostrand, and Hynda K. Kleinman. Nov. 1993. "β-Amyloid Precursor Protein Binds to the Neurite-Promoting IKVAV Site of Laminin." *Proc. Natl. Acad. Sci. U.S.A.* vol. 90, pp. 10150-10153.

Fowler, Bruce O., Milenko Marković, and Walter E. Brown. 1993. "Octacalcium Phosphate. 3. Infrared and Raman Vibrational Spectra." *Chem. Mater*. vol. 5, No. 10, pp. 1417-1423.

Fuhrhop, Jürgen-Hinrich, Dragan Spiroski, and Christoph Boettcher. 1993. "Molecular Monolayer Rods and Tubules Made of α-(L-Lysine),ω-(Amino) Bolaamphiphiles." *Journal of the American Chemical Society*. vol. 115, No. 4, pp. 1600-1601.

Graham, Stephan and Paul W. Brown. 1993. "The Low Temperature Formation of Octacalcium Phosphate." *Journal of Crystal Growth*. vol. 132, pp. 215-225.

Shimizu, Toshimi and Masakatsu Hato. 1993. "Self-Assembling Properties of Synthetic Peptidic Lipids." *Biochimica et Biophysica Acta*. vol. 1147, pp. 50-58.

Stupp, Samuel I., Jacqueline A. Hanson, Jo Ann Eurell, Glenn W. Ciegler, and Ann Johnson. 1993. "Organoapatites: Materials for Artifical Bone. III. Biological Testing." *Journal of Biomedical Materials Research*. vol. 27, pp. 301-311.

Stupp, Samuel I., George C. Mejicano, and Jacqueline A. Hanson. 1993. "Organoapatites: Materials for Artificial Bone. II. Hardening Reactions and Properties." *Journal of Biomedical Materials Research*. vol. 27, pp. 289-299.

Wald, Heidi L., Georgios Sarakinos, Michelle D. Lyman, Antonios G. Mikos, Joseph P. Vacanti, and Robert Langer. 1993. "Cell Seeding in Porous Transplantation Devices." *Biomaterials*. vol. 14, No. 4, pp. 270-278.

Walsh, Dominic, Joanne L. Kingston, Brigid R. Heywood, and Stephen Mann. 1993. "Influence of Monosaccharides and Related Molecules on the Morphology of Hydroxyapatite." *Journal of Crystal Growth*. vol. 133, pp. 1-12.

Wang, B. C., T. M. Lee, E. Chang, and C. Y. Yang. 1993. "The Shear Strength and the Failure Mode of Plasma-Sprayed Hydroxyapatite Coating to Bone: The Effect of Coating Thickness." *Journal of Biomedical Materials Research*. vol. 27, pp. 1315-1327.

San Antonio, James D., Arthur D. Lander, Morris J. Karnovsky, and Henry S. Slayter. Jun. 1994. "Mapping the Heparin-Binding Sites on Type I Collagen Monomers and Fibrils." *The Journal of Cell Biology*. vol. 125, No. 5, pp. 1179-1188.

Ban, S., S. Maruno, H. Iwata, and H. Itoh. 1994. "Calcium Phosphate Precipitation on the Surface of HA-G-Ti Composite Under Physiologic Conditions." *Journal of Biomedical Materials Research*. vol. 28, pp. 65-71.

de Bruijn, J. D., Y. P. Bovell, and C. A. van Blitterswijk. 1994. "Structural Arrangements at the Interface Between Plasma Sprayed Calcium Phosphates and Bone." *Biomaterials*. vol. 15, No. 7, pp. 543-550.

Hunter, Graeme K. and Harvey A. Goldberg. 1994. "Modulation of Crystal Formation by Bone Phosphoproteins: Role of Glutamic Acid-Rich Sequences in the Nucleation of Hydroxyapatite by Bone Sialoprotein." *Biochem. J.* vol. 302, pp. 175-179.

Klein, C. P. A. T., J. G. C. Wolke, J. M. A. de Blieck-Hogervorst, and K. de Groot. 1994. "Calcium Phosphate Plasma-Sprayed Coatings and Their Stability: An in Vivo Study." *Journal of Biomedical Materials Research*. vol. 28, pp. 909-917.

Margomenou-Leonidopoulou, G. 1994. "Thermotropic Mesophases of Ionic Amphiphiles. II. Ionic Amphiphiles in Aqueous Media." *Journal of Thermal Analysis*. vol. 42, pp. 1041-1061.

Mikos, Antonios G., Michelle D. Lyman, Lisa E. Freed, and Robert Langer. 1994. "Wetting of Poly(L-Lactic Acid) and Poly(DL-Lactic-co-glycolic Acid) Foams for Tissue Culture." *Biomaterials*. vol. 15, No. 1, pp. 55-58.

Bond, G. M., R. H. Richman, and W. P. McNaughton. Jun. 1995. "Mimicry of Natural Material Designs and Processes." *Journal of Materials Engineering and Performance*. vol. 4, No. 3, pp. 334-345.

Hubbell, Jeffrey A. Jun. 1995. "Biomaterials in Tissue Engineering." *Bio/technology*. vol. 13, pp. 565-576.

Fromm, J. R., R. E. Hileman, E. E. O. Caldwell, J. M. Weiler, and R. J. Linhardt. Nov. 10, 1995. "Differences in the Interaction of Heparin with Arginine and Lysine and the Importance of these Basic Amino Acids in the Binding of Heparin to Acidic Fibroblast Growth Factor." *Archives of Biochemistry and Biophysics*. vol. 323, No. 2, pp. 279-287.

Wakitani, Shigeyuki, Tomoyuki Saito, and Arnold I. Caplan. Dec. 1995. "Myogenic Cells Derived from Rat Bone Marrow Mesenchymal Stem Cells Exposed to 5-Azacytidine." *Muscle & Nerve*. vol. 18, pp. 1417-1426.

Aletras, Alexios, Kleomenis Barlos, Dimitrios Gatos, Sophia Koutsogianni, and Petros Mamos. 1995. "Preparation of the Very Acid-Sensitive Fmoc-Lys(Mtt)-OH." *International Journal of Peptide & Protein Research*. vol. 45, pp. 488-496.

Berndt, Peter, Gregg B. Fields, and Matthew Tirrell. 1995. "Synthetic Lipidation of Peptides and Amino Acids: Monolayer Structure and Properties." *Journal of the American Chemical Society*. vol. 117, No. 37, pp. 9515-9522.

Gage, Fred H., Jasodhara Ray, and Lisa J. Fisher. 1995. "Isolation, Characterization, and Use of Stem Cells from the CNS." *Annual Review of Neuroscience*. vol. 18, pp. 159-192.

Jackowski, Andre. 1995. "Neural Injury Repair: Hope for the Future as Barriers to Effective CNS Regeneration Become Clearer." *J. Neurosurg*. vol. 9, pp. 303-317.

Nomizu, Motoyoshi, Benjamin S. Weeks, Christi A. Weston, Woo Hoo Kim, Hynda K. Kleinman, and Yoshihiko Yamada. 1995. "Structure-Activity Study of a Laminin α1 Chain Active Peptide Segment Ile-Lys-Val-Ala-Val (IKVAV)." *FEBS Letters*. vol. 365, pp. 227-231.

Saito, Tomoyuki, James E. Dennis, Donald P. Lennon, Randell G. Young, and Arnold I. Caplan. 1995. "Myogenic Expression of Mesenchymal Stem Cells Within Myotubes of *mdx* Mice in Vitro and in Vivo." *Tissue Engineering*. vol. 1, No. 4, pp. 327-343.

Sasanuma, Michio. 1995. "Optical Processes in ZnO." *J. Phys.: Condens. Matter*. vol. 7, pp. 10029-10036.

Zhang, Shuguang, Todd C. Holmes, C. Michael DiPersio, Richard O. Hynes, Xing Su, and Alexander Rich. 1995. "Self-Complementary Oligopeptide Matrices Support Mammalian Cell Attachment." *Biomaterials*. vol. 16, No. 18, pp. 1385-1393.

Falini, Guiseppe, Shira Albeck, Steve Weiner, and Lia Addadi. Jan. 5, 1996. "Control of Aragonite or Calcite Polymorphism by Mollusk Shell Macromolecules." *Science*. vol. 271, No. 5245, pp. 67-69.

Alivisatos, A. P. Feb. 16, 1996. "Semiconductor Clusters, Nanocrystals, and Quantum Dots." *Science*. vol. 271, No. 5251, pp. 933-937.

Keyt, Bruce A., Lea T. Berleau, Hung V. Nguyen, Helen Chen, Henry Heinsohn, Richard Vandlen, and Napoleone Ferrara. Mar. 29, 1996. "The Carboxyl-terminal Domain (111-165) of Vascular Endothelial Growth Factor is Critical for its Mitogenic Potency." *The Journal of Biological Chemistry*. vol. 271, No. 13, pp. 7788-7795.

Oka, Kazunari, Masaaki Yamamoto, Toshiharu Nonaka, and Masamichi Tomonaga. Apr. 1996. "The Significance of Artificial Cerebrospinal Fluid as Perfusate and Endoneurosurgery." *Neurosurgery Online*. vol. 38, No. 4, pp. 733-736.

Belcher, A. M., X. H. Wu, R. J. Christensen, P. K. Hansma, G. D. Stucky, and D. E. Morse. May 2, 1996. "Control of Crystal Phase Switching and Orientation by Soluble Mullusc-Shell Proteins." *Nature*. vol. 381, pp. 56-58.

Hortelano, Gonzalo, Ayman Al-Hendy, Frederick A. Ofosu, and Patricia L. Chang. Jun. 15, 1996. "Delivery of Human Factor IX in Mice by Encapsulated Recombinant Myoblasts: A Novel Approach Towards Allogenic Gene Therapy of Hemophilia B." *Blood*. vol. 87, No. 12, pp. 5095-5103.

Sultzbaugh, K. J. and T. J. Speaker. Jul.-Aug. 1996. "A Method to Attach Lectins to the Surface of Spermine Alginate Microcapsules Based on the Avidin Biotin Interaction." *J. Microencapsulation*. vol. 13, No. 4, pp. 363-375.

Alivisatos, A. Paul, Kai P. Johnsson, Xiaogang Peng, Troy E. Wilson, Colin J. Loweth, Marcel P. Burchez Jr., and Peter G. Schultz. Aug. 15, 1996. "Organization of 'Nanocrystal Molecules' Using DNA." *Nature*. vol. 382, pp. 609-611.

George, Anne, Leslie Bannon, Boris Sabsay, Jerry W. Dillon, James Malone, Arthur Veis, Nancy A. Jenkins, Debra J. Gilbert, and Neal G. Copeland. Dec. 20, 1996. "The Carboxyl-terminal Domain of Phosphophoryn Contains Unique Extended Triplet Amino Acid Repeat Sequences Forming Ordered Carboxyl-Phosphate Interaction Ridges That May be Essential in the Biomineralization Process." *The Journal of Biological Chemistry*. vol. 271, No. 51, pp. 32869-32873.

Basso, D. Michele, Michael S. Beattie, and Jacqueline C. Bresnahan. 1996. "Graded Histological and Locomotor Outcomes after Spinal Cord Contusion Using the NYU Weight-Drop Device Versus Transection." *Experimental Neurology*. vol. 139, pp. 244-256.

Burkett, Sandra L. and Stephen Mann. 1996. "Spatial Organization and Patterning of Gold Nanoparticles on Self-Assembled Biolipid Tubular Templates." *Chem. Commun*. pp. 321-322.

Hunter, Graeme K., Peter V. Hauschka, A. Robin Poole, Lawrence C. Rosenberg, and Harvey A. Goldberg. 1996. "Nucleation and Inhibition of Hydroxyapatite Formation by Mineralized Tissue Proteins." *Biochem. J*. vol. 317, pp. 59-64.

Karymov, Mikhail A., Karel Procházka, John M. Mendenhall, Thomas J. Martin, Petr Munk, and Stephen E. Webber. 1996. "Chemical Attachment of Polystyrene-*block*-poly(methacrylic acid) Micelles on a Silicon Nitride Surface." *Langmuir*. vol. 12, No. 20, 4748-4753.

Landis, William J., Karen J. Hodgens, James Arena, Min Ja Song, and Bruce F. McEwen. 1996. "Structural Relations Between Collagen and Mineral in Bone as Determined by High Voltage Electron Microscopic Tomography." *Microscopy Research and Technique*. vol. 33, pp. 192-202.

Matsuzawa, Mieko, Forrest F. Weight, Richard S. Potember, and Päivi Liesi. 1996. "Directional Neurite Outgrowth and Axonal Differentiation of Embryonic Hippocampal Neurons Are Promoted by a Neurite Outgrowth Domain of the B2-Chain of Laminin" *Int. J. Devl. Neuroscience*. vol. 14, No. 3, pp. 283-295.

Mooney, David J., Daniel F. Baldwin, Nam P. Suh, Joseph P. Vacanti, and Robert Langer. 1996. "Novel Approach to Fabricate Porous Sponges of Poly(D,L-Lactic-co-glycolic Acid) Without the Use of Organic Solvents." *Biomaterials*. vol. 17, No. 14, pp. 1417-1422.

Rappolt, Michael and Gert Rapp. 1996. "Structure of the Stable and Metastable Ripple Phase of Dipalmitoylphosphatidylcholine." *Eur. Biophys. J*. vol. 24, pp. 381-386.

Ratner, Buddy D., Allan S. Hoffman, Frederick J. Schoen, and Jack E. Lemons, Editors. 1996. *Biomaterials Science: An Introduction to Materials in Medicine*. San Diego, CA: Academic Press.

Tam, James P. 1996. "Recent Advances in Multiple Antigen Peptides." *Journal of Immunological Methods*. vol. 196, pp. 17-32.

Ulman, Abraham. 1996. "Formation and Structure of Self-Assembled Monolayers." *Chemical Reviews*. vol. 96, No. 4, pp. 1533-1554.

Yu, Ying-Ching, Peter Berndt, Matthew Tirrell, and Gregg B. Fields. 1996. "Self-Assembling Amphiphiles for Construction of Protein Molecular Architecture." *Journal of the American Chemical Society*. vol. 118, No. 50, pp. 12515-12520.

Zarif, Leila, Ange Polidori, Bernard Pucci, Tadek Gulik-Krzywicki, André A. Pavia, and Jean G. Riess. 1996. "Effect of Chirality on the Formation of Tubules from Glycolipidic Amphiphiles." *Chemistry and Physics of Lipids*. vol. 79, pp. 165-170.

Aggeli, A., M. Bell, N. Boden, J. N. Keen, P. F. Knowles, T. C. B. McLeish, M. Pitkeathly, and S. E. Radford. Mar. 20, 1997. "Responsive Gels Formed by the Spontaneous Self-Assembly of Peptides into Polymeric β-Sheet Tapes." *Nature*. vol. 386, pp. 259-262.

Herr, Andrew B., David M. Ornitz, Ram Sasisekharan, Ganesh Venkataraman, and Gabriel Waksman. Jun. 27, 1997. "Heparin-Induced Self-Association of Fibroblast Growth Factor-2." *The Journal of Biological Chemistry*. vol. 272, No. 26, pp. 16382-16389.

Dimmeler, Stefanie and Andreas M. Zeiher. Aug. 1997. "Nitric Oxide and Apoptosis: Another Paradigm for the Double-Edged Role of Nitric Oxide." *NITRIC OXIDE: Biology and Chemistry*. vol. 1, No. 4, pp. 275-281.

Stupp, Samuel I. and Paul V. Braun. Aug. 29, 1997. "Molecular Manipulation of Microstructures: Biomaterials, Ceramics, and Semiconductors." *Science*. vol. 277, No. 5330, pp. 1242-1248.

Kaufmann, P. M., S. Heimrath, B. S. Kim, and D. J. Mooney. Sep./Oct. 1997. "Highly Porous Polymer Matrices as a Three-Dimensional Culture System for Hepatocytes." *Cell Transplantation*. vol. 6, No. 5, pp. 463-468.

Aggeli, Amalia, Mark Bell, Neville Boden, Jeff N. Keen, Tom C. B. McLeish, Irina Nyrkova, Sheena E. Radford, and Alexander Semenov. 1997. "Engineering of Peptide β-Sheet Nanotapes." *J. Mater. Chem*. vol. 7, No. 7, pp. 1135-1145.

Anderson, James M. and Matthew S. Shive. 1997. "Biodegradation and Biocompatibility of PLA and PLGA Microspheres." *Advanced Drug Delivery Reviews*. vol. 28, pp. 5-24.

Draget, Kurt Ingar, Gudmund Skjåk-Bræk, Olav Smidsrød. 1997. "Alginate Based New Materials." *International Journal of Biological Macromolecules*. vol. 21, pp. 47-55.

El-Ghannam, Ahmed, Paul Ducheyne, and Irving M. Shapiro. 1997. "Porous Bioactive Glass and Hydroxyapatite Ceramic Affect Bone Cell Function In Vitro Along Different Time Lines." *Journal of Biomedical Materials Research*. vol. 36, pp. 167-180.

Goveas, J. L. and S. T. Milner. 1997. "Dynamics of the Lamellar—Cylindrical Transition in Weakly Segregated Diblock Copolymer Melts." Macromolecules. vol. 30, No. 9, pp. 2605-2612.

Jaiswal, Neelam, Stephen E. Haynesworth, Arnold I. Caplan, and Scott P. Bruder. 1997. "Osteogenic Differentiation of Purified, Culture-Expanded Human Mesenchymal Stem Cells In Vitro." *Journal of Cellular Biochemistry*. vol. 64, pp. 295-312.

Munson, John B. and Stephen B. McMahon. 1997. "Effects of GDNF on Axotomized Sensory and Motor Neurons in Adult Rats." European Journal of Neuroscience. vol. 9, pp. 1126-1129.

Nehrer, Stefan, Howard A. Breinan, Arun Ramappa, Sonya Shortkroff, Gretchen Young, Tom Minas, Clement B. Sledge, Ioannis V. Yannas, and Myron Spector. 1997. "Canine Chondrocytes Seeded in Type I and Type II Collagen Implants Investigated In Vitro." *Journal of Biomedical Materials Research (Appl. Biomater.)*. vol. 38, pp. 95-104.

Mann, Stephen. 1997. "Biomineralization: The Form(id)able Part of Bioinorganic Chemistry!" *J. Chem. Soc., Dalton Trans*. pp. 3953-3961.

Norrby, Klas. 1997. "Angiogenesis: New Aspects Relating to its Initiation and Control." *APMIS*. vol. 105, pp. 417-437.

Shimizu, Toshimi, Masaki Kogiso, and Mitsutoshi Masuda. 1997. "Noncovalent Formation of Polyglycine II-Type Structure by Hexagonal Self-Assembly of Linear Polymolecular Chains." *Journal of the Americal Chemical Society*. vol. 119, No. 26, pp. 6209-6210, S2-S17.

Smith, George P. and Valery A. Petrenko. 1997. "Phage Display." *Chemical Reviews*. vol. 97, No. 2, pp. 391-410.

Toyotama, Akiko, Shin-ichi Kugimiya, Masakatsu Yonese, Takatoshi Kinoshita, and Yoshiharu Tsujita. 1997. "Controllable Orientation of the Peptide-Based Surfactant at Air-Water Interface." *Chemistry Letters*. pp. 443-444.

Weiner, Stephen and Lia Addadi. 1997. "Design Strategies in Mineralized Biological Materials." *J. Mater. Chem*. vol. 7, No. 5, pp. 689-702.

Wellings, Donald A. and Eric Atherton. 1997. "Standard Fmoc Protocols." *Methods in Enzymology*. vol. 289, pp. 44-67.

Wen, H. B., J. G. C. Wolke, J. R. de Wijn, Q. Liu, F. Z. Cui, and K. de Groot. 1997. "Fast Precipitation of Calcium Phosphate Layers on Titanium Induced by Simple Chemical Treatments." *Biomaterials*. vol. 18, No. 22, pp. 1471-1478.

Yu, Ying-Ching, Teika Pakalns, Yoav Dori, James B. McCarthy, Matthew Tirrell, and Gregg B. Fields. 1997. "Construction of Biologically Active Protein Molecular Architecture Using Self-Assembling Peptide-Amphiphiles." *Methods in Enzymology*. vol. 289, pp. 571-587.

Zhitomirsky, I. and L. Gal-Or. 1997. "Electrophoretic Deposition of Hydroxyapatite." *Journal of Materials Science: Materials in Medicine*. pp. 213-219.

Veis, Arthur, Kuiru Wei, Charles Sfeir, Anne George, and James Malone. Jan. 1998. "Properties of the $(DSS)_n$ Triplet Repeat Domain of Rat Dentin Phosphophoryn." *European Journal of Oral Sciences*. vol. 106 (suppl. 1), pp. 234-238.

Pincus, David W., Robert R. Goodman, Richard A. R. Fraser, Maiken Nedergaard, and Steven A. Goldman. Apr. 1998. "Neural Stem and Progenitor Cells: A Strategy for Gene Therapy and Brain Repair." *Neurosurgery*. vol. 42, No. 4, pp. 858-867.

Ogiso, M., Y. Yamashita, and T. Matsumoto. Jun. 1998. "The Process of Physical Weakening and Dissolution of the HA-Coated Implant in Bone and Soft Tissue." *Journal of Dental Research*. vol. 77, No. 6, pp. 1426-1434.

Petka, Wendy A., James L. Harden, Kevin P. McGrath, Denis Wirtz, and David A. Tirrell. Jul. 17, 1998. "Reversible Hydrogels from Self-Assembling Artificial Proteins." *Science*. vol. 281, No. 5375, pp. 389-392.

Orgill, Dennis P., Charles Butler, John F. Regan, Mark S. Barlow, I. V. Yannas, and Carolyn C. Compton. Aug. 1998. "Vascularized Collagen-Glycosaminoglycan Matrix Provides a Dermal Substrate and Improves Take of Cultured Epithelial Autografts." *Plastic and Reconstructive Surgery*. vol. 102, No. 2, pp. 423-429.

Yu, Ying-Ching, Matthew Tirrell, and Gregg B. Fields. Oct. 7, 1998. "Minimal Lipidation Stabilizes Protein-Like Molecular Architecture." *Journal of the American Chemical Society*. vol. 120, No. 39, pp. 9979-9987.

Borkenhagen, M., J.-F. Clémence, H. Sigrist, and P. Aebischer. 1998. "Three-Dimensional Extracellular Matrix Engineering in the Nervous System." *Journal of Biomedical Materials Research*. vol. 40, pp. 392-400.

Brekke, John H. and Jeffrey M. Toth. 1998. "Principles of Tissue Engineering Applied to Programmable Osteogenesis." *Journal of Biomedical Materials Research (Appl. Biomater.)*. vol. 43, pp. 380-398.

Fernandez, A., M. A. Alsina, I. Haro, R. Galantai, and F. Reig. 1998. "Synthesis and Physicochemical Characterization of Cyclic Laminin Related Peptides." *Langmuir*. vol. 14, No. 13, pp. 3625-3630.

Fields, Gregg B., Janelle L. Lauer, Yoav Dori, Pilar Forns, Ying-Ching Yu, and Matthew Tirrell. 1998. "Proteinlike Molecular Architecture: Biomaterial Applications for Inducing Cellular Receptor Binding and Signal Transduction." *Biopolymers (Peptide Science)*. vol. 47, pp. 143-151.

Gu, Keni, Syweren R. Chang, Matt S. Slaven, Brian H. Clarkson, R. Bruce Rutherford, and Helena H. Ritchie. 1998. "Human Dentin Phosphophoryn Nucleotide and Amino Acid Sequence." *European Journal of Oral Sciences*. vol. 106, pp. 1043-1047.

Hartgerink, Jeffrey D., Thomas D. Clark, and M. Reza Ghadiri. 1998. "Peptide Nanotubes and Beyond." *Chem. Eur. J.* vol. 4, No. 8, pp. 1367-1372.

Johnstone, Brian, Thomas M. Hering, Arnold I. Caplan, Victor M. Goldberg, and Jung U. Yoo. 1998. "In Vitro Chondrogenesis of Bone Marrow-Derived Mesenchymal Progenitor Cells." *Experimental Cell Research*. vol. 238, pp. 265-272.

Kawasaki, M., A. Ohtomo, I. Ohkubo, H. Koinuma, Z. K. Tang, P. Yu, G. K. L. Wong, B. P. Zhang, and Y. Segawa. 1998. "Excitonic Ultraviolet Laser Emission at Room Temperature from Naturally Made Cavity in ZnO Nanocrytal Thin Films." *Materials Science and Engineering*. vol. B56, pp. 239-245.

Kogiso, Masaki, Satomi Ohnishi, Kiyoshi Yase, Mitsutoshi Masuda, and Toshimi Shimizu. 1998. "Dicarboxylic Oligopeptide Bolaamphiphiles: Proton-Triggered Self-Assembly of Microtubes with Loose Solid Surfaces." *Langmuir*. vol. 14, No. 18, pp. 4978-4986, S1-S7.

Kogiso, Masaki, Takeshi Hanada, Kiyoshi Yase, and Toshimi Shimizu. 1998. "Intralayer Hydrogen-Bond-Directed Self-Assembly of Nano-Fibers from Dicarboxylic Valylvaline Bolaamphiphiles." *Chem. Comm.* pp. 1791-1792.

Li, Panjian and Paul Ducheyne. 1998. "Quasi-Biological Apatite Film Induced by Titanium in a Simulated Body Fluid." *Journal of Biomedical Materials Research*. vol. 41, pp. 341-348.

Nanci, A., J. D. Wuest, L. Peru, P. Brunet, V. Sharma, S. Zalzal, and M. D. McKee. 1998. "Chemical Modification of Titanium Surfaces for Covalent Attachment of Biological Molecules." *Journal of Biomedical Materials Research*. vol. 40, pp. 324-335.

Tsui, Y. C., C. Doyle, and T. W. Clyne. 1998. "Plasma Sprayed Hydroxyapatite Coatings on Titanium Substrates Part 2: Optimisation of Coating Properties." *Biomaterials*. vol. 19, pp. 2031-2043.

Weiner, S. and H. D. Wagner. 1998. "The Material Bone: Structure-Mechanical Function Relations." *Annu. Rev. Mater. Sci.* vol. 28, pp. 271-298.

Wen, H. B., J. R. de Wijn, F. Z. Cui, and K. de Groot. 1998. "Preparation of Calcium Phosphate Coatings on Titanium Implant Materials by Simple Chemistry." *Journal of Biomedical Materials Research*. vol. 41, pp. 227-236.

Wheeler, Donna L., David L. Chamberland, John M. Schmitt, David C. Buck, John H. Brekke, Jeffrey O. Hollinger, S.-P. Joh, and K.-W. Suh. 1998. "Radiomorphometry and Biomechanical Assessment of Recombinant Human Bone Morphogenetic Protein 2 and Polymer in Rabbit Radius Ostectomy Model." *Journal of Biomedical Materials Research (Appl. Biomater.)*. vol. 43, pp. 365-373.

Wolke, J. G. C., K. de Groot, and J. A. Jansen. 1998. "In Vivo Dissolution Behavior of Various RF Magnetron Sputtered Ca-P Coatings." *Journal of Biomedical Materials Research*. vol. 39, pp. 524-530.

Xiao, Shou-Jun, Marcus Textor, and Nicholas D. Spencer. 1998. "Covalent Attachment of Cell-Adhesive, (Arg-Gly-Asp)-Containing Peptides to Titanium Surfaces." *Langmuir*. vol. 14, No. 19, pp. 5507-5516.

Xu, Guofeng, Nan Yao, Ilhan A. Aksay, and John T. Groves. 1998. "Biomimetic Synthesis of Macroscopic-Scale Calcium Carbonate Thin Films. Evidence for a Multistep Assembly Process." *Journal of the American Chemical Society*. vol. 120, No. 46, pp. 11977-11985.

Yamada, Norihiro, Katsuhiko Ariga, Masanobu Naito, Kazuhiro Matsubara, and Emiko Koyama. 1998. "Regulation of β-Sheet Structures Within Amyloid-Like β-Sheet Assemblage from Tripeptide Derivatives." *Journal of the American Chemical Society*. vol. 120, No. 47, pp. 12192-12199.

Chusuei, Charles C., D. Wayne Goodman, Michael J. Van Stipdonk, Dina R. Justes, and Emile A. Schweikert. Jan. 1, 1999. "Calcium Phosphate Phase Identification Using XPS and Time-of-Flight Cluster SIMS." *Analytical Chemistry*. vol. 71, No. 1, pp. 149-153.

Zubarev, Eugene R., Martin U. Pralle, Leiming Li, and Samuel I. Stupp. Jan. 22, 1999. "Conversion of Supramolecular Clusters to Macromolecular Objects." *Science*. vol. 283, pp. 523-526.

Won, You-Yeon, H. Ted Davis, and Frank S. Bates. Feb. 12, 1999. "Giant Wormlike Rubber Micelles." *Science*. vol. 283, No. 5404, pp. 960-963.

Corral, Claudio J., Aamir Siddiqui, Liancun Wu, Catherine L. Farrell, David Lyons, and Thomas A. Mustoe. Feb. 1999. "Vascular Endothelial Growth Factor is More Important Than Basic Fibroblastic Growth Factor During Ischemic Wound Healing." *Arch. Surg.* vol. 134, pp. 200-205.

Wheeler, B. C., J. M. Corey, G. J. Brewer, and D. W. Branch. Feb. 1999. "Microcontact Printing for Precise Control of Nerve Cell Growth in Culture." *Journal of Biomechanical Engineering*. vol. 121, pp. 73-78.

Cao, H., Y. G. Zhao, S. T. Ho, E. W. Seelig, Q. H. Wang, and R. P. H. Chang. Mar. 15, 1999. "Random Laser Action in Semiconductor Powder." *Physical Review Letters*. vol. 82, No. 11, pp. 2278-2281.

Aizenberg, Joanna, Andrew J. Black, and George M. Whitesides. Apr. 8, 1999. "Control of Crystal Nucleation by Patterned Self-Assembled Monolayers." *Nature*. vol. 398, pp. 495-498.

Niklason, L. E., J. Gao, W. M. Abbott, K. K. Hirschi, S. Houser, R. Marini, and R. Langer. Apr. 16, 1999. "Functional Arteries Grown in Vitro." *Science*. vol. 284, pp. 489-493.

Hahn, Jungseok and Stephen E. Webber. Apr. 1999. "Modification of Surfaces by Covalent Attachment of Polymer Micelles." *Macromolecular Symposia*. vol. 139, pp. 39-47.

Liu, Yi, Duckhyun Kim, B. Timothy Himes, Stella Y. Chow, Timothy Schallert, Marion Murray, Alan Tessler, and Itzhak Fischer. Jun. 1, 1999. "Transplants of Fibroblasts Genetically Modified to Express BDNF Promote Regeneration of Adult Rat Rubrospinal Axons and Recovery of Forelimb Function." *The Journal of Neuroscience*. vol. 19, No. 11, pp. 4370-4387.

Mehler, Mark F. and John A. Kessler. Jul. 1999. "Progenitor Cell Biology: Implications for Neural Regeneration." *Arch. Neurol.* vol. 56, pp. 780-784.

Tirrell, M. Oct. 27, 1999. "Biofunctionalization of Surfaces with Peptide Amphiphiles." *AVS: Science & Technology*. Invited Paper BI-WeM7.

McDonald, John W., Xiao-Zhong Liu, Yun Qu, Su Liu, Shannon K. Mickey, Dorothy Turetsky, David I. Gottlieb, and Dennis W. Choi. Dec. 1999. "Transplanted Embryonic Stem Cells Survive, Differentiate and Promote Recovery in Injured Rat Spinal Cord." *Nature Medicine*. vol. 5, No. 12, pp. 1410-1412.

Bradt, Jens-Hilmar, Michael Mertig, Angelika Teresiak, and Wolfgang Pompe. 1999. "Biomimetic Mineralization of Collagen by Combined Fibril Assembly and Calcium Phosphate Formation." *Chem. Mater*. vol. 11, No. 10, pp. 2694-2701.

Braun, Paul V. and Samuel I. Stupp. 1999. "CdS Mineralization of Hexagonal, Lamellar, and Cubic Lyotropic Liquid Crystals." *Materials Research Bulletin*. vol. 34, No. 3, pp. 463-469.

Butler, C. E., I. V. Yannas, C. C. Compton, C. A. Correia, and D. P. Orgill. 1999. "Comparison of Cultured and Uncultured Keratinocytes Seeded into a Collagen-GAG Matrix for Skin Replacements." *British Journal of Plastic Surgery*. vol. 52, pp. 127-132.

Chai, C. S. and B. Ben-Nissan. 1999. "Bioactive Nanocrystalline Sol-Gel Hydroxyapatite Coatings." *Journal of Materials Science: Materials in Medicine*. vol. 10, pp. 465-469.

Clark, Thomas D., Kenji Kobayashi, and M. Reza Ghadiri. 1999. "Covalent Capture and Stabilization of Cylindrical β-Sheet Peptide Assemblies." *Chem. Eur. J.* vol. 5, No. 2, pp. 782-792.

Cornish, J., K. E. Callon, C. Q.-X. Lin, C. L. Xiao, T. B. Mulvey, G. J. S. Cooper, and I. R. Reid. 1999. "Trifluoroacetate, a Contaminant in Purified Proteins, Inhibits Proliferation of Osteoblasts and Chondrocytes." *Am. J. Physiol. Endocrinol. Metab*. vol. 277, pp. 779-783.

Emoto, Kazunori, Yukio Nagasaki, and Kazunori Kataoka. 1999. "Coating of Surfaces with Stabilized Reactive Micelles from Poly-(ethylene glycol)—Poly(DL-Lactic Acid) Block Copolymer." *Langmuir*. vol. 15, No. 16, pp. 5212-5218.

Fields, Gregg B. 1999. "Induction of Protein-like Molecular Architecture by Self-Assembly Processes." *Bioorganic & Medicinal Chemistry*. vol. 7, pp. 75-81.

Haynes, Andrew J., Wei-Qun Huang, Jamie Mallah, Dajun Yang, Marc E. Lippman, and Lu-Yuan Li. 1999. "Angiopoietin-1 and its Receptor Tie-2 Participate in the Regulation of Capillary-like Tubule Formation and Survival of Endothelial Cells." *Microvascular Research*. vol. 58, pp. 224-237.

Hwang, Julia J., Kevin Jaeger, James Hancock, and Samuel I. Stupp. 1999. "Organoapatite Growth on an Orthopedic Alloy Surface." *Journal of Biomedical Materials Research*. vol. 47, pp. 504-515.

Ignjatović, Nenad, Simonida Tomić, Momčilo Dakić, Miroslav Miljković, Milenko Plavšić, and Dragan Uskoković. 1999. "Synthesis and Properties of Hydroxyapatite/Poly-L-Lactide Composite Biomaterials." *Biomaterials*. vol. 20, pp. 809-816.

Lee, Kevin J. and Thomas M. Jessell. 1999. "The Specification of Dorsal Cell Fates in the Vertebrate Central Nervous System." *Annual Review of Neuroscience*. vol. 22, pp. 261-294.

Lee, Kyujin C., Paul A. Carlson, Alex S. Goldstein, Paul Yager, and Michael H. Gelb. 1999. "Protection of a Decapeptide from Proteolytic Cleavage by Lipidation and Self-Assembly into High-Axial-Ratio Microstructures: A Kinetic and Structural Study." *Langmuir*. vol. 15, No. 17, pp. 5500-5508.

Mao, Chuanbin, Hengde Li, Fuzhai Cui, Chunlai Ma, and Qinglin Feng. 1999. "Oriented Growth of Phosphates on Polycrystalline Titanium in a Process Mimicking Biomineralization." *Journal of Crystal Growth*. vol. 206, pp. 308-321.

Miyaji, Fumiaki, Hyun-Min Kim, Shinichi Handa, Tadashi Kokubo, and Takashi Nakamura 1999. "Bonelike Apatite Coating on Organic Polymers: Novel Nucleation Process Using Sodium Silicate Solution." *Biomaterials*. vol. 20, pp. 913-919.

Pakalns, Teika, Kraig L. Haverstick, Gregg B. Fields, James B. McCarthy, Daniel L. Mooradian, and Matthew Tirrell. 1999. "Cellular Recognition of Synthetic Peptide Amphiphiles in Self-Assembled Monolayer Films." *Biomaterials*. vol. 20, pp. 2265-2279.

Pittenger, Mark F., Alastair M. Mackay, Stephen C. Beck, Rama K. Jaiswal, Robin Douglas, Joseph D. Mosca, Mark A. Moorman, Donald W. Simonetti, Stewart Craig, and Daniel R. Marshak. Apr. 2, 1999. "Multilineage Potential of Adult Human Mesenchymal Stem Cells." *Science*. vol. 284, pp. 143-147.

Rezania, Alireza, Robert Johnson, Anthony R. Lefkow, and Kevin E. Healy. 1999. "Bioactivation of Metal Oxide Surfaces. 1. Surface Characterization and Cell Response." *Langmuir*. vol. 15, No. 20, pp. 6931-6939.

Rowley, Jon A., Gerard Madlambayan, and David J. Mooney. 1999. "Alginate Hydrogels as Synthetic Extracellular Matrix Materials." *Biomaterials*. vol. 20, pp. 45-53.

Schense, Jason C. and Jeffrey A. Hubbell. 1999. "Cross-Linking Exogenous Bifunctional Peptides into Fibrin Gels with Factor XIIIa." *Bioconjugate Chem*. vol. 10, No. 1, pp. 75-81.

Varma, H. K., Y. Yokogawa, F. F. Espinosa, Y. Kawamoto, K. Nishizawa, F. Nagata, and T. Kameyama. 1999. "In-Vitro Calcium Phosphate Growth over Functionalized Cotton Fibers." *Journal of Materials Science: Materials in Medicine*. vol. 10, pp. 395-400.

Vernon, Robert B. and E. Helene Sage. 1999. "A Novel, Quantitative Model for Study of Endothelial Cell Migration and Sprout Formation Within Three-Dimensional Collagen Matrices." *Microvascular Research*. vol. 57, pp. 188-133.

Wei, M., A. J. Ruys, M. V. Swain, S. H. Kim, B. K. Milthorpe, and C. C. Sorrell. 1999. "Interfacial Bond Strength of Electrophoretically Deposited Hydroxyapatite Coatings on Metals." *Journal of Materials Science: Materials in Medicine*. vol. 10, pp. 401-409.

Yagi, Nobuhiro, Yoshikatsu Ogawa, Masato Kodaka, Tomoko Okada, Takenori Tomohiro, Takeo Konakahara, and Hiroaki Okuno. 1999. "A Surface-Modified Functional Liposome Capable of Binding to Cell Membranes." *Chem. Commun.* pp. 1687-1688.

Yu, Ying-Ching, Vikram Roontga, Vladimir A. Daragan, Kevin H. Mayo, Matthew Tirrell, and Gregg B. Fields. 1999. "Structure and Dynamics of Peptide—Amphiphiles Incorporating Triple-Helical Proteinlike Molecular Architecture." *Biochemistry*. vol. 38, No. 5, pp. 1659-1668.

Huq, N. Laila, Keith J. Cross, and Eric C. Reynolds. Feb. 4, 2000. "Molecular Modelling of a Multiphosphorylated Sequence Motif Bound to Hydroxyapatite Surfaces." *Journal of Molecular Modeling*. vol. 6, pp. 35-47.

Martinez, J. S., G. P. Zhang, P. D. Holt, H.-T. Jung, C. J. Carrano, M. G. Haygood, and Alison Butler. Feb. 18, 2000. "Self-Assembling Amphiphilic Siderophores from Marine Bacteria." *Science*. vol. 287, No. 5456, pp. 1245-1247.

Verrecchio, Angela, Markus W. Germann, Barbara P. Schick, Brian Kung, Thomas Twardowski, and James D. San Antonio. Mar. 17, 2000. "Design of Peptides with High Affinities for Heparin and Endothelial Cell Proteoglycans." *The Journal of Biological Chemistry*. vol. 275, No. 11, pp. 7701-7707.

Cao, H., J. Y. Xu, E. W. Seelig, and R. P. H. Chang. May 22, 2000. "Microlaser Made of Disordered Media." *Applied Physics Letters*. vol. 76, No. 21, pp. 2997-2999.

Marler, Jennifer J., Amrita Guha, Jonathan Rowley, Rahul Koka, David Mooney, Joseph Upton, and Joseph Vacanti. May 2000. "Soft-Tissue Augmentation with Injectable Alginate and Syngeneic Fibroblasts." *Plastic and Reconstructive Surgery*. vol. 105, No. 6, pp. 2049-2058.

Holmes, Todd C., Sonsoles de Lacalle, Xing Su, Guosong Liu, Alexander Rich, and Shuguang Zhang. Jun. 6, 2000. "Extensive Neurite Outgrowth and Active Synapse Formation on Self-Assembling Peptide Scaffolds." *Proceedings of the National Academy of Sciences of the United States of America*. vol. 97, No. 12, pp. 6728-6733.
Whaley, Sandra R., D. S. English, Evelyn L. Hu, Paul F. Barbara, and Angela M. Belcher. Jun. 8, 2000. "Selection of Peptides with Semiconductor Binding Specificity for Directed Nanocrystal Assembly." *Nature*. vol. 405, pp. 665-668.
Sun, Xiu-xia and Chi-chen Wang. Jul. 28, 2000. "The N-Terminal Sequence (Residues 1-65) is Essential for Dimerization, Activities, and Peptide Binding of *Escherichia coli* DsbC." *The Journal of Biological Chemistry*. vol. 275, No. 30, pp. 22743-22749.
Hsu, Wei-Cherng, Mark H. Spilker, Ioannis V. Yannas, and Peter A. D. Rubin. Aug. 2000. "Inhibition of Conjunctival Scarring and Contraction by a Porous Collagen-Glycosaminoglycan Implant." *Investigative Ophthalmology & Visual Science*. vol. 41, No. 9, pp. 2404-2411.
Schlessinger, Joseph, Alexander N. Plotnikov, Omar A. Ibrahimi, Anna V. Eliseenkova, Brian K. Yeh, Avner Yayon, Robert J. Linhardt, and Moosa Mohammadi. Sep. 2000. "Crystal Structure of a Ternary FGF-FGFR-Heparin Complex Reveals a Dual Role for Heparin in FGFR Binding and Dimerization." *Molecular Cell*. vol. 6, pp. 743-750.
Sun, Y., J. B. Ketterson, and G. K. L. Wong. Oct. 9, 2000. "Excitonic Gain and Stimulated Ultraviolet Emission in Nanocrystalline Zinc-Oxide Powder." *Applied Physics Letters*. vol. 77, No. 15, pp. 2322-2324.
Schuldiner, Maya, Ofra Yanuka, Joseph Itskovitz-Eldor, Douglas A. Melton, and Nissim Benvenisty. Oct. 10, 2000. "Effects of Eight Growth Factors on the Differentiation of Cells Derived from Human Embryonic Stem Cells." *Proceedings of the National Academy of Sciences of the United States of America*. vol. 97, No. 21, pp. 11307-11312.
Altman, Michael, Peter Lee, Alexander Rich, and Shuguang Zhang. 2000. "Conformational Behavior of Ionic Self-Complementary Peptides." *Protein Science*. vol. 9, pp. 1095-1105.
Archer, Eric A., Noah T. Goldberg, Vincent Lynch, and Michael J. Krische. 2000. "Nanostructured Polymer Duplexes via the Covalent Casting of 1-Dimensional H-Bonding Motifs: A New Strategy for the Self-Assembly of Macromolecular Precursors." *Journal of the American Chemical Society*. vol. 122, No. 20, pp. 5006-5007.
Ariga, Katsuhiko, Jun-ichi Kikuchi, Masanobu Naito, Emiko Koyama, and Norihiro Yamada. 2000. "Modulated Supramolecular Assemblies Composed of Tripeptide Derivatives: Formation of Micrometer-Scale Rods, Nanometer-Size Needles, and Regular Patterns with Molecular-Level Flatness from the Same Compound." *Langmuir*. vol. 16, No. 11, pp. 4929-4939.
Beniash, E., W. Traub, A. Veis, and S. Weiner. 2000. "A Transmission Electron Microscope Study Using Vitrified Ice Sections of Predentin: Structural Changes in the Dentin Collagenous Matrix Prior to Mineralization." *Journal of Structural Biology*. vol. 132, pp. 212-225.
Bigi, Adriana, Elisa Boanini, Silvia Panzavolta, and Norberto Roveri. 2000. "Biomimetic Growth of Hydroxyapatite on Gelatin Films Doped with Sodium Polyacrylate." *Biomacromolecules*. vol. 1, No. 4, pp. 752-756.
Bourel, Line, Olivier Carion, Hélène Gras-Masse, and Oleg Melnyk. 2000. "The Deprotection of Lys(Mtt) Revisited." *Journal of Peptide Science*. vol. 6, pp. 264-270.
Caplan, Michael R., Peter N. Moore, Shuguang Zhang, Roger D. Kamm, and Douglas A. Lauffenburger. 2000. "Self-Assembly of a β-Sheet Protein Governed by Relief of Electrostatic Repulsion Relative to van der Waals Attraction." *Biomacromolecules*. vol. 1, No. 4, pp. 627-631.
Cardullo, F., M. Crego Calama, B. H. M. Snellink-Ruël, J.-L. Weidmann, A. Bielejewska, R. Fokkens, N. M. M. Nibbering, P. Timmerman, and D. N. Reinhoudt. 2000. "Covalent Capture of Dynamic Hydrogen-Bonded Assemblies." *Chem. Commun.* pp. 367-368.
Chamberlain, L. J., I. V. Yannas, H-P. Hsu, G. R. Strichartz, and M. Spector. 2000. "Near-Terminus Axonal Structure and Function Following Rat Sciatic Nerve Regeneration Through a Collagen-GAG Matrix in a Ten-Millimeter Gap." *Journal of Neuroscience Research*. vol. 60, pp. 666-677.
David, Sunil A., Satish K. Awasthi, and P. Balaram. 2000. "The Role of Polar and Facial Amphipathic Character in Determining Lipopolysaccharide-Binding Properties in Synthetic Cationic Peptides." *Journal of Endotoxin Research*. vol. 6, No. 3, pp. 249-256.
Dori, Yoav, Havazelet Bianco-Peled, Sushil K. Satija, Gregg B. Fields, James B. McCarthy, and Matthew Tirrell. 2000. "Ligand Accessibility as Means to Control Cell Response to Bioactive Bilayer Membranes." *Journal of Biomedical Materials Research*. vol. 50, pp. 75-81.
Forns, Pilar, Janette L. Lauer-Fields, Su Gao, and Gregg B. Fields. 2000. "Induction of Protein-Like Molecular Architecture by Monoalkyl Hydrocarbon Chains." *Biopolymers*. vol. 54, pp. 531-546.
Hisaeda, Yoshio, Eiji Ohshima, and Makiko Arimura. 2000. "Aggregation Behavior of Synthetic Peptide Lipids with Arginine in Aqueous Solution and Construction of a Vitamin $B_{12}$ Artifical Enzyme." *Colloids and Surfaces A: Physicochemical and Engineering Aspects*. vol. 169, pp. 143-153.
Kogiso, Masaki, Yuji Okada, Takeshi Hanada, Kiyoshi Yase, and Toshimi Shimizu. 2000. "Self-Assembled Peptide Fibers from Valylvaline Bola-Amphiphiles by a Parallel β-Sheet Network." *Biochimica et Biophysica Acta*. vol. 1475, pp. 346-352.
Langer, Robert. 2000. "Biomaterials in Drug Delivery and Tissue Engineering: One Laboratory's Experience." *Accounts of Chemical Research*. vol. 33, No. 2, pp. 94-101.
Liu, X. D., M. Skold, T. Umino, Y. K. Zhu, D. J. Romberger, J. R. Spurzem, and S. I. Rennard. 2000. "Endothelial Cell-Mediated Type I Collagen Gel Contraction is Regulated by Hemin." *J. Lab. Clin. Med*. vol. 136, No. 2, pp. 100-109.
Lu, Lichun, Susan J. Peter, Michelle D. Lyman, Hui-Lin Lai, Susan M. Leite, Janet A. Tamada, Shiro Uyama, Joseph P. Vacanti, Robert Langer, and Antonios G. Mikos. 2000. "In Vitro and in Vivo Degradation of Porous Poly(DL-Lactic-*co*-Glycolic Acid) Foams." *Biomaterials*. vol. 21, pp. 1837-1845.
Matsuura, T., R. Hosokawa, K. Okamoto, T. Kimoto, and Y. Akagawa. 2000. "Diverse Mechanisms of Osteoblast Spreading on Hydroxyapatite and Titanium." *Biomaterials*. vol. 21, pp. 1121-1127.
Mulloy, Barbara and Mark J. Forster. 2000. "Conformation and Dynamics of Heparin and Heparan Sulfate." *Glycobiology*. vol. 10, No. 11, pp. 1147-1156.
Ponticiello, Michael S., Robert M. Schinagl, Sudha Kadiyala, and Frank P. Barry. 2000. "Gelatin-Based Resorbable Sponge as a Carrier Matrix for Human Mesenchymal Stem Cells in Cartilage Regeneration Therapy." *Journal of Biomedical Materials Research*. vol. 52, pp. 246-255.
Powell, Sharon K., Jayashree Rao, Eva Roque, Motoyoshi Nomizu, Yuichiro Kuratomi, Yoshihiko Yamada, and Hynda K. Kleinman. 2000. "Neural Cell Response to Multiple Novel Sites on Laminin-1." *Journal of Neuroscience Research*. vol. 61, pp. 302-312.
Rapaport, Hanna, Kristian Kjaer, Torben R. Jensen, Leslie Leiserowitz, and David A. Tirrell. 2000. "Two-Dimensional Order in β-Sheet Peptide Monolayers." *Journal of the American Chemical Society*. vol. 122, No. 50, pp. 12523-12529.
Sakiyama-Elbert, Shelly E. and Jeffrey A. Hubbell. 2000. "Controlled Release of Nerve Growth Factor from a Heparin-Containing Fibrin-Based Cell Ingrowth Matrix." *Journal of Controlled Release*. vol. 69, pp. 149-158.
Sakiyama-Elbert, Shelly E. and Jeffrey A. Hubbell. 2000. "Development of Fibrin Derivatives for Controlled Release of Heparin-Binding Growth Factors." *Journal of Controlled Release*. vol. 65, pp. 389-402.
Thareja, R. K. and A. Mitra. 2000. "Random Laser Action in ZnO." *Appl. Phys*. vol. B 71, pp. 181-184.
Tunggal, Patrick, Neil Smyth, Mats Paulsson, and Mark-Christoph Ott. 2000. "Laminins: Structure and Genetic Regulation." *Microscopy Research and Technique*. vol. 51, pp. 214-227.
do Serro, Ana Paula Valagão Amadeu, Anabela Catarino Fernandes, and Benilde de Jesus Vieira Saramago. 2000. "Calcium Phosphate Deposition on Titanium Surfaces in the Presence of Fibronectin." *Journal of Biomedical Materials Research*. vol. 49, pp. 345-352.
Yamada, Norihiro and Katsuhiko Ariga. 2000. "Formation of β-Sheet Assemblage with a View to Developing an Amyloid Model." *Synlett*. vol. 5, pp. 575-586.

Yang, Lin and Paschalis Alexandridis. 2000. "Physicochemical Aspects of Drug Delivery and Release from Polymer-Based Colloids." *Current Opinion in Colloid & Interface Science*. vol. 5, pp. 132-143.

Yu, Huanran, Hiroshi Narusawa, Kisae Itoh, Akihiro Oshi, Narutoshi Yoshino, Kazuo Ohbu, Toshiaki Shirakawa, Kazuhiro Fukada, Masatoshi Fujii, Tadashi Kato, and Tsutomu Seimiya. 2000. "Hydrophilicity of Polar and Apolar Domains of Amphiphiles." *Journal of Colloid and Interface Science*. vol. 229, pp. 375-390.

Zhu, G., M. F. Mehler, P. C. Mabie, and J. A. Kessler. 2000. "Developmental Changes in Neural Progenitor Cell Lineage Commitment Do Not Depend on Epidermal Growth Factor Receptor Signaling." *Journal of Neuroscience Research*. vol. 59, pp. 312-320.

Jin, Young-Gu and K. J. Chang. Feb. 26, 2001. "Mechanism for the Enhanced Diffusion of Charged Oxygen Ions in $SiO_2$." *Physical Review Letters*. vol. 86, No. 9, pp. 1793-1796.

Orlic, Donald, Jan Kajstura, Stefano Chimenti, Igor Jakonuk, Stacie M. Anderson, Baosheng Li, James Picket, Ronald McKay, Bernardo Nadal-Ginard, David M. Bodine, Annarosa Leri, and Piero Anversa. Apr. 5, 2001. "Bone Marrow Cells Regenerate Infarcted Myocardium." *Nature*. vol. 410, pp. 701-705.

Vailhé, Bruno, Daniel Vittet, and Jean-Jacques Feige. Apr. 2001. "In Vitro Models of Vasculogenesis and Angiogenesis." *Laboratory Investigation*. vol. 81, No. 4, pp. 439-452.

Merkler, Doron, Gerlinde A. S. Metz, Olivier Raineteau, Volker Dietz, Martin E. Schwab, and Karim Fouad. May 15, 2001. "Locomotor Recovery in Spinal Cord-Injured Rats Treated with an Antibody Neutralizing the Myelin-Associated Neurite Growth Inhibitor Nogo-A." *The Journal of Neuroscience*. vol. 21, No. 10, pp. 3665-3673.

Davis, N. G., J. Teisen, C. Schuh, and D. C. Dunand. May 2001. "Solid-State Foaming of Titanium by Superplastic Expansion of Argon-Filled Pores." *J Mater. Res*. vol. 16, No. 5, pp. 1508-1519.

Rabchevsky, Alexander G. and George M. Smith. May 2001. "Therapeutic Interventions Following Mammalian Spinal Cord Injury." *Arch. Neurol*. vol. 58, pp. 721-726.

Huang, Michael H., Samuel Mao, Henning Feick, Haoquan Yan, Yiying Wu, Hannes Kind, Eicke Weber, Richard Russo, and Peidong Yang. Jun. 8, 2001. "Room-Temperature Ultraviolet Nanowire Nanolasers." *Science*. vol. 292, pp. 1897-1899.

Lee, Kuen Yong and David J. Mooney. Jul. 2001. "Hydrogels for Tissue Engineering." *Chemical Reviews*. vol. 101, No. 7, pp. 1869-1879.

Aggeli, A., I. A. Nyrkova, M. Bell, R. Harding, L. Carrick, T. C. B. McLeish, A. N. Semenov, and N. Boden. Oct. 9, 2001. "Hierarchical Self-Assembly of Chiral Rod-Like Molecules as a Model for Peptide β-Sheet Tapes, Ribbons, Fibrils, and Fibers." *Proceedings of the National Academy of Sciences of the United States of America*. vol. 98, No. 21, pp. 11857-11862.

Hartgerink, Jeffrey D., Elia Beniash, and Samuel I. Stupp. Nov. 23, 2001. "Self-Assembly and Mineralization of Peptide-Amphiphile Nanofibers." *Science*. vol. 294, pp. 1684-1688.

Richardson, Thomas P., Martin C. Peters, Alessandra B. Ennett, and David J. Mooney. Nov. 2001. "Polymeric System for Dual Growth Factor Delivery." *Nature Biotechnology*. vol. 19, pp. 1029-1034.

Matsui, Hiroshi and Robert MacCuspie. Dec. 2001. "Metalloporphyrin Nanotube Fabrication Using Peptide Nanotubes as Templates." *Nano Letters*. vol. 1, No. 12, pp. 671-675.

Mathew, Mathai and Shozo Takagi. Nov.-Dec. 2001. "Structures of Biological Minerals in Dental Research." *Journal of Research of the National Institute of Standards and Technology*. vol. 106, No. 6, pp. 1035-1044.

Woo, Byung Ho, Betsy F. Fink, Richard Page, Jay A. Schrier, Yeong Woo Jo, Ge Jiang, Michelle DeLuca, Henry C. Vasconez, and Patrick P. DeLuca. Dec. 2001. "Enhancement of Bone Growth by Sustained Delivery of Recombinant Human Bone Morphogenetic Protein-2 in a Polymeric Matrix." *Pharmaceutical Research*. vol. 18, No. 12, pp. 1747-1753.

Barrère, F., P. Layrolle, C. A. Van Blitterswijk, and K. de Groot. 2001. "Biomimetic Coatings on Titanium: A Crystal Growth Study of Octacalcium Phosphate." *Journal of Materials Science: Materials in Medicine*. vol. 12, pp. 529-534.

Bianco-Peled, Havazelet, Yoav Dori, James Schneider, Li-Piin Sung, Sushil Satija, and Matthew Tirrell. 2001. "Structural Study of Langmuir Monolayers Containing Lipidated Poly(ethylene glycol) and Peptides." *Langmuir*. vol. 17, No. 22, pp. 6931-6937.

Bonnet, Dominique, Kader Thiam, Estelle Loing, Oleg Melnyk, and Hélène Gras-Masse. 2001. Synthesis by Chemoselective Ligation and Biological Evaluation of Novel Cell-Permeable PKC-ζ Pseudosubstrate Lipopeptides. *J. Med. Chem*. vol. 44, No. 3, pp. 468-471.

Cavalli, M., G. Gnappi, A. Montenero, D. Bersani, P. P. Lottici, S. Kaciulis, G. Mattogno, and M. Fini. 2001. "Hydroxy- and Fluorapatite Films on Ti Alloy Substrates: Sol-gel Preparation and Characterization." *Journal of Materials Science*. vol. 36, pp. 3253-3260.

Chang, John C., Gregory J. Brewer, and Bruce C. Wheeler. 2001. "Modulation of Neural Network Activity by Patterning." *Biosensors & Bioelectronics*. vol. 16, pp. 527-533.

Chang, Sophia C. N., Jon A. Rowley, Geoffrey Tobias, Nicholas G. Genes, Amit K. Roy, David J. Mooney, Charles A. Vacanti, and Lawrence J. Bonassar. 2001. "Injection Molding of Chondrocyte/Alginate Constructs in the Shape of Facial Implants." *Journal of Biomedical Materials Research*. vol. 55, pp. 503-511.

Doi, Tomokiyo, Takatoshi Kinoshita, Hiroki Kamiya, Shintaro Washizu, Yoshiharu Tsujita, and Hiraoki Yoshimizu. 2001. "Aggregation of Polypeptide-Based Amphiphiles in Water." *Polymer Journal*. vol. 33, No. 2, pp. 160-164.

Gore, Tushar, Yoav Dori, Yeshayahu Talmon, Matthew Tirrell, and Havazelet Bianco-Peled. 2001. "Self-Assembly of Model Collagen Peptide Amphiphiles." *Langmuir*. vol. 17, No. 17, pp. 5352-5360.

Grothe, Claudia and Guido Nikkhah 2001. "The role of Basic Fibroblast Growth Factor in Peripheral Nerve Regeneration." *Anat. Embryol*. vol. 204, pp. 171-177.

Hoess, Ronald H. 2001. "Protein Design and Phage Display." *Chemical Reviews*. Vol. 101, No. 10, pp. 3205-3218.

Huang, Eric J. and Louis F. Reichardt. 2001. "Neurotrophins: Roles in Neuronal Development and Function." *Annual Review of Neuroscience*. vol. 24, pp. 677-736.

Irvine, Darrell J. and Anne M. Mayes. 2001. "Nanoscale Clustering of RGD Peptides at Surfaces Using Comb Polymers. 1. Synthesis and Characterization of Comb Thin Films." *Biomacromolecules*. vol. 2, No. 1, pp. 85-94.

Kam, L., W. Shain, J. N. Turner, and R. Bizios. 2001. "Axonal Outgrowth of Hippocampal Neurons on Micro-Scale Networks of Polylysine-Conjugated Laminin." *Biomaterials*. vol. 22, pp. 1049-1054.

Kikuchi, Masanori, Soichiro Itoh, Shizuko Ichinose, Kenichi Shinomiya, and Junzo Tanaka. 2001. "Self-Organization Mechanism in a Bone-Like Hydroxyapatite/Collagen Nancomposite Synthesized in Vitro and its Biological Reaction in Vivo." *Biomaterials*. vol. 22, pp. 1705-1711.

Liu, Yuelian, Pierre Layrolle, Joost de Bruijn, Clemens van Blitterswijk, and Klaas de Groot. 2001. "Biomimetic Coprecipitation of Calcium Phosphate and Bovine Serum Albumin on Titanium Alloy." *Journal of Biomedical Materials Research*. vol. 57, pp. 327-335.

Look, D. C. 2001. "Recent Advances in ZnO Materials and Devices." *Materials Science and Engineering*. vol. B80, pp. 383-387.

Luo, Yi and Glenn D. Prestwich. 2001. "Novel Biomaterials for Drug Delivery." Expert Opin. Ther. Patents. vol. 11, No. 9, pp. 1395-1410.

Marchi-Artzner, Valerie, Barbara Lorz, Ulrike Hellerer, Martin Kantlehner, Horst Kessler, and Erich Sackmann 2001. "Selective Adhesion of Endothelial Cells to Artificial Membranes with a Synthetic RGD-Lipopeptide." *Chem. Eur. J*. vol. 7, No. 5, pp. 1095-1101.

Matsui, Hiroshi, and Gary E. Douberly, Jr. 2001. "Organization of Peptide Nanotubes into Macroscopic Bundles." *Langmuir*. vol. 17, No. 25, pp. 7918-7922.

Matsui, Hiroshi, Precila Porrata, and Gary E. Douberly, Jr. 2001. "Protein Tubule Immobilization on Self-Assembled Monolayers on Au Substrates." *Nano Letters*. vol. 1, No. 9, pp. 461-464.

Neet, K. E. and R. B. Campenot. 2001. "Receptor Binding, Internalization, and Retrograde Transport of Neurotrophic Factors." *CMLS, Cell Mol. Life Sci*. vol. 58, pp. 1021-1035.

Otsuka, Hidenori, Yukio Nagasaki, and Kazunori Kataoka. 2001. "Self-Assembly of Poly(ethylene glycol)—based Block Copolymers for Biomedical Applications." *Current Opinion in Colloid & Interface Science*. vol. 6, pp. 3-10.

Shimizu, Toshimi, Rika Iwaura, Mitsutoshi Masuda, Takeshi Hanada, and Kiyoshi Yase. 2001. "Internucleobase-Interaction-Directed Self-Assembly of Nanofibers from Homo- and Heteroditopic 1,ω-Nucleobase Bolaamphiphiles." *Journal of the American Chemical Society*. vol. 123, No. 25, pp. 5947-5955, S1-S16.

Socrates, George. 2001. *Infrared and Raman Characteristic Group Frequencies: Tables and Charts*. Third Edition. Chichester, England: John Wiley & Sons Ltd.

Spanos, Nikos and Petros G. Koutsoukos. 2001. "Model Studies of the Effect of Orthophospho-L-Serine on Biological Mineralization." *Langmuir*. vol. 17, No. 3, pp. 866-872.

Takadama, Hiroaki, Hyun-Min Kim, Tadashi Kokubo, and Takashi Nakamura. 2001. "TEM-EDX Study of Mechanism of Bonelike Apatite Formation on Bioactive Titanium Metal in Simulated Body Fluid." *Journal of Biomedical Materials Research*. vol. 57, pp. 441-448.

Tanihara, Masao, Yasuo Suzuki, Eriko Yamamoto, Atsushi Noguchi, and Yutaka Mizushima. 2001. "Sustained Release of Basic Fibroblast Growth Factor and Angiogenesis in a Novel Covalently Crosslinked Gel of Heparin and Alginate." *Journal of Biomedical Materials Research*. vol. 56, pp. 216-221.

Torchilin, Vladimir P. 2001. "Structure and Design of Polymeric Surfactant-Based Drug Delivery Systems." *Journal of Controlled Release*. vol. 73, pp. 137-172.

Yeung, C. K., L. Lauer, A. Offenhäusser, and W. Knoll. 2001. "Modulation of the Growth and Guidance of Rat Brain Stem Neurons Using Patterned Extracellular Matrix Proteins." *Neuroscience Letters*. vol. 301, pp. 147-150.

Zubarev, Eugene R., Martin U. Pralle, Eli D. Sone, and Samuel I. Stupp. 2001. "Self-Assembly of Dendron Rodcoil Molecules into Nanoribbons." *Journal of the American Chemical Society*. vol. 123, No. 17, pp. 4105-4106.

Hirschi, Karen K., Lihua Lai, Narasimhaswamy S. Belaguli, David A. Dean, Robert J. Schwartz, and Warren E. Zimmer. Feb. 22, 2002. "Transforming Growth Factor-β Induction of Smooth Muscle Cell Phenotype Requires Transcriptional and Post-transcriptional Control of Serum Response Factor." *The Journal of Biological Chemistry*. vol. 277, No. 8, pp. 6287-6295.

Xu, Weiming, Lizhi Liu, and Ian G. Charles. Feb. 2002. "Microencapsulated iNOS-expressing Cells Cause Tumor Suppression in Mice." *The FASEB Journal*. vol. 16, pp. 213-215.

Zubarev, Eugene R., Martin U. Pralle, Eli D. Sone, and Samuel I. Stupp. Feb. 2002. "Scaffolding of Polymers by Supramolecular Nanoribbons." *Advanced Materials*. vol. 14, No. 3, pp. 198-203.

Slocik, Joseph M., Joshua T. Moore, and David W. Wright. Mar. 2002. Monoclonal Antibody Recognition of Histidine-Rich Peptide Encapsulated Nanoclusters. *Nano Letters*. vol. 2, No. 3, pp. 169-173.

Teng, Yang D., Erin B. Lavik, Xianlu Qu, Kook I. Park, Jitka Ourednik, David Zurakowski, Robert Langer, and Evan Y. Snyder. Mar. 5, 2002. "Functional Recovery Following Traumatic Spinal Cord Injury Mediated by a Unique Polymer Scaffold Seeded with Neural Stem Cells." *Proceedings of the National Academy of Sciences of the United States of America*. vol. 99, No. 5, pp. 3024-3029.

Bradbury, Elizabeth J., Lawrence D. F. Moon, Reena J. Popat, Von R. King, Gavin S. Bennett, Preena N. Patel, James W. Fawcett, and Stephen B. McMahon. Apr. 11, 2002. "Chondroitinase ABC Promotes Functional Recovery After Spinal Cord Injury." *Nature*. vol. 416, pp. 636-640.

Hartgerink, Jeffrey D., Elia Beniash, and Samuel I. Stupp. Apr. 16, 2002. "Supramolecular Chemistry and Self-Assembly Special Feature: Peptide-Amphiphile Nanofibers: A Versatile Scaffold for the Preparation of Self-Assembling Materials." *Proceedings of the National Academy of Sciences of the United States of America*. vol. 99, No. 8, pp. 5133-5138.

Vauthey, Sylvain, Steve Santoso, Haiyan Gong, Nicki Watson, and Shuguang Zhang. Apr. 16, 2002. "Molecular Self-Assembly of Surfactant-like Peptides to Form Nanotubes and Nanovesicles." *Proceedings of the National Academy of Sciences of the United States of America*. vol. 99, No. 8, pp. 5355-5360.

Nowak, Andrew P., Victor Breedveld, Lisa Pakstis, Bulent Ozbas, David J. Pine, Darrin Pochan, and Timothy J. Deming. May 23, 2002. "Rapidly Recovering Hydrogel Scaffolds from Self-Assembling Diblock Copolypeptide Amphiphiles." *Nature*. vol. 417, pp. 424-428.

GrandPré, Tadzia, Shuxin Li, and Stephen M. Strittmatter. May 30, 2002. "Nogo-66 Receptor Antagonist Peptide Promotes Axonal Regeneration." *Nature*. vol. 417, pp. 547-551.

Storch, Alexander and Johannes Schwarz. May 2002. "Neural Stem Cells and Neurodegeneration." *Current Opinion in Investigational Drugs*. vol. 3, No. 5, pp. 774-781.

Lendlein, Andreas and Robert Langer. May 31, 2002. "Biodegradable, Elastic Shape-Memory Polymers for Potential Biomedical Applications." *Science*. vol. 296, pp. 1673-1676.

Qiu, Jin, Dongming Cai, Haining Dai, Marietta McAttee, Paul N. Hoffman, Barbara S. Bregman, and Marie T. Filbin. Jun. 13, 2002. "Spinal Axon Regeneration Induced by Elevation of Cyclic AMP." *Neuron*. vol. 34, pp. 895-903.

Catledge, Shane A., Marc D. Fries, Yogesh K. Vohra, William R. Lacefield, Jack E. Lemons, Shanna Woodard, and Ramakrishna Venugopalan. Jun.-Aug. 2002. "Nanostructured Ceramics for Biomedical Implants." *Journal of Nanoscience and Nanotechnology*. vol. 2, No. 3/4, pp. 293-312.

Alsberg, Eben, Kenneth W. Anderson, Amru Albeiruti, Jon A. Rowley, and David J. Mooney. Sep. 17, 2002. "Engineering Growing Tissues." *Proceedings of the National Academy of Sciences of the United States of America*. vol. 99, No. 19, pp. 12025-12030.

Kay, Sarina, Anil Thapa, Karen M. Haberstroh, and Thomas J. Webster. Oct. 2002. "Nanostructured Polymer/Nanophase Ceramic Composites Enhance Osteoblast and Chondrocyte Adhesion." *Tissue Engineering*. vol. 8, No. 5, pp. 753-761.

Blight, Andrew R. Nov. 2002. "Miracles and Molecules—Progress in Spinal Cord Repair." Nature Neuroscience Supplement. vol. 5, pp. 1051-1054.

Silva, G. A., C. Czeisler, K. L. Niece, E. Beniash, J. D. Hartgerink, J. A. Kessler, and S. I. Stupp. Nov. 2-7, 2002. "Development of Neural Progenitor Cells Encapsulated in a Peptide Amphiphile Substrate That is Induced to Self-Assemble Under Physiological Conditions." *Biosis*. Society for Neuroscience Abstract Viewer and Itinerary Planner—2002. Abstract No. 825.4. $32^{nd}$ Annual Meeting of the Society for Neuroscience; Orlando, Florida.

Chang, Hua, Chester W. Brown, and Martin M. Matzuk. Dec. 2002. "Genetic Analysis of the Mammalian Transforming Growth Factor-β Superfamily." *Endocrine Reviews*. vol. 23, No. 6, pp. 787-823.

Avrahami, Dorit and Yechiel Shai. 2002. "Conjugation of a Magainin Analogue with Lipophilic Acids Controls Hydrophobicity, Solution Assembly, and Cell Selectivity." *Biochemistry*. vol. 41, No. 7, pp. 2254-2263.

Busqué, Félix, Stephanie A. Hopkins, and Joseph P. Konopelski. 2002. "Progress Toward a Peptidomimetic of Laminin-Derived Pentapeptide YIGSR: Synthesis of the Unique Tricyclic Core Structure." *J. Org. Chem.* vol. 67, No. 17, pp. 6097-6103.

Canaple, Laurence, Annemie Rehor, and David Hunkeler. 2002. "Improving Cell Encapsulation Through Size Control." *J. Biomater. Sci. Polymer Edn.* vol. 13, No. 7, pp. 783-796.

Caplan, Michael R., Elissa M. Schwartzfarb, Shuguang Zhang, Roger D. Kamm, and Douglas A. Lauffenburger. 2002. "Control of Self-Assembling Oligopeptide Matrix Formation Through Systematic Variation of Amino Acid Sequence." *Biomaterials*. vol. 23, pp. 219-227.

Chen, Zhi Jiang, Yvonne Ughrin, and Joel M. Levine. 2002. "Inhibition of Axon Growth by Oligodendrocyte Precursor Cells." *Molecular and Cellular Neuroscience*. vol. 20, pp. 125-139.

Cornish, Toby, Darren W. Branch, Bruce C. Wheeler, and James T. Campanelli. 2002. "Microcontact Printing: A Versatile Technique for the Study of Synaptogenic Molecules." *Molecular and Cellular Neuroscience*. vol. 20, pp. 140-153.

Costa, Silvia, Thierry Planchenault, Cecile Charriere-Bertrand, Yann Mouchel, Christiane Fages, Sharon Juliano, Thierry Lefrançois, Georgia Barlovatz-Meimon, and Marcienne Tardy. 2002. "Astroglial Permissivity for Neuritic Outgrowth in Neuron-Astrocyte Cocultures Depends on Regulation of Laminin Bioavailability." *GLIA*. vol. 37, pp. 105-113.

Gariépy, Jean, Sandrine Rémy, Xiuguo Zhang, James R. Ballinger, Eleonora Bolewska-Pedyczak, Michael Rauth, and Stuart K. Bisland. 2002. "A Simple Two-Step Approach for Introducing a Protected Diaminedithiol Chelator During Solid-Phase Assembly of Peptides." *Bioconjugate Chem.* vol. 13, No. 3, pp. 679-684.

Glättli, Alice, Xavier Daura, Dieter Seebach, and Wilfred F. van Gunsteren. 2002. "Can One Derive the Confrontational Preference of a β-Peptide from its CD Spectrum?" *Journal of the American Chemical Society.* vol. 124, No. 44, pp. 12972-12978.

Gutwein, Luke G. and Thomas J. Webster. 2002. "Osteoblast and Chrondrocyte Proliferation in the Presence of Alumina and Titania Nanoparticles." *Journal of Nanoparticle Research.* vol. 4, pp. 231-238.

Huang, Ning-Ping, Gabor Csucs, Kazunori Emoto, Yukio Nagasaki, Kazunori Kataoka, Marcus Textor, and Nicholas D. Spencer. 2002. "Covalent Attachment of Novel Poly(ethylene glycol)—Poly(DL-lactic acid) Copolymeric Micelles to $TiO_2$ Surfaces." *Langmuir.* vol. 18, No. 1, pp. 252-258.

Issac, Roy and Jean Chmielewski. 2002. "Approaching Exponential Growth with a Self-Replicating Peptide." *Journal of the American Chemical Society.* vol. 124, No. 24, pp. 6808-6809.

Joshi, Mital and Michael G. Fehlings. 2002. "Development and Characterization of a Novel, Graded Model of Clip Compressive Spinal Cord Injury in the Mouse: Part 1. Clip Design, Behavioral Outcomes, and Histopathology." *Journal of Neurotrauma.* vol. 19, No. 2, pp. 175-190.

Joshi, Mital and Michael G. Fehlings. 2002. "Development and Characterization of a Novel, Graded Model of Clip Compressive Spinal Cord Injury in the Mouse: Part 2. Quantitative Neuroanatomical Assessment and Analysis of the Relationships Between Axonal Tracts, Residual Tissue, and Locomotor Recovery." *Journal of Neurotrauma.* vol. 19, No. 2, pp. 191-203.

Kruger, Ryan G., Patrick Dostal, and Dewey G. McCafferty. 2002. "An Economical and Preparative Orthogonal Solid Phase Synthesis of Fluorescein and Rhodamine Derivatized Peptides: FRET Substrates for the *Staphylococcus aureus* Sortase SrtA Transpeptidase Reaction." *Chem. Commun.* pp. 2092-2093.

Lauer, L., A. Vogt, C. K. Yeung, W. Knoll, and A. Offenhäusser. 2002. "Electrophysiological Recordings of Patterned Rat Brain Stem Slice Neurons." *Biomaterials.* vol. 23, pp. 3123-3130.

Lavik, Erin, Yang D. Teng, Evan Snyder, and Robert Langer. 2002. "Speeding Neural Stem Cells on Scaffolds of PGA, PLA, and Their Copolymers." *Methods in Molecular Biology: Neural Stem Cells: Methods and Protocols.* vol. 198, pp. 89-97.

Marini, Davide M., Wonmuk Hwang, Douglas A. Lauffenburger, Shuguang Zhang, and Roger D. Kamm. 2002. "Left-Handed Helical Ribbon Intermediates in the Self-Assembly of a β-Sheet Peptide." *Nano Letters.* vol. 2, No. 4, pp. 295-299.

Ohsaki, Mio, Tatsuya Okuda, Akihiro Wada, Toshiya Hirayama, Takuro Niidome, and Haruhiko Aoyagi. 2002. "In Vitro Gene Transfection Using Dendritic Poly(L-lysine)." *Bioconjugate Chem.* vol. 13, No. 3, pp. 510-517.

Okano, Hideyuki. 2002. "Stem Cell Biology of the Central Nervous System." *Journal of Neuroscience Research.* vol. 69, pp. 698-707.

Parmar, Malin, Charlotta Skogh, Anders Björklund, and Kenneth Campbell. 2002. "Regional Specification of Neurosphere Cultures Derived from Subregions of the Embryonic Telencephalon." *Molecular and Cellular Neuroscience.* vol. 21, pp. 645-656.

Porter, A. E., L. W. Hobbs, V. Benezra Rosen, and M. Spector. 2002. "The Ultrastructure of the Plasma-Sprayed Hydroxyapatite-bone Interface Predisposing to Bone Bonding." *Biomaterials.* vol. 23, pp. 725-733.

Rodger, Alison, Jascindra Rajendra, Rachel Marrington, Malin Ardhammar, Bengt Norden, Jonathan D. Hirst, Andrew T. B. Gilbert, Timothy R. Dafforn, David J. Halsall, Cheryl A. Woolhead, Colin Robinson, Teresa J. T. Pinheiro, Jurate Kazlauskaite, Mark Seymour, Niuvis Perez, and Michael J. Hannon. 2002. "Flow Oriented Linear Dichroism to Probe Protein Orientation in Membrane Environments." *Phys. Chem. Chem. Phys.* vol. 4, pp. 4051-4057.

Rowley, Jon A. and David J. Mooney. 2002. "Alginate Type and RGD Density Control Myoblast Phenotype." *Journal of Biomedical Materials Research.* vol. 60, pp. 217-223.

Santoso, Steve S., Sylvain Vauthey, and Shuguang Zhang. 2002. "Structures, Function and Applications of Amphiphilic Peptides." *Current Opinion in Colloid & Interface Science.* vol. 7, pp. 262-266.

Shih, Sheng-Ming, Wei-Fang Su, Yuh-Jiuan Lin, Cen-Shawn Wu, and Chii-Dong Chen. 2002. "Two-Dimensional Arrays of Self-Assembled Gold and Sulfur-Containing Fullerene Nanoparticles." *Langmuir.* vol. 18, No. 8, pp. 3332-3335.

Thiébaud, Pierre, Lars Lauer, Wolfgang Knoll, and Andreas Offenhäuser. 2002. "PDMS Device for Patterned Application of Microfluids to Neuronal Cells Arranged by Microcontact Printing." *Biosensors & Bioelectronics.* vol. 17, pp. 87-93.

Tryoen-Tóth, Petra, Dominique Vautier, Youssef Haikel, Jean-Claude Voegel, Pierre Schaaf, Johanna Chluba, and Joëlle Ogier. 2002. "Viability, Adhesion, and Bone Phenotype of Osteoblast-like Cells on Polyelectrolyte Multilayer Films." *Journal of Biomedical Materials Research.* vol. 60, pp. 657-667.

Wong, Michael S., Jennifer N. Cha, Kyoung-Shin Choi, Timothy J. Deming, and Galen D. Stucky. 2002. "Assembly of Nanoparticles into Hollow Spheres Using Block Copolypeptides." *Nano Letters.* vol. 2, No. 6, pp. 583-587.

Yamada, Masanori, Yuichi Kadoya, Shingo Kasai, Kozue Kato, Mayumi Mochizuki, Norio Nishi, Nobuhisa Watanabe, Hynda K. Kleinman, Yoshihiko Yamada, and Motoyoshi Nomizu. 2002. "Ile-Lys-Val-Ala-Val (IKVAV)-Containing Laminin α1 Chain Peptides Form Amyloid-like Fibrils." *FEBS Letters.* vol. 530, pp. 48-52.

Young, Wise. 2002. "Spinal Cord Contusion Models." *Progress in Brain Research.* vol. 137, pp. 231-255.

Bruggeman, Holger, Sebastian Baumer, Wolfgang Florian Fricke, Arnim Wiezer, Heiko Liesegang, Iwona Decker, Christina Herzberg, Rosa Martinez-Arias, Rainer Merkl, Anke Benne, and Gerhard Gottschalk. Feb. 4, 2003. "The Genome Sequence of *Clostridium tetani*, the Causative Agent of Tetanus Disease." *PNAS.* vol. 100, No. 3, pp. 1316-1321.

McGregor, Clare-Louise, Lu Chen, Neil C. Pomroy, Peter Hwang, Sandy Go, Avijit Chakrabartty, and Gilbert G. Privé. Feb. 2003. "Lipopeptide Detergents Designed for the Structural Study of Membrane Proteins." *Nature Biotechnology.* vol. 21, pp. 171-176.

Lutolf, Matthias P., Franz E. Weber, Hugo G. Schmoekel, Jason C. Schense, Thomas Kohler, Ralph Müller, and Jeffrey A. Hubbell. May 2003. "Repair of Bone Defects Using Synthetic Mimetics of Collagenous Extracellular Matrices." *Nature Biotechnology.* vol. 21, pp. 513-518.

Shaw, Derek and Molly S. Shoichet. May 2003. "Toward Spinal Cord Injury Repair Strategies: Peptide Surface Modification of Expanded Poly(Tetrafluoroethylene) Fibers for Guided Neurite Outgrowth in Vitro." *The Journal of Craniofacial Surgery.* vol. 14, No. 3, pp. 308-316.

Silva, G. A., K. L. Kehl, K. L. Niece, and S. I. Stupp. May 4, 2003. "Nanoengineered Peptide Amphiphile Network for Photoreceptor Replacement in Degenerative Retinal Disorders." Investigative Ophthalmology & Visual Science. Abstract No. 492 from Annual Meeting of the Association for Research in Vision and Opthalmology.

Cheng, Hongwei, Wei Jiang, Frank M. Phillips, Rex C. Haydon, Ying Peng, Lan Zhou, Hue H. Luu, Naili An, Benjamin Breyer, Pantila Vanichakarn, Jan Paul Szatkowski, Jae Yoon Park, and Tong-Chuan He. Aug. 2003. "Osteogenic Activity of the Fourteen Types of Human Bone Morphogenetic Proteins (BMPs)." *The Journal of Bone & Joint Surgery.* vol. 85-A, No. 8, pp. 1544-1552, 141.

Leng, J., S. U. Egelhaaf, and M. E. Cates. Sep. 2003. "Kinetics of the Micelle-to-Vesicle Transition: Aqueous Lecithin-Bile Salt Mixtures." *Biophysical Journal.* vol. 85, No. 3, pp. 1624-1646.

Arinzeh, Treena Livingston, Susan J. Peter, Michael P. Archambault, Christian van den Bos, Steve Gordon, Karl Kraus, Alan Smith, and Sudha Kadiyala. Oct. 2003. "Allogeneic Mesenchymal Stem Cells Regenerate Bone in a Critical-Sized Canine Segmental Defect." *The Journal of Bone & Joint Surgery.* vol. 85-A, No. 10, pp. 1927-1935.

Zhang, Shuguang. Oct. 2003. "Fabrication of Novel Biomaterials Through Molecular Self-Assembly." *Nature Biotechnology.* vol. 21, No. 10, pp. 1171-1178.

Aggeli, Amalia, Mark Bell, Lisa M. Carrick, Colin W. G. Fishwick, Richard Harding, Peter J. Mawer, Sheena E. Radford, Andrew E. Strong, and Neville Boden. 2003. "pH as a Trigger of Peptide β-Sheet Self-Assembly and Reversible Switching Between Nematic and Isotropic Phases." *Journal of the American Chemical Society*. vol. 125, No. 32, pp. 9619-9628.

Alsina, Jordi and Fernando Albericio. 2003. "Solid-Phase Synthesis of C-Terminal Modified Peptides." *Biopolymers (Peptide Science)*. vol. 71, pp. 454-477.

Anthony, Shawn G. 2003. "Injectable Biomaterials for Bone Tissue Engineering."

Boontheekul, Tanyarut and David J. Mooney. 2003. "Protein-Based Signaling Systems in Tissue Engineering." *Current Opinion in Biotechnology*. vol. 14, pp. 559-565.

Brandenburg, Klaus, Frauke Wagner, Mareike Muller, Holger Heine, Jorg Andra, Michel H. J. Koch, Ulrich Zahringer, and Ulrich Seydel. 2003. "Physicochemical Characterization and Biological Activity of a Glycoglycerolipid from Mycoplasma fermentans." *Eur. J. Biochem*. vol. 270, pp. 3271-3279.

Czeisler, C., V. M. Tysseling-Mattiace, G. A. Silva, S. I. Stupp, and J. A. Kessler. 2003. "Behavioral Improvement and Increased Survival Rate after Treatment with a Self Assembling Gel in a Rat Model of Spinal Cord Injury." 2003 Abstract Viewer/Itinerary Planner. Program No. 245.22. Washington, DC: Society for Neuroscience. Printed Feb. 5, 2007. Page 1. http://sfn.scholarone.com/itin2003/main.html?new_page_id=126&abstract_id=1554....

Fauza, Dario O. 2003. "Tissue Engineering: Current State of Clinical Application." *Current Opinion in Pediatrics*. vol. 15, pp. 267-271.

Ganesh, S. and R. Jayakumar. 2003. "Structural Transitions Involved in a Novel Amyloid-Like β-Sheet Assemblage of Tripeptide Derivatives." *Biopolymers*. vol. 70, pp. 336-345.

Ganesh, S., S. Prakash, and R. Jayakumar. 2003. "Spectroscopic Investigation on Gel-Forming β-Sheet Assemblage of Peptide Derivatives." *Biopolymers*. vol. 70, pp. 346-354.

Gergely, C. S., P. Bar Yosef, R. Govrin-Lippman, F. Cuisinier, and H. Füredi-Milhofer. 2003. "The Deposition of Calcium Phosphates Within Polyelectrolyte Multilayer Films." *Key Engineering Materials*. vols. 240-242 (Bioceramics), pp. 287-290.

Goeden-Wood, Nichole L., Jay D. Keasling, and Susan J. Muller. 2003. "Self-Assembly of a Designed Protein Polymer into β-Sheet Fibrils and Responsive Gels." *Macromolecules*. vol. 36, No. 8, pp. 2932-2938.

Ishihara, Masayuki, Kiyohaya Obara, Toshiaki Ishizuka, Masanori Fujita, Masato Sato, Kazunori Masuoka, Yoshio Saito, Hirofumi Yura, Takemi Matsui, Hidemi Hattori, Makoto Kikuchi, and Akira Kurita. 2003. "Controlled Release of Fibroblast Growth Factors and Heparin from Photocrosslinked Chitosan Hydrogels and Subsequent Effect on in Vivo Vascularization." *Journal of Biomedical Materials Research*. vol. 64A, pp. 551-559.

Malkar, Navdeep B., Janelle L. Lauer-Fields, Darius Juska, and Gregg B. Fields. 2003. "Characterization of Peptide-Amphiphiles Possessing Cellular Activation Sequences." *Biomacromolecules*. vol. 4, No. 3, pp. 518-528.

Niece, Krista L., Jeffrey D. Hartgerink, Jack J. J. M. Donners, and Samuel I. Stupp. 2003. "Self-Assembly Combining Two Bioactive Peptide-Amphiphile Molecules into Nanofibers by Electrostatic Attraction." *Journal of the American Chemical Society*. vol. 125, No. 24, pp. 7146-7147.

Pavlov, Georges, Stéphanie Finet, Karine Tatarenko, Evgueniya Korneeva, and Christine Ebel. 2003. "Conformation of Heparin Studied with Macromolecular Hydrodynamic Methods and X-ray Scattering." *Eur. Biophys. J.* vol. 32, pp. 437-449.

Schmidt, Christine E. and Jennie Baier Leach. 2003. "Neural Tissue Engineering: Strategies for Repair and Regeneration." *Annu. Rev. Biomed. Eng.* vol. 5, pp. 293-347.

Steward, Oswald, Binhai Zheng, and Marc Tessier-Lavigne. 2003. "False Resurrections: Distinguishing Regenerated from Spared Axons in the Injured Central Nervous System." *The Journal of Comparative Neurology*. vol. 459, pp. 1-8.

t' Hart, Bert A. and Sandra Amor. 2003. "The Use of Animal Models to Investigate the Pathogenesis of Neuroinflammatory Disorders of the Central Nervous System." Current Opinion in Neurology. vol. 16, pp. 375-383.

Wu, Sufan, Yoshihisa Suzuki, Yoko Ejiri, Toru Noda, Hongliang Bai, Masaaki Kitada, Kazuya Kataoka, Masayoshi Ohta, Hirotomi Chou, and Chizuka Ide. 2003. "Bone Marrow Stromal Cells Enhance Differentiation of Cocultured Neurosphere Cells and Promote Regeneration of Injured Spinal Cord." *Journal of Neuroscience Research*. vol. 72, pp. 343-351.

Yamada, Norihiro, Tsukasa Komatsu, Hirotsugu Yoshinaga, Kayo Yoshizawa, Susumu Edo, and Masashi Kunitake. 2003. "Self-Supporting Elastic Film without Covalent Linkages as a Hierarchically Integrated β-Sheet Assembly." *Angew. Chem. Int. Ed.* vol. 42, pp. 5496-5499.

Zhang, Yan, Hongwei Gu, Zhimou Yang, and Bing Xu. 2003. "Supramolecular Hydrogels Respond to Ligand-Receptor Interaction." *Journal of the American Chemical Society*. vol. 125, No. 45, pp. 13680-13681.

Hirano, Yoshiaki and David J. Mooney. Jan. 5, 2004. "Peptide and Protein Presenting Materials for Tissue Engineering." *Advanced Materials*. vol. 16, No. 1, pp. 17-25.

Silva, Gabriel A., Catherine Czeisler, Krista L. Niece, Elia Beniash, Daniel A. Harrington, John A. Kessler, and Samuel I. Stupp. Feb. 27, 2004. "Selective Differentiation of Neural Progenitor Cells by High-Epitope Density Nanofibers." *Science*. vol. 303, pp. 1352-1355.

Faulkner, Jill R., Julia E. Herrmann, Michael J. Woo, Keith E. Tansey, Ngan B. Doan, and Michael V. Sofroniew. Mar. 3, 2004. "Reactive Astrocytes Protect Tissue and Preserve Function after Spinal Cord Injury." *The Journal of Neuroscience*. vol. 24, No. 9, pp. 2143-2155.

Cao, Renhai, Anna Eriksson, Hajime Kubo, Kari Alitalo, Yihai Cao, Johan Thyberg. Mar. 19, 2004. "Comparative Evaluation of FGF-2-, VEGF-A-, and VEGF-C-Induced Angiogenesis, Lymphangiogenesis, Vascular Fenestrations, and Permeability." *Circulation Research*. vol. 94, pp. 664-670.

Anthony, Shawn G. Mar. 28-Apr. 1, 2004. "Self-Assembling Nanofiber Matrix for Bone Regeneration." *The 227th ACS National Meeting*. Anaheim, CA.

Donners, Jack J. J. M. Mar. 28-Apr. 1, 2004. "Growth Factor Binding Self-Assembling Nanofiber Networks for Tissue Regeneration." *The 227th ACS National Meeting*. Anaheim, CA.

Nikulina Elena, J. Lille Tidwell, Hai Ning Dai, Barbara S. Bregman, and Marie T. Filbin. Jun. 8, 2004. "The Phosphodiesterase Inhibitor Rolipram Delivered after a Spinal Cord Lesion Promotes Axonal Regeneration and Functional Recovery." *Proceedings of the National Academy of Sciences of the United States of America*. vol. 101, No. 23, pp. 8786-8790.

Pearse, Damien D., Francisco C. Pereira, Alexander E. Marcillo, Margaret L. Bates, Yerko A. Berrocal, Marie T. Filbin, and Mary Bartlett Bunge. Jun. 2004. "cAMP and Schwann Cells Promote Axonal Growth and Functional Recovery After Spinal Cord Injury." *Nature Medicine*. vol. 10, No. 6, pp. 610-616.

Lu, Paul, Hong Yang, Leonard L. Jones, Marie T. Filbin, and Mark H. Tuszynski. Jul. 14, 2004. "Combinatorial Therapy with Neurotrophins and cAMP Promotes Axonal Regeneration beyond Sites of Spinal Cord Injury." *The Journal of Neuroscience*. vol. 24, No. 28, pp. 6402-6409.

Lee, K. W., J. J. Yoon, J. H. Lee, S. Y. Kim, H. J. Jung, S. J. Kim, J. W. Joh, H. H. Lee, D. S. Lee, and S. K. Lee. 2004. "Sustained Release of Vascular Endothelial Growth Factor From Calcium-Induced Alginate Hydrogels Reinforced by Heparin and Chitosan." *Transplantation Proceedings*. vol. 36, pp. 2464-2465.

Matsumura, Sachiko, Shinobu Uemura, and Hisakazu Mihara. 2004. "Fabrication of Nanofibers with Uniform Morphology by Self-Assembly of Designed Peptides." *Chem. Eur. J.* vol. 10, pp. 2789-2794.

Ohmori, Hideya, Yasumitsu Sato, and Akiyoshi Namiki. 2004. "The Anticonvulsant Action of Propofol on Epileptiform Activity in Rat Hippocampal Slices." *Anesth. Analg.* vol. 99, pp. 1095-1101.

Shahraki, Ali and Trevor W. Stone. 2004. "Blockade of Presynaptic Adenosine A1 Receptor Responses by Nitric Oxide and Superoxide in Rat Hippocampus." *European Journal of Neuroscience*. vol. 20, pp. 719-728.

Sieminski, A. L., R. P. Hebbel, and K. J. Gooch. 2004. "The Relative Magnitudes of Endothelial Force Generation and Matrix Stiffness Modulate Capillary Morphogenesis in Vitro." *Experimental Cell Research*. vol. 297, pp. 574-584.

Sone, Eli D. and Samuel I. Stupp. 2004. "Semiconductor-Encapsulated Peptide-Amphiphile Nanofibers." *Journal of the American Chemical Society*. vol. 126, No. 40, pp. 12756-12757.

Smith, L. A. and P. X. Ma. 2004. "Nano-Fibrous Scaffolds for Tissue Engineering." *Colloids and Surfaces. B: Biointerfaces*. vol. 39, pp. 125-131.

Tsonchev, Stefan, George C. Schatz, and Mark A. Ratner. 2004. "Electrostatically-Directed Self-Assembly of Cylindrical Peptide Amphiphile Nanostructures." *J Phys. Chem. B*. vol. 108, No. 26, pp. 8817-8822.

Tsonchev, Stefan, Alessandro Troisi, George C. Schatz, and Mark A. Ratner. 2004. "All-Atom Numerical Studies of Self-Assembly of Zwitterionic Peptide Amphiphiles." *J. Phys. Chem. B*. vol. 108, No. 39, pp. 15278-15284.

Tsonchev, Stefan, Alessandro Troisi, George C. Schatz, and Mark A. Ratner. 2004. "On the Structure and Stability of Self-Assembled Zwitterionic Peptide Amphiphiles: A Theoretical Study." *Nano Letters*. vol. 4, No. 3, pp. 427-431.

Vandermeulen, Guido W. M. and Harm-Anton Klok. 2004. "Peptide/Protein Hybrid Materials: Enhanced Control of Structure and Improved Performance through Conjugation of Biological and Synthetic Polymers." *Macromolecular Bioscience*. vol. 4, pp. 383-398.

Wang, Lin-Fa and Meng Yu. 2004. "Epitope Identification and Discovery Using Phage Display Libraries: Applications in Vaccine Development and Diagnostics." *Current Drug Targets*. vol. 5, No. 1, pp. 1-15.

Sayle, Roger. Printed Nov. 9, 2005. "Physiological Ionization and pKa Prediction." http://www.daylight.com/meetings/emug00/Sayle/pkapredict.html. pp. 1-13.

Arnold, Michael S., Mustafa O. Guler, Mark C. Hersam, and Samuel I. Stupp. 2005. "Encapsulation of Carbon Nanotubes by Self-Assembling Peptide Amphiphiles." *Langmuir*. vol. 21, No. 10, pp. 4705-4709.

Behanna, Heather A., Jack J. J. M. Donners, Alex C. Gordon, and Samuel I. Stupp. 2005. "Coassembly of Amphiphiles with Opposite Peptide Polarities into Nanofibers." *Journal of the American Chemical Society*. vol. 127, No. 4, pp. 1193-1200.

Beniash, Elia, Jeffery D. Hartgerink, Hannah Storrie, John C. Stendahl, and Samuel I. Stupp. 2005. "Self-Assembling Peptide Amphiphile Nanofiber Matrices for Cell Entrapment." *Acta Biomaterialia*. vol. 1, pp. 387-397.

Bitton, Ronit, Judith Schmidt, Markus Biesalski, Raymond Tu, Matthew Tirrell, and Havazelet Bianco-Peled. 2005. "Self-Assembly of Model DNA-Binding Peptide Amphiphiles." *Langmuir*. vol. 21, No. 25, pp. 11888-11895.

Bull, Steve R., Mustafa O. Guler, Rafael E. Bras, Thomas J. Meade, and Samuel I. Stupp. 2005. "Self-Assembled Peptide Amphiphile Nanofibers Conjugated to MRI Contrast Agents." *Nano Letters*. vol. 5, No. 1, pp. 1-4.

Bull, Steve R., Mustafa O. Guler, Rafael E. Bras, Palamadai N. Venkatasubramanian, Samuel I. Stupp, and Thomas J. Meade. 2005. "Magnetic Resonance Imaging of Self-Assembled Biomaterial Scaffolds." *Bioconjugate Chem*. vol. 16, No. 6, pp. 1343-1348.

de Loos, Maaike, Ben L. Feringa, and Jan H. van Esch. 2005. "Design and Application of Self-Assembled Low Molecular Weight Hydrogels." *Eur. J Org. Chem*. pp. 3615-3631.

Guler, Mustafa O., Randal C. Claussen, and Samuel I. Stupp. 2005. "Encapsulation of Pyrene Within Self-Assembled Peptide Amphiphile Nanofibers." *Journal of Materials Chemistry*. vol. 15, pp. 4507-4512.

Guler, Mustafa O., Jonathan K. Pokorski, Daniel H. Appella, and Samuel I. Supp. 2005. "Enhanced Oligonucleotide Binding to Self-Assembled Nanofibers." *Bioconjugate Chem*. vol. 16, No. 3, pp. 501-503.

Guler, Mustafa O., Stephen Soukasene, James F. Hulvat, and Samuel I. Stupp. 2005. "Presentation and Recognition of Biotin on Nanofibers Formed by Branched Peptide Amphiphiles." *Nano Letters*. vol. 5, No. 2, pp. 249-252.

Jun, Ho-Wook, Virany Yuwono, Sergey E. Paramonov, and Jeffrey D. Hartgerink. 2005. "Enzyme-Mediated Degradation of Peptide-Amphiphile Nanofiber Networks." *Adv. Mater*. vol. 17, pp. 2612-2617.

Knake, Rene, Amir W. Fahmi, Syed A. M. Tofail, Jason Clohessy, Miroslav Mihov, and Vincent J. Cunnane. 2005. "Electrochemical Nucleation of Gold Nanoparticles in a Polymer Film at a Liquid-Liquid Interface." *Langmuir*. vol. 21, No. 3, pp. 1001-1008.

Silva, Gabriel A. 2005. "Nanotechnology Approaches for the Regeneration and Neuroprotection of the Central Nervous System." *Surgical Neurology*. vol. 63, pp. 301-306.

Silva, Gabriel A. 2005. "Small Neuroscience: The Nanostructure of the Central Nervous System and Emerging Nanotechnology Applications." *Current Nanoscience*. vol. 1, No. 3, pp. 225-236.

Solis., F. J., S. I. Stupp, and M. Olvera de la Cruz. 2005. "Charge Induced Pattern Formation on Surfaces: Segregation in Cylindrical Micelles of Cationic-Anionic Peptide-Amphiphiles." *The Journal of Chemical Physics*. vol. 122, No. 5, 054905-1-054905-9.

Tovar, John D., Randal C. Claussen, and Samuel I. Stupp. 2005. "Probing the Interior of Peptide Amphiphile Supramolecular Aggregates." *Journal of the American Chemical Society*. vol. 127, No. 20, pp. 7337-7345.

Loudon, M. "Amino Acid Structures at Physiological pH." Printed Jun. 5, 2006. www.brynmawr.edu/Acads/Chem/mnerzsto/amino_acids.htm, amino_acids_2.gif, and amino_acids.htm.

Hosseinkhani, Hossein, Mohsen Hosseinkhani, and Hisatoshi Kobayashi. Jul. 2006. "Design of Tissue-Engineered Nanoscaffold Through Self-Assembly of Peptide Amphiphile." *Journal of Bioactive and Compatible Polymers*. vol. 21, No. 4, pp. 277-296.

Engler, Adam J., Shamik Sen, H. Lee Sweeney, and Dennis E. Discher. Aug. 25, 2006. "Matrix Elasticity Directs Stem Cell Lineage Specification." *Cell*. vol. 126, pp. 677-689.

Hoke, Ahmet. Aug. 2006. "Mechanisms of Disease: What Factors Limit the Success of Peripheral Nerve Regeneration in Humans?" *Nature Clinical Practice Neurology*. vol. 2, No. 8, pp. 448-454.

Brunsveld, L., J. Kuhlmann, and H. Waldmann. 2006. "Synthesis of Palmitoylated Ras-Peptides and—Proteins." *Methods*. vol. 40, pp. 151-165.

Elgersma, Ronald C., Tania Meijneke, Remco de Jong, Arwin J. Brouwer, George Posthuma, Dirk T. S. Rijkers, and Rob M. J. Liskamp. 2006. "Synthesis and Structural Investigations of N-alkylated β-peptidosulfonamide-peptide Hybrids of the Amyloidogenic Amylin(20-29) Sequence: Implications of Supramolecular Folding for the Design of Peptide-Based Bionanomaterials." *Organic & Biomolecular Chemistry*. vol. 4, pp. 3587-3597.

Guler, Mustafa O., Lorraine Hsu, Stephen Soukasene, Daniel A. Harrington, James F. Hulvat, and Samuel I. Stupp. 2006. "Presentation of RGDS Epitopes on Self-Assembled Nanofibers of Branched Peptide Amphiphiles." *Biomacromolecules*. vol. 7, No. 6, pp. 1855-1863.

Harrington, Daniel A., Earl Y. Cheng, Mustafa O. Guler, Leslie K. Lee, Jena L. Donovan, Randal C. Claussen, and Samuel I. Stupp. 2006. "Branched Peptide-Amphiphiles as Self-Assembling Coatings for Tissue Engineering Scaffolds." *Journal of Biomedical Materials Research Part A*. pp. 157-167.

Hosseinkhani, Hossein, Mohsen Hosseinkhani, Ali Khademhossein, Hisatoshi Kobayashi, and Yasuhiko Tabata. 2006. "Enhanced Angiogenesis Through Controlled Release of Basic Fibroblast Growth Factor from Peptide Amphiphile for Tissue Regeneration." *Biomaterials*. vol. 27, pp. 5836-5844.

Kokkoli, Efrosini, Anastasia Mardilovich, Alison Wedekind, Emilie L. Rexeisen, Ashish Garg, and Jennifer A. Craig. 2006. "Self-Assembly and Applications of Biomimetic and Bioactive Peptide-Amphiphiles." *Soft Matter*. vol. 2, pp. 1015-1024.

Mardilovich, Anastasia, Jennifer A. Craig, Matthew Q. McCammon, Ashish Garg, and Efrosini Kokkoli. 2006. "Design of a Novel Fibronectin-Mimetic Peptide-Amphiphile for Functionalized Biomaterials." *Langmuir*. vol. 22, No. 7, pp. 3259-3264.

Paramonov, Sergey E., Ho-Wook Jun, and Jeffrey D. Hartgerink. 2006. "Self-Assembly of Peptide-Amphiphile Nanofibers: The Roles of Hydrogen Bonding and Amphiphilic Packing." *Journal of the American Chemical Society*. vol. 128, No. 22, pp. 7291-7298.

Rajangam, Kanya, Heather A. Behanna, Michael J. Hui, Xiaoqiang Han, James F. Hulvat, Jon W. Lomasney, and Samuel I. Stupp. 2006. "Heparin Binding Nanostructures to Promote Growth of Blood Vessels." *Nano Letters*. vol. 6, No. 9, pp. 2086-2090.

Reches, Meital and Ehud Gazit. 2006. "Molecular Self-Assembly of Peptide Nanostructures: Mechanism of Association and Potential Uses." *Current Nanoscience*. vol. 2, No. 2, pp. 105-111.

Stendahl, John C., Mukti S. Rao, Mustafa O. Guler, and Samuel I. Stupp. 2006. "Intermolecular Forces in the Self-Assembly of Peptide Amphiphile Nanofibers." *Advanced Functional Materials*. vol. 16, pp. 499-508.

"AccessScience Search Results. Amphiphile." Accessed online May 7, 2007. http://www.accessscience.com/search/asearch? location=titlestext&newSearch=1&pubpriv=private&categories= dictionary&categval=dictionary&text=amphiphile. McGraw-Hill Encyclopedia of Science & Technology Online.

Behanna, Heather A., Kanya Rajangam, and Samuel I. Stupp. 2007. "Modulation of Fluorescence Through Coassembly of Molecules in Organic Nanostructures." *Journal of the American Chemical Society*. vol. 129, No. 2, pp. 321-327.

Meijer, Joris T., Marjolijn Roeters, Valentina Viola, Dennis W. P. M. Löwik, Gert Vriend, and Jan C. M. van Hest. 2007. "Stabilization of Peptide Fibrils by Hydrophobic Interaction." *Langmuir*. vol. 23, No. 4, pp. 2058-2063.

The LabRatcom. 2007, updated. Hank's Buffered Salt Solution (HBSS) Recipe. http://www.thelabrat.com/protocolsHanks.shtml. Printed Jan. 19, 2007. pp. 1-2.

Invitrogen. Printed Jan. 22, 2008. "Dulbecco's Modified Eagle Medium (D-MEM) (1X) Liquid (High Glucose)." http://www.invitrogen.com/content.cfm?pageId=95&fuseaction=MediaForm.dsp_mediaForm&productId....

Uniprot entry for Q899Z6. Printed Mar. 14, 2008. http://www.pir.uniprot.org/cgi-bin/upEntry?id=Q899Z6_CLOTE. 3 pages.

Nakaoka, Takashi, Koichi Gonda, Teruhiko Ogita, Yoko Otawara-Hamamoto, Fujiko Okabe, Yuji Kira, Kiyonori Harii, Kohei Miyazono, Yoh Takuwa, and Toshiro Fujita. Dec. 1997. "Inhibition of Rat Vascular Smooth Muscle Proliferation In Vitro and In Vivo by Bone Morphogenetic Protein-2." J. Clin. Invest. vol. 100, No. 11, pp. 2824-2832.

Sampson, Wayne R., Heather Patsiouras, and Nicholas J. Ede. 1999. "The Synthesis of 'Difficult' Peptides Using 2-Hydroxy-4-Methoxybenzyl or Pseudoproline Amino Acid Building Blocks: a Comparative Study." Journal of Peptide Science. vol. 5, pp. 403-409.

Groeneveld, E. H. J. and E. H. Burger 2000. "Bone Morphogenetic Proteins in Human Bone Regeneration." European Journal of Endocrinology. vol. 142, pp. 9-21.

Martin, Ivan, R. Suetterlin, W. Baschong, M. Heberer, G. Vunjak-Novakovic, and L. E. Freed. 2001. "Enhanced Cartilage Tissue Engineering by Sequential Exposure of Chondrocytes to FGF-2 During 2D Expansion and BMP-2 During 3D Cultivation." Journal of Cellular Biochemistry. vol. 83, pp. 121-128.

Löwik, Dennis W. P. M., Jeffrey G. Linhardt, P. J. Hans M. Adams, and Jan C. M. van Hest. 2003. "Non-Covalent Stabilization of a β-Hairpin Peptide into Liposomes." Org. Biomol. Chem. vol. 1, pp. 1827-1829.

Oteiza, Patricia I., Gerardo G. Mackenzie, and Sandra V. Verstraeten. 2004. "Metals in Neurodegeneration: Involvement of Oxidants and Oxidant-Sensitive Transcription Factors." Molecular Aspects of Medicine. vol. 25, pp. 103-115.

Shen, Qin, Susan K. Goderie, Li Jin, Nithin Karanth, Yu Sun, Natalia Abramova, Peter Vincent, Kevin Pumiglia, and Sally Temple. May 28, 2004. Science. vol. 304, pp. 1338-1340.

Jun, Ho-Wook, Virany Yuwono, Sergey E. Paramonov, and Jeffrey D. Hartgerink. 2005. "Enzyme-Mediated Degradation of Peptide-Amphiphile Nanofiber Networks." Advanced Materials. vol. 17, pp. 2612-2617.

Kirkham, J., A. Firth, D. Vernals, N. Boden, C. Robinson, R. C. Shore, S. J. Brookes, and A. Aggeli. 2007. "Self-Assembling Peptide Scaffolds Promote Enamel Remineralization." J. Dent. Res. vol. 86, No. 5, pp. 426-430.

Yang, Zhengqin, Sufen Yang, Steven Y. Qian, Jau-Shyong Hong, Maria B. Kadiiska, Raymond W. Tennant, Michael P. Waalkes, and Jie Liu. 2007. "Cadmium-Induced Toxicity in Rat Primary Mid-brain Neuroglia Cultures: Role of Oxidative Stress from Microglia." Toxicological Sciences. vol. 98, No. 2, pp. 488-494.

Stryker, Lori. 2008. "Titanium Dioxide: Toxic or Safe?" The Organic Make-up Company Inc. www.organicmakeup.ca/ca/titaniumdioxide.asp. 4 pages. Printed Aug. 25, 2010.

Xia, Qing, Xudong Feng, Haifeng Huang, Lingyan Du, Xiaoda Yang, and Kui Wang. Dec. 20, 2010 (Accepted date). "Gadolinium-Induced Oxidative Stress Triggers Endoplasmic Reticulum Stress in Rat Cortical Neurons." Accepted Article for Journal of Neurochemistry. 23 pages.

\* cited by examiner

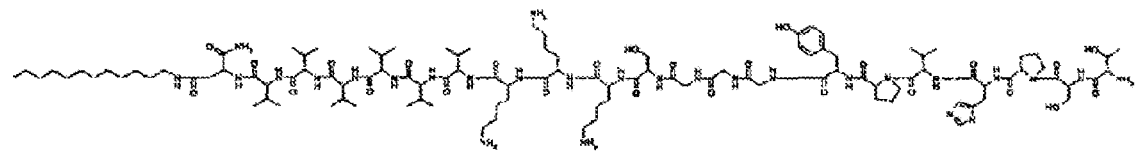
BMP-2 binding peptide amphiphile
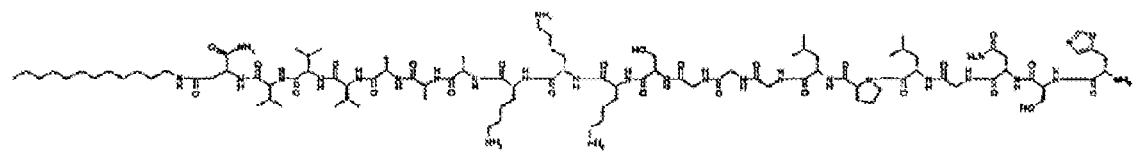
TGF-β1 binding PA
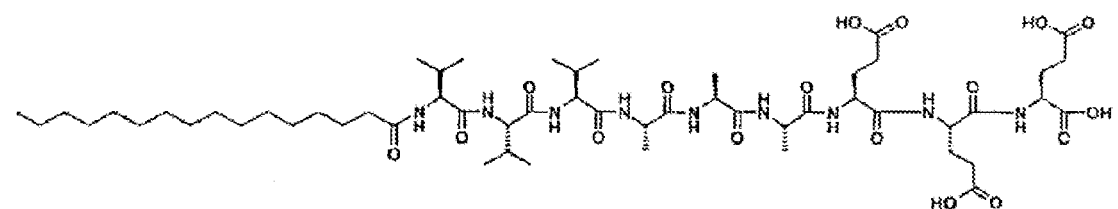
Filler PA
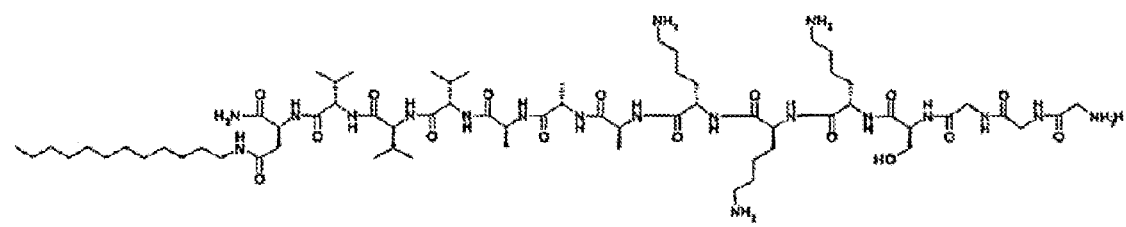
Complementary filler

SELF-ASSEMBLING PEPTIDE AMPHIPHILES AND RELATED METHODS FOR GROWTH FACTOR DELIVERY

This application is a divisional of U.S. patent application Ser. No. 11/005,552, filed Dec. 6, 2004 now U.S. Pat. No. 7,544,661, which claims priority from U.S. Patent Application No. 60/527,504 filed Dec. 5, 2003, the entirety of both of which are incorporated herein by reference.

This invention was made with government support under Grant No. DE-FG02-00ER45810 awarded by the Department of Energy to Northwestern University. The government has certain rights in this invention.

BACKGROUND OF INVENTION

Growth factors play an important role in cell specialization and are promising factors for controlling stem cell differentiation or reactivating dormant biological processes in vivo, both of which may lead to the regeneration of nonfunctional tissues. Growth factors are quickly degraded and rapidly diffuse away from a cellular site or injury. Accordingly, an architecture or scaffold would be useful to retain the growth factor at such a site for release to the surrounding cells in a controlled fashion.

Materials designed molecularly for tissue regeneration are becoming of great interest in advanced medicine. Scaffolds of synthetic polymers, including polymers based on L-lactic or glycolic acid, and biopolymers including collagen, fibrin or alginate have been studied. Growth factors have been physically entrapped in hydrogels as such polymers, covalently linked or bound electrostatically to either anionic polymers or structures such as heparin. Drawbacks to these and related systems relate either to non-specificity of bound growth factors or required degradation of covalent bonds to achieve desired effect. More recently, both natural and synthetic scaffolds have been modified to contain peptides found in extracellular proteins that promote receptor based interactions with cells and have been used to promote cell adhesion or differentiation.

Advances in self-assembly offer new opportunities in molecular design of biomaterials. Amphiphilic molecular building blocks can be assembled in aqueous environments to form scaffolds with well defined and diverse chemical structures. Various classes of peptide-based amphiphiles have been reported in the literature, including amphiphilic peptides and peptides functionalized with hydrophobic components (e.g., alkyl tails) on one or both termini. Amphiphilic peptides have been shown to form a variety of supramolecular structures like nanotapes, ribbons, fibers, and twisted ribbons. These structures originate from β-sheet formation among the amphiphilic molecules. A special case is that of amphiphilic peptide block copolymers that form gels with properties strongly dependent on the secondary structure of the individual peptide blocks. An example of peptide amphiphiles with alkyl tails on one terminus include amphiphiles derived from peptide motifs found in collagen which result in the formation of triple helical units that form spheroidal or disc-like micellar structures depending on the tail length and number of tails. Another class has two tails, one per terminus. This class of amphiphiles displays amyloid-like behavior in that, upon increasing the concentration, they undergo a transition from a random coil to a β-sheet type conformation that leads to fibrillar structures. There are reports of purely peptidic nanostructures with antiparallel arrangements, and one report of two modified peptide amphiphiles that aggregate in an antiparallel arrangement driven by an unnatural alkylated quaternary ammonium salt.

A class of peptide amphiphiles (PAs) is disclosed in one or both of two co-pending applications comprising a linear hydrophobic tail coupled to a peptide block that includes β-sheet forming segments, charged residues for solubility, and biological epitopes. The alkyl tail is attached to the N-terminus of the peptide, and the epitope segment is placed at the C-terminus. Upon application of a trigger such as a change in pH or ion concentration, these PA molecules can self-assemble in an aqueous medium into nanofibers. The alkyl chains are in the core of the fibers, with the epitopes displayed on the periphery for cell interaction. Epitopes that have been incorporated into the PA molecules mimic extracellular matrix proteins and promote cell adhesion or differentiation through cell signaling. It has also been shown that two different PA molecules with different epitopes and complementary charge can be co-assembled into the same nanofiber. See, co-pending application Ser. No. 10/368,517 filed Feb. 18, 2003 (international publication number WO 03/070749) and application Ser. No. 10/294,114 filed Nov. 14, 2002 (international publication number WO 03/054146), each of which are incorporated herein by reference in their entirety.

However, such PA compounds are typically prepared via solid phase synthesis with the peptide component generated from the C-terminus to the N-terminus. Coupling a hydrophobic component to the N-terminus provides a PA compound with either a free acid or amide group on the periphery of the resulting micellar nanofiber assembly as various epitope or peptide sequences often require a free N-terminus for bioactivity, such PA compounds would be ineffective for growth factor interaction.

SUMMARY OF THE INVENTION

In light of the foregoing, it is an object of the present invention to provide the amphiphilic peptide compounds, assembled compositions thereof and/or related methods for use thereof to affect bioavailability of a range of growth factors, thereby overcoming various deficiencies and shortcomings of the prior, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide amphiphilic peptide compounds comprising peptide components coupled at the N-terminus thereof to one or more of a range of epitope sequences capable of non-covalent interaction with one or more growth factors, such epitopes as can comprise and be derived from the recognition product of a phage display process.

It is another object of the present invention to provide a composition comprising an assembly of one or more of the aforementioned amphiphilic peptide compounds for presentation of the epitope binding sequence(s) coupled thereto, such compositions as can comprise other amphiphilic peptide compounds absent such an epitope sequence.

It can also be an object of this invention to provide one or more of the aforementioned compositions further comprising one or more growth factors corresponding to a coupled epitope sequence, such compositions capable of self-assembly for growth factor delivery and release.

It is also an object of the present invention to provide one or more compositional assemblies of the aforementioned amphiphilic peptide compounds and use thereof to affect growth factor bioavailability and/or stem cell differentiation.

Other objects, features, benefits and advantages of the present invention will be apparent from this summary and the following descriptions of certain embodiments, and will be readily apparent to those skilled in the art having of peptide composition and scaffolds or architectures for growth factor delivery. Such objects, features, benefits and advantages will be apparent from the above as taken into conjunction with the accompanying examples, data, figures and all reasonable inferences to be drawn therefrom, alone or in consideration with the references incorporated herein.

In part, this invention can be directed to an amphiphilic peptide compound comprising a peptide component and a hydrophobic component, the peptide component comprising a growth factor recognition product of a phage display process. One or more such recognition products can be coupled to or bonded directly with the peptide component at, about or proximate to the N-terminus of the peptide component, with the hydrophobic component coupled to or bonded directly with the peptide component at, about or proximate to the C-terminus thereof. Such a recognition product can be selected from epitope sequences providing one or more binding interactions with a growth factor, such products/sequences and corresponding growth factors including but not limited to those discussed more fully below. The compounds of this invention and/or peptide components thereof can be substantially linear or branched, such branched configurations and the preparation thereof as disclosed in co-pending application "Branched Peptide Amphiphiles, Related Epitope Compounds and Self-Assembled Structures Thereof," filed concurrently herewith, on Dec. 6, 2004, the entirety of which is incorporated herein by reference.

In part, this invention can also be directed to compositions comprising a plurality of such amphiphilic peptide compounds, with the peptide component of each such compound having a net charge at a physiological pH. Such compositions can further comprise a plurality of amphiphilic peptide compounds having a complementary net charge at a physiological pH, such compounds absent a growth factor recognition product, such that the amino acid sequence of such compounds is of shorter length or less in number than that corresponding to a compound comprising a recognition product. As a result, micellar assemblies of such compounds, in an appropriate medium, provide an enhanced presentation of one or more recognition products, extending beyond the general periphery of the micellar assembly. Such enhanced presentation can be used to affect and/or control the bioavailability of one or more growth factors. As such, various compositions of this invention and methods relating thereto can be used in a stem cell environment for non-covalent interaction or binding with one or more growth factors, whether the growth factor is produced by the stem cell, or delivered to the cellular environment in conjunction with one or more of the aforementioned compositions.

Regardless of compositional use or application, the peptide amphiphiles of this invention can comprise a peptide component of varied length or sequence depending upon desired flexibility, charge and/or capacity of intermolecular interaction or binding. The hydrophobic component of such compounds can also be varied (e.g., ranging from about $C_6$ to greater than about $C_{22}$ alkyl or substituted alkyl, saturated or unsaturated, etc.), such components limited only by resulting amphiphilic character and affect on compositions or assemblies of such compounds.

One embodiment of the present invention is a composition that includes a mixture of peptide amphiphiles, each having a binding epitope, and filler peptide amphiphiles without a binding epitope. The mixture is capable of forming self assembled nanofibers or other micelles which consist of the filler peptide amphiphiles and the self assembled peptide amphiphiles having the binding epitope. The peptide amphiphiles in the composition have a alkyl tail portion, a beta sheet portion, and a charged portion. Preferably the epitope on the peptide amphiphile having the binding epitope has a sequence derived by a phage display process and is longer than the filler peptide amphiphile.

Another embodiment of the present invention is a composition or system of self assembled nanofibers or other self assembled micelles including peptide amphiphiles having a binding epitope and filler peptide amphiphiles. The peptide amphiphiles with the binding epitope preferably longer than the filler peptide amphiphiles. In the self assembled structures the peptide amphiphiles with the binding epitope preferably protrude from the surface of the self assembled nanofiber or micelle. Preferably the peptide amphiphile with the binding epitope is capable of interacting with growth factors or other peptides, amino acids, or nucleic acids through non-covalent interaction, even more preferably the non-covalent interaction between the growth factors and the epitopes does not compete with binding of the growth factors to extracellular receptors.

Compositions of self assembled nanofibers or micelles can comprise hydrogels that may further include a growth factor non-covalently bonded to peptide amphiphiles of the nanofiber having the bonding epitope. Such growth factors may be added in vitro or may be those at the site of an injury of a patient in vivo. The growth factors interacting with the self assembled peptide amphiphiles may include but are not limited to bone morphogenetic proteins, transforming growth factor vascular endothelial growth factor, neurotrophins, and mitogenic factors like FGF-2, Sonic hedgehog and Wnt-proteins. The composition may include cells such as but not limited to stem cells inside the nanofiber hydrogels. Preferably the growth factors non covalently interacting with the self assembled peptide amphiphiles are released to the surrounding tissue or cells through interaction with the extracellular receptors or by degradation of the nanofiber matrix. In addition to the cells, other therapeutic compounds may be encapsulated in or bonded to the hydrogel. These compounds may include but are not limited to anti-inflamatories, chemotherapeutics, or combinations of these inside the nanofiber hydrogels. Preferably the growth factors non covalently interacting with the self assembled peptide amphiphiles are released to the surrounding tissue or cells through interaction with the extracellular receptors or by degradation of the nanofiber matrix.

Another embodiment of the present invention is a method of making self assembled peptide amphiphile nanofibers or micelles that includes self-assembling by mixing or combining peptide amphiphiles having a binding epitope with filler peptide amphiphiles, wherein said peptide amphiphiles with binding epitopes are longer in length than said filler peptide amphiphiles. Nanofibers or micelles maybe formed by addition of multivalent ions, addition of complementary charged peptide amphiphiles, or by dehydration, or addition of an acid or base to the peptide amphiphiles. Where hydrogels are formed, preferably the micelles or nanofibers are formed by addition of multivalent ions or ions already present in cell media or bodily fluids. Preferably the peptide amphiphile having the binding epitope has a sequence derived by a phage display process.

Another embodiment of the present invention is a method of treating a tissue which includes administering to a site on a patient in need of regenerating a tissue, nanofibers or other self assembled micelles including peptide amphiphiles with epitopes for non-covalently bonding to growth factors. The nanofibers and their hydrogels may include cells such as but not limited to stem cells. In addition to cells, other therapeutic compounds may be encapsulated in or bonded to the hydrogel. These compounds may include but are not limited to anti-inflamatories, chemotherapeutics, or combinations of these. Preferably the growth factors noncovalently bonded to self assembled structure are released to the site by interaction with the extracellular receptors or degradation of the matrix. Preferably the self assembled micelles or nanofibers containing growth factors and/or stem cells are administered to a site on a patient having injuries such as but not limited to damaged bone, cartilage, spinal cord, brain tissue, nerves, or a combination of these.

Another embodiment of the present invention is a peptide amphiphile that includes an alkyl tail portion coupled to a first end of beta sheet forming peptide portion also having a second end. An epitope peptide portion of the peptide amphiphile is coupled to the second end of the beta sheet forming peptide portion such that the epitope is available for non-covalent interaction with other molecules or proteins. Preferably the epitope has a sequence that is derived by a phage display process. The peptide amphiphile may alternatively include a charged portion peptide having two ends and coupled between the beta sheet forming portion second end and the epitope peptide portion.

Another embodiment of the present invention comprises an assembly or system for releasing growth factors to cells that includes a scaffold prepared from self assembled peptide amphiphiles, at least a portion of the peptide amphiphiles including peptide epitopes for non-covalently bonding with growth factors, and wherein the growth factor binding epitopes protrude above the nanofiber surface. The amino acid sequence of the epitope is derived from a phage display process. Such a scaffold, may also include stem cells, and can be used in a method for growing tissue, regenerating tissue, or supporting the transplantation of tissue in a patient. In addition to cells, other therapeutic compounds may be encapsulated in or bonded to the hydrogel of the scaffold. These compounds may include but are not limited to anti inflammatories, chemotherapeutics, or combinations of these. The method includes inserting a scaffold to a site on a patient or forming it in vivo. The scaffold includes self assembled peptide amphiphiles having peptide epitopes for non-covalent bonding with growth factors and where the epitopes protrude above the nanofiber surface of the scaffold or are made by a phage display process, and releasing growth factors from the scaffold to the surrounding cells from said scaffold.

The described growth factor binding hydrogels have several applications in the field of regenerative and transplant medicine. The compositions, methods of making, and methods of using them can readily be expanded to other epitopes on the peptide amphiphiles for other growth factors and hence to the regeneration of a wide variety of tissues or support of transplanted tissues in a patient. For example, since BMP-2 and TGF-β1 play an important role in osteoblastic and chondrogenic differentiation of mesenchymal stem cells, respectively, the self assembled micelles of the present invention can be used for the regeneration of bone and cartilage. Second, BMP-2 also plays an important role in the formation of the brain and the dorsal spinal cord. Therefore, the gels can also be used in combination with neural stem cells for the regeneration of damaged spinal cord and/or to repair damaged brain areas in the case of stroke.

As discussed above, In certain embodiments, this invention utilizes an extension of the mixed fiber approach to incorporate a PA that is capable of binding growth factors by selective non-covalent interactions. In this way, the bio-availability of the growth factors can be modulated by tuning the binding strength and number of binding sites. The initial concentration of growth factor will be either raised or decreased depending whether the localizing effect of binding or whether the effect of binding rendering the growth factors inactive is more dominant. In either case, release of growth factors can be sustained over a longer period. To promote binding epitope recognized by a growth factor, a PA can be made such that the epitope is extending from the fiber surface. The required amino acid sequence of the binding epitope can be determined using phage display. For purpose of illustration, growth factors chosen include bone morphogenetic protein-2 (BMP-2) and transforming growth factor β1 (TGF-β1). BMP-2 is, amongst others, involved in the formation of bone and the development of the brain and the dorsal spinal cord, whereas TGF-β1 is implicated in the formation of cartilage and the differentiation of smooth muscle cells. The corresponding gels will be used to control the differentiation of mesenchymal stem cells. Mesenchymal stem cells have been shown to differentiate in vitro and in vivo into a variety of lineages like bone, cartilage, fat, muscle cells and myocardium. The differentiation into the bone lineage under the influence of BMP-2 is shown below.

The gels are superior to the addition of growth factors to media in controlling the differentiation of mesenchymal stem cells into the expected osteogenic lineage. Moreover, the binding gels initially suppress the differentiation into all other lineages. This behaviour is thought to result from either reduced bio-availability of the growth factor or from a more gradual exposure of the cells to these growth factors in the binding gels. Eventually, some α-smooth muscle expression is found in the binding gels as well. This suggests that prolonged exposure to BMP-2 or the absence of factors that drive differentiation to completion might have negative effects on homogeneity of the population. Finally, the endogeneously produced BMP-2 levels seem sufficient when the binding sequence is present to moderate its bioavailability.

The successful co-assembly of the growth factor binding PAs with the regular filler PAs allows the creation of hydrogels that are capable to bind growth factors, retain them in the gels and modulate their bio-availability. More homogeneous populations of specialized cells are obtained initially when mesenchymal stem cells are differentiated in gels with binding PAs compared to those differentiated in the absence of binding PAs. Other filler PAs may be desired to vary the physical properties of the gels depending on its applications and other binding sequences might be desired to optimize binding strengths. In addition, the approach demonstrated by this invention allows the incorporation of multiple signals by simple mixing of multiple binding PAs with a filler. Most likely, multiple growth factors will be required to further optimize the differentiation of stem cells. The differentiation of mesenchymal stem cells exposed to multiple growth factors is currently being investigated. Potentially, temporal release in the multiple growth factors systems can be achieved by selecting binders with different association constants for the growth factors. In addition, in vivo studies of the systems described here are being performed. Finally, the methodology presented here can readily be extended to any growth factor or protein implicated in cell recruitment, specialization or maintenance, thereby making it a highly promising approach for regenerative medicine.

BRIEF DESCRIPTION OF THE DRAWING

FIG. 1 illustrates representative PAs comprising epitope sequences (SEQ ID NOS 67-68, 4 and 69) and complementary PAs for use in assembly therewith.

DETAILED DESCRIPTION OF CERTAIN EMBODIMENTS

The invention describes a system based on self-assembling peptide amphiphiles (PAs) that is capable of binding growth factors through specific non-covalent interactions. Growth factors play an important role in cell signaling and are therefore promising factors for controlling the differentiation of stem cells, supporting the incorporation of transplanted tissue, and or specific molecular or physiological, or re-activating dormant biological processes in vivo which may lead to the regeneration of non-functional tissues. Growth factors are rapidly degraded in vivo and rapidly diffuse away from the injury site. Therefore, a scaffold is needed that retains the growth factor at the injury site and releases the growth factors to the surrounding cells in a controlled fashion. Self assembled peptide amphiphiles based hydrogels have been shown to be able to fulfill several functions of an extacellular matrix (ECM), i.e. promoting cell adhesion and controlling differentiation. The present invention concerns a modification of these ECM substitutes with peptide sequences that are capable of binding growth factors, which include but are not limited to bone morphogenetic protein-2 (BMP-2), transforming growth factor β1 (TGF-β1), VEGF, and IL-6 in a specific fashion. These growth factor peptide sequences may be obtained through phage display techniques, coupled to peptide amphiphiles to form binding peptide amphiphiles. The binding peptide amphiphiles and filler peptide amphiphiles maybe self assembled to form a hydrogel which can be molded into a shape and used as a scaffold for tissue repair. Alternatively binding peptide amphiphiles and filler peptide amphiphiles may be introduced in vivo or in vitro to a sample of cells or tissue and self assembled to a hydrogel in the sample.

As discussed above, the peptide amphiphiles of this invention can comprise an alkyl tail, a β-sheet forming peptide sequence, and a bio-active peptide sequence. The first two blocks result in the formation of micellar fibers, such as but not limited to nanofibers, which under the proper conditions (neutralization of addition of multivalent ions) form hydrogels or other solvent filled wet gels. Preferably the bioactive epitope is partially charged for solubility, but this charge can be varied over a wide range of sequences like integrin-binding sequences, neuro-active sequences etc. Furthermore, peptide amphiphiles of complementary charge co-assemble to form mixed fibers. This principle may be used to prepare nanofibers consisting of regular PAs and longer PAs with growth factor binding epitope sequences, in which the binding sequences are extending from the fiber surface. The desired growth factor binding sequences are obtained through phage display using randomized peptide libraries, which leads to strong binding sequences using combinatorial selection processes. Release of the growth factors will be induced by degradation of the matrix, binding to an extracellular receptor, or a combination of these.

Existing technologies entrap the growth factors in hydrogels, link them covalently with polymeric tethers (WO 03/040336 and U.S. Pat. Pub. No. 0020007217) or bind them electrostatically to either anionic polymers (WO 0/13710) or heparin (WO 00/64481). The disadvantage of the tethered system is the complex preparation and the possibility that the growth factors cannot reach the extracellular receptors. Entrapped growth factors and the growth factors complexed to the anionic polymer are released relatively quick and control over sustained release is poor. For example, the growth factors bound to the anionic polymer are released within 8 hours. The heparin-binding system is non-specific (e.g. non-desired binding of factors present in the serum is possible) and is limited to a subset of growth factors. Advantageously, the present invention is designed such that only the desired growth factor is complexed with a binding strength that is high enough to retain the growth factor in a bound state but is weak enough that it does not compete with binding to the extracellular receptors.

One aspect of the invention described herein is that it may be used for the derivation of peptide sequences that bind growth factors using phage display techniques and the subsequent preparation of peptide amphiphiles bearing these binding sequences. Growth factors prepared by the phage technique may include the bone mophogenetic proteins, transforming growth factor ⊕1, the neurotrophins, and the mitogenic factors FGF-2, Sonic Hedgehog and Wnt-3a. These growth factor proteins are coupled to shorter peptide amphiphile to form longer peptide amphiphiles bearing the growth factor epitope. These growth factor epitope bearing PAs, or binding peptide amphiphiles, are co-assembled with shorter filler or complementary filler PAs to generate nanofibers with the binding epitopes extending from the surface, which can subsequently form hydrogels upon the addition of multivalent ions, or a change in pH. The resulting hydrogels can then be used, either with cells, such as but not limited to stem cells, encapsulated inside the hydrogel or solely as a delivery vehicle, for tissue regeneration in vivo. In addition to cells, other therapeutic compounds may be encapsulated in or bonded to the hydrogel. These compounds may include but are not limited to anti-inflamatories, chemotherapeutics, or combinations of these.

Phage display may be used to generate molecular probes against specific targets and for the analysis and manipulation of protein-ligand interactions. Phage display is used to determine the amino acid sequences, peptides, or proteins that will bind to the target molecules such as but not limited to amino acids, peptides, growth factors, enzymes, and various nucleic acids. Phage display may be performed on target molecules like growth factors physisorbed to microtiter well plates using a commercial library. Preferably the library consists of phages in which the N-terminus of the G3 coat protein has been extended with 1 to about 13 or more randomized amino acids in such a way that every possible combination of amino acids is present. The library is exposed to the target molecules such as growth factors and subsequently non-specifically bound phages are eluted with a detergent solution. After retrieval of the bound phages, this population is amplified in for example E. Coli and the process is repeated two more times with increasingly stringent elution conditions. The final population is strongly enriched towards binding phages, and the DNA of several of the clones can be sequenced, allowing the identification of the amino acid sequence displayed on these phages. Subsequently, an ELISA assay may be performed to estimate the relative binding strengths of the isolated clones. Solid state synthesis is used to make the peptides for making the binding peptide amphiphiles using the identified amino acid sequences.

Peptide components in the filler PAs and the binding epitope peptide amphiphiles of the present invention may include naturally occurring amino acids and artificial amino acids. Incorporation of artificial amino acids such as beta or gamma amino acids and those containing non-natural side chains, and/or other similar monomers such as hydroxyacids are also contemplated, with the effect that the corresponding component is peptide-like in this respect and self assemble to form micelles such as nanofibers.

Various peptide amphiphiles of the present invention can be synthesized using preparatory techniques well-known to those skilled in the art, including those disclosed in the aforementioned incorporated publication WO 03/054146 and modifications of those originally described by Hartgerink, et al. (See e.g., J. D. Hartgerink, E. Beniash and S. I. Stupp, Science 294, 1683-1688, 2001), which is also incorporated in its entirety by reference. Also contemplated in the practice of this invention are branched peptide amphiphiles with which the synthetic methods and epitopes of the present invention may be used. Branched peptide amphiphile may be made by the using the methods and compostions as disclosed in the forementioned co-pending application filed concurrently herewith on Dec. 6, 2004, the contents of which are incorporated herein by reference in their entirety. Such a branched peptide amphiphile with a binding epitope could be self assembled into a nanofiber. The branched peptide amphiphile would have an alkyl tail portion coupled to the first end of a beta sheet forming peptide portion and at a second end to an epitope peptide portion that includes one or more peptide branches. The peptide includes branching amino acids and a charged peptide portion. The branched epitope peptide portion may be coupled to a second end of the beta sheet forming peptide portion of the peptide amphiphile. The binding epitope sequence for the branched peptide may be derived from a phage display process. The synthetic schemes set forth in these references may be applied to the present invention. Peptide amphiphiles may be in their fully protonated form, partially protonated form, or as acid or basic addition salts. Generally such peptide amphiphiles can be made by standard solid-phase peptide chemistry, as described in the aforementioned incorporated references or as provided herein. Modifications of these synthetic methods can be made as would be known to those skilled in the art and aware thereof, using known procedures and synthetic techniques or straight-forward modifications thereof depending upon a desired amphiphile composition or peptide sequence.

Filler peptides, of the sort shown in FIG. 1, are preferably shorter in length than the peptide amphiphiles with the binding epitopes so that self assembled nanofibers from a combination of these peptide amphiphiles results in protrusion of the growth factor binding epitope from the surface of the nanofiber. The complementary filler peptide amphiphiles have side groups from the amino acids which interact with those of the filler peptide via acid base or other types of bonding.

The peptide sequences derived from the phage display process may be used as a binding site or epitope on a peptide amphiphile for non-covalently bonding to peptides and molecules that include but are not limited to growth factors, enzymes, nucleic acids (RNA, DNA), and amino acids. While phage display is preferred for deriving the epitope sequences, other complementary methods for identifying and determining the sequence of binding epitopes cam be used, such as but not limited to yeast hybrid systems. These binding peptides or epitopes may be coupled to the free end of the beta sheet forming peptide, the free end of the charged peptide, or the free end of the spacer peptide.

A peptide amphiphile design can comprise a simple hydrophobic tail which serves to create the slender portion of the molecule's conical shape for self assembly of the peptide amphiphiles. Preferably the hydrophobic tail is an alkyl chain that can be a variety of sizes but is preferably be greater than 6 carbon atoms in length. The alkyl tail is covalently bonded to the beta sheet forming structural segment of the peptide amphiphile.

The beta sheet peptide structural segment may be used to covalently link the tail group to the phage peptide; or the charged peptide, spacer peptide, and phage peptide; or the charged peptide and phage peptide. The beta sheet peptide structural segment is covalently bonded at one end to the tail and at its other end to an amino acid sequence of the various peptides. If cross-linking is desired, cysteine amino acids maybe utilized in any of the segments, but preferably in the structural beta sheet segment. If cross-linking is not desired, other hydrophobic amino acids such as but not limited to alanine, serine, or leucine may be used in this region (e.g. SLSL (SEQ ID NO:1) or AAAA (SEQ ID NO:2) as described in more detail herein). This cysteine-free system may be more appropriate for in vivo biological applications to control the degradation rate of the nanofiber matrix. The SLSL (SEQ ID NO:1) modification to the system may be expected to lead to a slower self assembly of the nano fibers which may be used to control in vivo assembly of scaffolds. Without wishing to be bound by theory, it is believed that the bulky leucine side chains may require more time to pack into the fiber. A slowed self-assembly may also have greater applications in a functional, in situ environment such as an operating room, where it may be advantageous to have delayed formation of the nano-fibers. The structural beta sheet forming segment may also include a flexible linker composed of glycine or other amino acids. When the structural segment includes hydrophobic amino acids, it and the alkyl tail may be considered a hydrophobic segment. Where the structural segment includes hydrophilic amino acid, it and the hydrophilic head group may be considered as a hydrophilic segment.

The β-sheet forming unit preferably includes those hydrophobic amino acids which can interact to form beta sheets and which help form the overall conical shape of the peptide amphiphile. For the protruding peptide amphiphile, the number of amino acid in this unit may be chosen to provide a peptide amphiphile that is longer than filler peptide amphiphiles used to form the nanofibers and provide accessibility to the peptide on the bonding peptide amphiphile. There may be from about 4 to about 10 amino acids in this segment and most preferably about 6 amino acids. For a β-sheet forming segment suitable amino acid may include but are not limited to glycine, alanine, valine, leucine, and isoleucine, and other non-naturally occurring amino acids which may used in a similar chemical and structural manner in the peptide amphiphile. A charged segment is present in the binding peptide amphiphile which provides for solubility of the peptide amphiphile in an aqueous environment, and preferably at a site on a patient. The charged peptide segment may include those amino acids and combinations thereof which provide this solubility and permit self assembly and is not limited to polar amino acids such as E or K and combinations of these for modifying the solubility of the peptide amphiphile. There may be from about 2 to about 7 amino, and preferably there are about 3 or 4 amino acids in this segment. This segment is attached at a first end to the structural peptide and it's second end used for bonding to the peptide derived from the phage display process. A spacer group peptide may also be included into the peptide amphiphile. The space may include amino acids such as but not limited to S and G, and the space may include from 1 to about 6 amino acids. Where the displayed peptides on the phage have a free N-terminus, the classical synthetic scheme for peptide amphiphiles may be amended to provide a free N-terminus. This may be achieved by synthesizing an aspartic acid derivative with which the side chain can be functionalized with dodecyl amine. Coupling of this amino acid to the Wang-resin allowed the completion of the PA synthesis through classical solid state Fmoc-chemistry without further need to functionalize the N-terminus. The free PA may be obtained through treatment with 95% TFA/2.5% water/2.5% triisopropylsilane. Residual TFA can be removed by dissolving the PA in 3 mM HCl, equilibrating for 1 hr at room temperature followed by lyophilization. The successful synthesis of these molecules maybe confirmed using electrospray mass spectrometry.

The peptide amphiphiles with the growth factor epitopes maybe self assembled at a site on a patient in vivo using ions present in bodily fluids and or added ions/reagents to promote self assembly. Alternatively a composition of suitable peptide amphiphiles with growth factor binding epitopes is poured into a mold and self assembly used to form a scaffold in the shape of a tissue or bone to be replaced or regenerated. The molded scaffold may be inserted into the patient at the site in need of the repair or regenerative treatment. In the case of tissue transplant, the peptide amphiphiles with the growth factor binding epitopes may be formed into a support structure or matrix in a mold and used as a support in the patient for the transplanted tissue. The peptide amphiphile nanofibers or scaffolds thereof may include cells such as but not limited to stem cells. Other therapeutic compounds may be encapsulated in or bonded to the hydrogel. These compounds may include but are not limited to anti imflamatories, chemotherapeutics, or combinations of these.

Co-assembly of peptide amphiphiles with growth factor binding epitopes with the shorter beta sheet structural peptide-charged peptide acid-terminated filler peptide amphiphiles may be used to prepare nanofibers and scaffolds of the present invention. Without limitation one or more peptide amphiphiles with different growth factor binding epitopes may be used, and a variety of filler peptide amphiphiles may be used to prepare the scaffolds and nanofibers of the present invention. The amount of peptide amphiphile with growth factor binding epitopes compared to the filler peptides amphiphiles maybe varied without limitation in the preparation of the scaffolds and nanofibers of the present invention. The self assembled micelles and nanofibers may be characterized by NOE and FT-IR spectroscopy, circular dichroism; nanofiber fiber networks can be visualized using transmission electron microscopy.

The peptide amphiphile with the binding epitope may be made by choice of a peptide sequences for the epitope that is capable of interacting with growth factors or other peptides such as but not limited to, amino acids, or nucleic acids, through non-covalent interaction. The degree of non-covalent interaction between the growth factors or other peptides and the peptide amphiphiles with the binding epitopes is chosen such that the epitope does not compete with or has less binding affinity for the growth factors or other peptides as compared to extracellular receptors. Passive release experiments may be used to characterize and subsequently modify the affinity of various nanofibers having growth factor binding epitopes. This characterization may be performed on self assembled nanofiber gels containing growth factors in pre-blocked microtiter plates. These gels may be prepared by first mixing 2% solutions of PAs in the appropriate ratio, followed by a 1:1 dilution with TBS. Growth factors may then be added followed by the addition of 2 equivalents multivalent ions to induce gelation and self assembly. The supernatant may be assayed for its growth factor content to access the growth factor binding capability of such gels.

While it is preferable for tissue growth and other treatments that the binding epitope have less affinity for various peptides than the extracellular receptors of nearby cells or tissues, it is contemplated that it may be desirable the binding epitope of the peptide amphiphile strongly chemically bond to peptides, growth factors, enzymes, or nucleic acids or other molecules from a fluid or sample of cells. In this case binding peptide amphiphiles with suitable epitopes can be self assembled and immobilized on the surfaces to form sensor coatings or removal media. Hydrogels formed from self assembly of these strongly binding peptide amphiphiles could be molded for insertion into a site on a patient or for use in a filtration system. The hydrogels could be used to remove target peptides like HGF or VEGF from a site such as a joint or tumor on a patient or from a fluid in a patient.

EXAMPLES OF THE INVENTION

The following non-limiting examples and data illustrate various aspects and features relating to the compounds, compositions and/or methods of the present invention, including the synthesis of a range of amphiphilic peptide compounds, with or without epitope sequences capable of non-covalent interaction with growth factors, self-assembly of such compounds or compositions and the use thereof to affect growth factor bioavailability and stem cell differentiation. In comparison with the prior art, the present compounds, compositions and/or methods are surprising, unexpected and contrary thereto. While the utility of this invention is illustrated through the use of several compounds/compositions and assemblies, it will be understood by those skilled in the art that comparable results are obtainable with various other compounds, compositions and/or assemblies, as are commensurate with the scope of this invention.

All resins and Fmoc-1-amino acids were obtained from Novabiochem (San Diego, Calif.). All reagents for solid phase synthesis were of synthesis grade and obtained from Applied Biosystems (Foster City, Calif.). All other reagents were obtained from Aldrich Chemical Co. (Milwaukee, Wis.) and were used as received. Solvents for solid phase peptide synthesis were acquired from Applied Biosystems and were peptide synthesis grade. Other solvents were obtained from Fisher Scientific and were used as received unless stated otherwise.

PAs were synthesized using an Applied Biosystems 433A automated peptide synthesizer. NMR spectra were acquired on a Varian Inova 500 MHz spectrometer at room temperature. Electro Spray mass spectra were collected on a Micromass Quattro II Triple Quadrupole HPLC/MS/MS Mass Spectrometer. CD spectra were recorded on a Jasco J-715 spectropolarimeter with a Jasco PTC-348WI peltier-effect temperature controller. FT-IR spectra were run on a BioRad FTS-40 FT-IR machine, from 400-4000 nm with a 2 $cm^{-1}$ resolution.

Circular Dichroism Spectroscopy. Quartz cells with a 0.1 cm path length were used for all experiments. Each spectrum was recorded from 300 to 190 nm at a scan speed of 100 nm/min, a response time of 2 seconds and a band width of 1 nm and averaged over five scans. Samples were prepared at a concentration of 0.1 mg/mL in water unless stated otherwise.

Acid-Base titrations. pKa titrations were preformed on PAs 1-4 in the range of pH 2-10 with a Fisher Accumet pH meter at a concentration of 3.5 mg/mL in 100 mM KCl. For the acidic PAs 2 and 4, 0.1N KOH was added in 1-5 μL increments, starting at low pH, whereas for the basic PAs 1 and 3, 0.1N HCl was added in 1-5 μL increments, starting at a high pH.

NMR NOE spectroscopy. PAs 1-6 were dissolved in $d_6$-DMSO at concentrations of 5 mg/mL. NOESY spectra were measured in $D_2O$ with a mixing time of 0.1 s and 128 scans at a concentration of 10 or 15 mg/mL of each PA, at a 1:1 molar ratio. For FT-IR studies, 2% by weight samples were lyophilized from water and then pressed into KBR pellets.

Scheme 1. Chemical structures of peptide amphiphiles

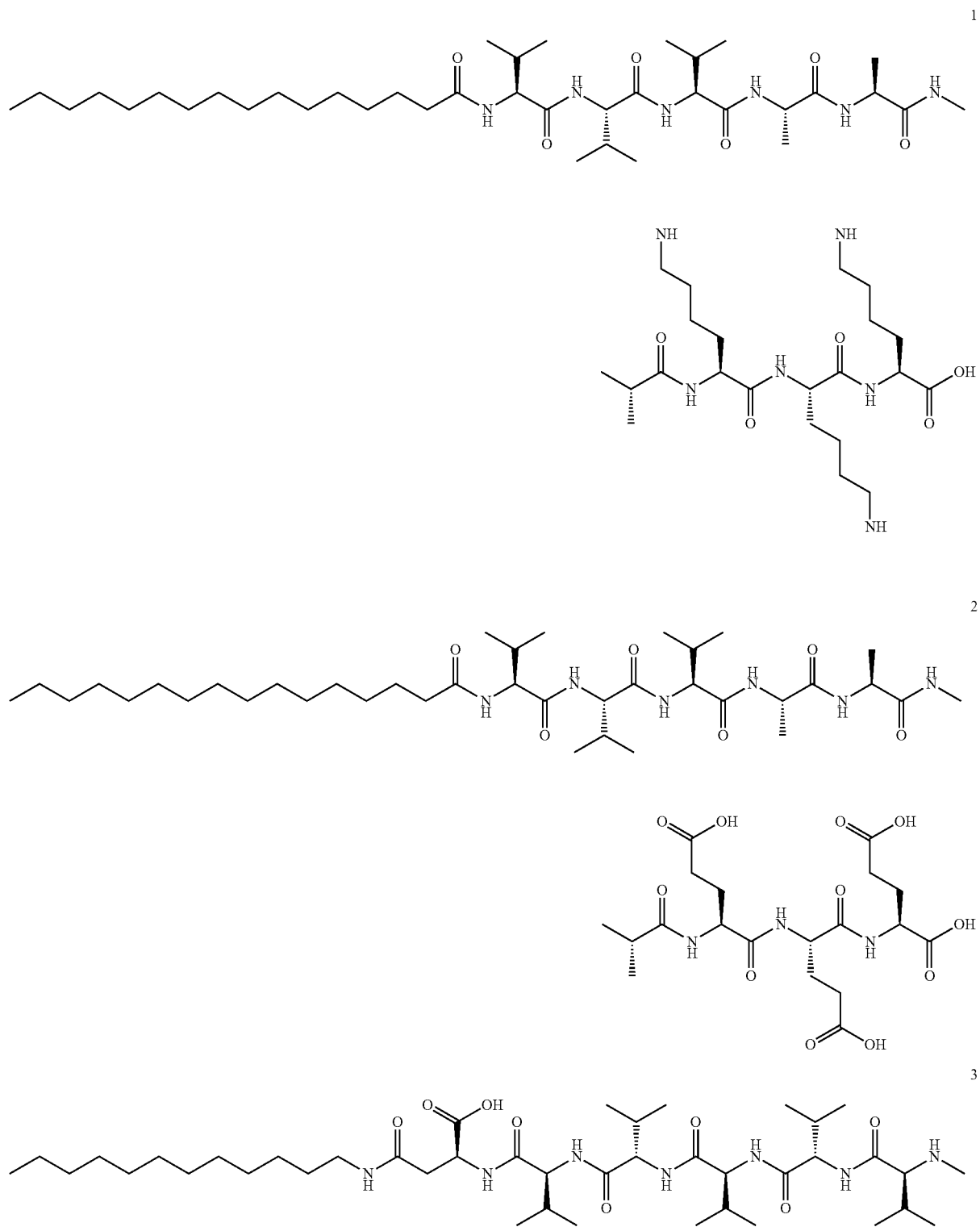

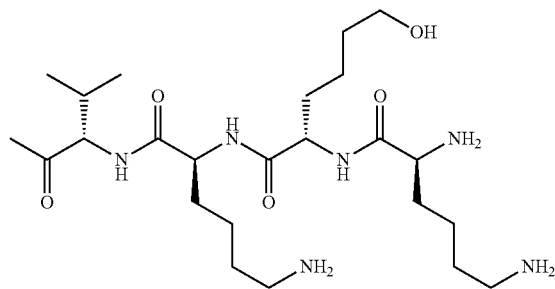

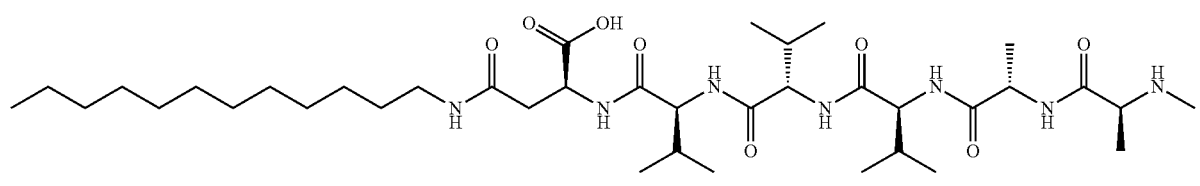

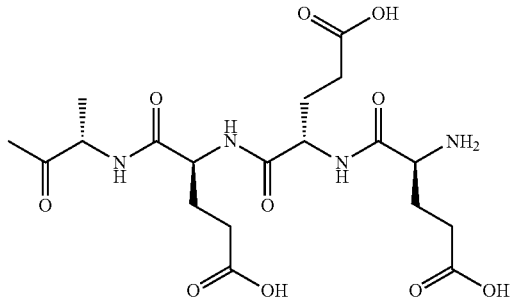

Example 1

Four PAs, two with a triple lysine sequence (1 (SEQ ID NO:3), 3 (SEQ ID NO:5) and two with a triple glutamic acid sequence (2 (SEQ ID NO:4), 4 (SEQ ID NO6)), were prepared (Scheme 1). PAs 1 and 2 were prepared by standard Fmoc solid-phase peptide techniques using a preloaded Wang resin followed by alkylation with palmitic acid with 2-(1H-benzotriazole-1-yl)-1,1,3,3-tetramethyluronium hexafluorophosphate (HBTU) as a coupling reagent. The amphiphile was cleaved from the resin with a mixture of 95% trifluoroacetic acid (TFA), 2.5% water and 2.5% tri-isopropylsilane (TIS). For the synthesis of peptide amphiphiles 3 and 4, amino acid 7 was synthesized according to Scheme 2. N-Carbobenzyloxy-L-aspartic anhydride was reacted with dodecylamine, yielding fatty acid amino acid 5. The CBz group was then removed by catalytic hydrogenation to yield 6, followed by Fmoc-protection of the amine. This synthesis proceeds readily on a 5 gram scale. Product 7 was then coupled to a rink resin using HBTU as a coupling reagent. Subsequently, the remaining amino acids were added to 8 using standard Fmoc solid phase techniques. Standard cleavage conditions yielded PAs with reverse structure as previously described. $^1$H NMR and electrospray ionization mass spectrometry are consistent with the expected structures.

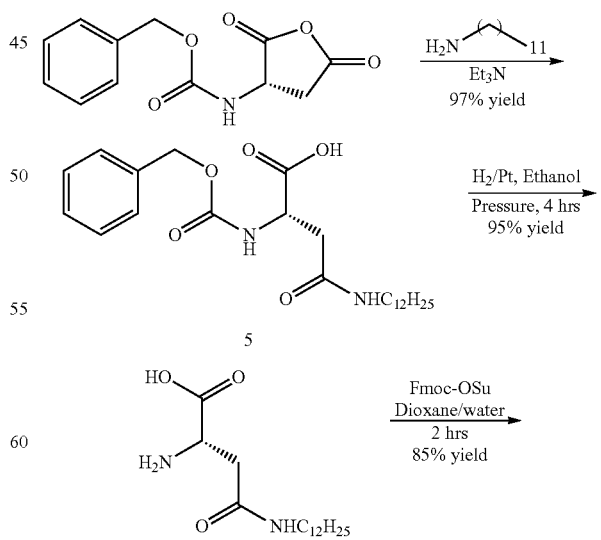

-continued

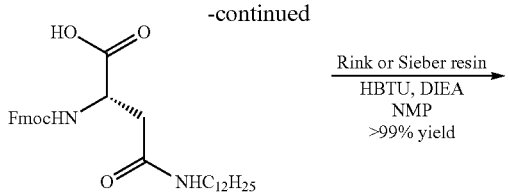

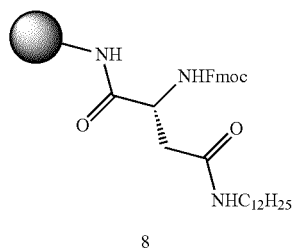

Example 1a

N-dodecyl-2-carbobenzyloxyamino-succinamic acid (5). N-Carbobenzyloxy-L-aspartic anhydride (1 mmol) was dissolved in 50 mL methylene chloride, followed by the addition of 1.05 eq of dodecylamine and 1.1 eq of triethylamine. The reaction was capped to prevent evaporation, and stirred for 12 hours. When no trace of starting material could be detected by thin layer chromatography (TLC) ($CH_2Cl_2$, 5% MeOH), the reaction was quenched with 20 mL 1N hydrochloric acid followed by extraction with chloroform (5×). The organic layer was dried over magnesium sulfate, and 7 was obtained as a white solid (yield 97%).

$^1$H NMR ($CDCl_3$): δ 0.8 (t, J=8.5 Hz, 3H, tail $CH_3$), 1.18 (s, 18H $C_9H_{18}$ tail), 1.48 (br-s, 2H, $CONHCH_2$), 2.68 (s, 2H, $CONHCH_2CH_2$), 3.15 (br-s, 2H, Asp $H_β$), 4.49 (m, 1H, Asp $H_α$), 5.12 (s, 2H, $PhCH_2O$), 7.28 (s, 5H, Ph). $^{13}$C (DMSO-$D_6$) δ 14.6, 22.8, 29.4, 29.6, 29.7, 32.0, 52.2, 56.7, 66.1, 128.4, 129.0, 137.7, 156.5, 171.1, 172.5. ESI MS: m/z: 435.4 ($MH^+$).

Example 1b 2-amino-N-dodecyl-succinamic acid (6). In 100 mL ethanol, 100 mmol of 7 was dissolved and transferred to a reaction vessel containing Pd and C (10% by weight). The vessel was then placed under hydrogen (35 Torr) for 3 hours. The reaction mixture was filtered over celite, and the product obtained as a white solid after evaporation to dryness under reduced pressure. Yield 95%.

$^1$H NMR ($CD_3CN$): δ 1.15 (m, 23H, aliphatic tail), 1.3 (m, 2H, $CONH_2CH_2CH_2$), 2.37 (br-s, 2H, $CONH_2CH_2$), 3.55 (m, 3H, Asp $H_β$), 4.6 (m, 1H, Asp $H_α$). ESI MS: m/z: 301.2 ($MH^+$).

Example 1c

N-dodecyl-2-Fmoc-amino-succinamic acid (7). Into 200 mL of a water/dioxane (1:1 v:v) mixture, 6.6 mmol of 6 were dissolved with 1.3 mL (1.5 eq.) of triethylamine followed by 1 eq. of Fmoc-OSuccinimide (Fmoc-OSu). The reaction was monitored by TLC($CH_2Cl_2$, 10% MeOH) and after 2-3 hours, all of the Fmoc-OSu was consumed. The reaction was quenched with acid resulting in a white precipitate that was collected by filtration. Yield 85%.

$^1$H NMR ($d_6$-DMSO): δ 0.84 (t, J=8 Hz, 3H, terminal aliphatic $CH_3$), 1.19 (s, 18H, aliphatic $CH_2$), 1.34 (s, 2H, $NH_2CH_2CH_2$), 2.61 (br-s, 2H, $CONHCH_2$), 3.08 (s, 2H, Asp $H_β$), 4.24 (m, 3H, Asp $H_α$+FmocCH2CONH+FmocCH), 7.3 (t, J=9 Hz, 1H, FmocH), 7.39 (t, J=9 Hz, 1H, FmocH), 7.68 (d, J=8.5 Hz, 1H, FmocH), 7.85 (d, J=9 Hz, 1H, FmocH). $^{13}$C (DMSO-$D_6$) δ 14.6, 22.8, 29.4, 29.5, 29.7, 32.0, 46.1, 47.3, 52.2, 6.7, 120.8, 126.0, 127.7, 128.3, 141.5, 144.5, 156.5, 171.1, 172.5. ESI MS: m/z 524 ($MH^+$).

Example 1d

PA synthesis and purification. PAs 1-2 were prepared as described in ref 3. For PA's 3-6, the standard rink resin was placed in a reaction vessel and deprotected three times with 30% piperidine in NMP, and then coupled to 2 eq. of 7 overnight. Coupling was repeated until a ninhyndrin test showed negative results. This modified resin 8 was then loaded onto the automated synthesizer, and peptide synthesis proceeded as for PAs 1-2. When the automated synthesis was complete, the PA was cleaved from the resin as described in ref 3.

Example 1e $C_{15}H_{31}$CONHVal-Val-Val-Ala-Ala-Ala-Lys-Lys-Lys-COOH (1) (SEQ ID NO:3)

$^1$H NMR ($d_6$DMSO): δ 0.80-0.84 (m, 21H, Val, +tail $CH_3$), 1.22 (br-s, 28H, $C_{14}$ aliphatic tail), 1.36 (m, 6H, Ala Hp), 1.51 (m, 11H, Lys H, +tail $CH_2CH_2CONH$), 1.62 (m, 6H, Lys $H_β$), 1.91 (m, 9H, Val H, +Lys $H_α$), 2.16 (m, 2H, tail $CH_2CONH$), 2.73 (s, 6H, Lys $H_β$), 4.10-4.23 (m, 9H, $H_α$), 7.6-8.1 (Amide NH). ESI MS (MeOH:$H_2O$ 1:1 v:v): m/z=1151 ($MH^+$).

Example 1f $C_{15}H_{31}$CONHVal-Val-Val-Ala-Ala-Ala-Glu-Glu-Glu-COOH (2) (SEQ ID NO:4)

$^1$H NMR ($d_6$DMSO): δ 0.81 (br-s, 21H, Val, +tail $CH_3$), 1.21 (br-s, 31H, $C_{14}$ aliphatic tail), 1.45 (s, 2H, Ala $H_β$), 1.75 (m, 6H Glu $H_β$), 1.94 (m, 9H, Val$_β$+Glu $H_β$), 2.24 (s, 6H, Glu $H_γ$), 4.2 (s, 9H, $H_α$), 7.6-8.1 (Amide NH). ESI MS (MeOH:$H_2O$ 1:1 v:v): m/z=1177 ($MNa^+$).

Example 1g

Asp($CONHC_{12}$)-Val-Val-Val-Val-Val-Val-Lys-Lys-Lys-$NH_2$ (3) (SEQ ID NO:5)

$^1$H NMR ($d_6$DMSO): δ 0.82 (br-s, 39H, Val H, +tail $CH_3$), 1.22 (br-s, 20H, $C_{10}$ aliphatic tail), 1.34-1.53 (m, 6H, Lys $H_γ$), 1.69 (m, 6H, Lys $H_β$), 1.93 (m, 12H, Lys $H_δ$+Val $H_β$), 2.74 (m, 2H, tail $CH_2NH$), 2.98 (br-s, 6H, Lys $H_ε$), 4.09-4.44 (m, 9H, $H_α$), 7.02-8.25 (Amide NH). ESI MS (MeOH:$H_2O$ 1:1 v:v): m/z=1279 ($MH^+$).

Example 1h

Asp($CONHC_{12}$)-Val-Val-Val-Ala-Ala-Ala-Glu-Glu-Glu-$NH_2$ (4) (SEQ ID NO:6)

$^1$H NMR ($d_6$DMSO): δ 0.82 (br-s, 21H, Val $H_γ$+aliphatic tail $CH_3$), 1.22 (s, 20H, tail $C_{10}$), 1.32 (m, 9H, Ala $H_β$), 1.74 (m, 3H, Glu $H_β$), 1.94 (m, 6H, Glu $H_β$+Val $H_β$), 2.25 (m, 6H, Glu H$_\gamma$), 2.97 (d, J=6 Hz, 2H, tail CH$_2$CH$_2$CONH), 4.10-4.44 (m, 9H, H$_\alpha$), 7.23-8.2 (Amide NH). ESI MS (MeOH:H$_2$O 1:1 v:v): m/z=1197 (MH$^+$).

Example 2

When dispersed in aqueous media in the presence of suitable stimuli, PAs typically self-assemble into high aspect ratio cylindrical nanofibers. Based on previous work, fibers consisting of either one PA molecule or a mix of two PA molecules would be expected to show secondary structures with β-sheet-like hydrogen bonding. It was anticipated that mixing of the negatively charged 2 or 4 with oppositely charged 1 or 3, respectively, would result in parallel β-sheet-like hydrogen-bonding arrangements, while mixing 1 or 2 with amine terminated oppositely charged 4 or 3, respectively, could result in antiparallel arrangements.

Example 3

At a concentration of 0.1 mM, the CD spectra of 2-4 revealed peptide segments with predominantly random coil character. This most likely results from electrostatic repulsion among the highly charged molecules. Upon a change of pH to neutralize the charges or upon addition of calcium ions, all PAs exhibited β-sheet signatures. In contrast, 1 exhibits a β-sheet signature under any pH. 1 may be less charged than the others, since the acid terminus can neutralize the charge of one of the lysine residues, giving the molecule a formal net charge of +2. This lower overall charge may reduce repulsion and allow β-sheet hydrogen bonding within the fibers to take place. Conversely, 4 would have a formal net charge of –2, as the amine terminus would neutralize the charge of one of the glutamic acid residues, allowing for the β-sheet interactions to occur. However, 4 still exhibited a disordered CD signature. To resolve this apparent contradiction, the actual charge state of and apparent pKa of the aggregates at pH 7 was determined to better understand the driving forces for self-assembly of these various systems.

Example 4 pKa titrations of aggregates of molecules 1-4 were carried out at a concentration of 3 mM. All titrations were started at a pH where the molecules were already in their aggregated state in order to avoid kinetic effects due to self-assembly. Only the pKa titration of 3 showed sharp transitions, correlating to two apparent pKa's, one attributed to the deprotonation of the more solvent accessible amine terminus, and the other originating from one or more of the ε lysine amines. Aggregates of PAs 1, 2 and 4 show complex curves with transitions occurring over wide ranges, implying that the protonation/deprotonation of these supramolecular objects occurs slowly, with variations of acidity due to the local microenvironments within the nanofibers. It is clear from these results that aggregation changes the apparent pKas of the acid and amine groups, consistent with recent reports in the literature.

Example 5

Co-assembly of charge complementary PA molecules should lead to fibers containing a mix of the two components with β-sheet hydrogen bonding arrangements. When 2 is mixed with the triple lysine amphiphiles 3 or 1 (abbreviated as 2/3 or 2/1), the CD-spectrum obtained corresponds to a pure β-sheet. The fact that the observed β-sheet signature is not merely a superposition of individual CD spectra of the two components strongly suggests the formation of mixed nanofibers in which two molecules form a single aggregate structure. PA 1 mixed with the triple glutamic acid PAs 4 or 2 (1/4 or 1/2) exhibit similar behavior. When mixing two PAs of similar charge, the 1/3 lysine mixture shows a β-sheet, whereas the 2/4 glutamic acid mixture shows disordered conformation, possibly due to greater charge repulsion among the glutamic acid residues.

Example 6

In order to further demonstrate co-assembly of the molecules within the fibers, nuclear overhauser (NOE) spectroscopy was performed on a 1.5% by weight gel made up of the charge complementary PAs. A representative NOESY of 2 and 3 (2/3) shows close contacts (<3 Å) observed between the Glu-H$_\beta$ protons of 2 and the Lys-H$_\epsilon$ and Val-H$_\delta$ protons of 3, respectively. Several other possible intermolecular contacts were detected but could not be attributed unambiguously to 2/3 contacts. These results provide additional evidence that the two PA molecules are co-assembled within the same nanofiber.

Example 7

Once the successful co-assembly of the amphiphiles was established, the gelation behavior of the systems from both single and multiple PAs was investigated. One-weight percent solutions of 1-4 were slightly opaque and could be gelled by the addition of acid (1,3) or base (2,4), respectively. Transmission electron microscopy reveals the formation of nanofibers with average diameters of 6.5 nm and average lengths of several hundred nanometers, similar to those observed previously in other PAs.

Example 8

Phage display is typically used to find receptor-blocking peptides, i.e. sequences with high binding constants. To transfer a growth factor from the PA binding site to the cell receptor, an extremely high binding constant is not required and might even be unfavorable. Therefore, the 7-mer commercial phage library was elected over the 13-mer library, aiming at intermediate binding strengths. Growth factors were physisorbed onto 96-well plates and subsequently exposed to the phage library. After incubation at room temperature for 60 minutes, the unbound phage was removed by rinsing with detergent solution. Bound phage was subsequently eluted by incubating with a growth factor solution for 60 minutes. The recovered phages were amplified for 4 h in *E Coli* at 37° C. and the panning was repeated two more times. In subsequent panning rounds, the stringency was increased by raising the detergent concentration and reducing the exposure time to the library. The final phage population was plated and the DNA of 10 clones of colonies containing only one phage type were sequenced. Next, ELISA screening was used to test for false positives and determine relative binding strengths of the selected clones. Utilizing this protocol, the best binding epitope for rh-BMP-2 was found to be YPVHPST (SEQ ID NO:7) and for rh-TGF-β1 LPLGNSH (SEQ ID NO:8). (See Table 1, below.)

Example 8a

Phage display was performed with the Ph.D. 7 kit (New England Biosystems). Fifty microliters of diluted M13-phage library (containing $2\times10^9$ phages and all possible 7-mer sequences) were added to 96-well microtiter plates, which had been exposed to 50 μl 10 μg/ml growth factor (peprotech) solution for 18 h at 0° C. The plates were blocked for 1 h then incubated at room temperature for 60 minutes with gentle agitation. Unbound phage was removed by rinsing with TBS/Tween-20 (0.1% v/v Tween-20). Bound phage was subsequently eluted by incubating with 50 μl growth factor solution for 60 minutes. The presence of binding phage was determined by serial dilution of the phages and subsequent plating with E. Coli on agar plates. The number of plaques formed can be related to the number of phages in the original mixture. The phages were subsequently amplified for 4 h in E. Coli at 37° C. In subsequent panning rounds, the concentration of Tween-20 was raised to 0.5% and the binding and elution times were decreased and increased, respectively, to increase the stringency of the selection process. After three rounds of panning, the recovered phage mixture is diluted and plated with bacteria on agar. Subsequently, plaques are isolated containing a single DNA sequence. After purification, ten clones were sequenced. Next, ELISA screening was used to eliminate false positives and determine relative binding strengths of the selected clones. Each clone was incubated for 1 h on growth factor coated microtiter plates, the plates were rinsed with TBS/Tween-20 and subsequently HRP-conjugated anti-M13 antibody (Amersham Biosciences) was incubated for 1 h. After addition of ABTS, the absorbance at 450 nm was measured after 30 minutes to determine the relative binding strengths of the isolated clones. The strongest binder was subsequently selected.

TABLE 1

Binding sequences for BMP-2 and TGF-β1 derived using phage display

| BMP-2 | | TGF-β1 | |
|---|---|---|---|
| YPVHPST (1) (SEQ ID NO: 7) | LHYPFMT (3) (SEQ ID NO: 13) | LPLGNSH (1) (SEQ ID NO: 8) | RTTSPTA (3) (SEQ ID NO: 22) |
| KVPPANT (3) (SEQ ID NO:9) | QQTQAQH (4) (SEQ ID NO: 14) | LRNYSHS (3) (SEQ ID NO: 18) | GKYPPTS (3) (SEQ ID NO:23) |
| KQALTQT (3) (SEQ ID NO: 10) | PIQPDER (2) (SEQ ID NO: 15) | VYRHLPT (2) (SEQ ID NO: 19) | AWKSVTA (3) (SEQ ID NO:24) |
| WPALFTH (3) (SEQ ID NO: 11) | PFDPPVR (2) (SEQ ID NO: 16) | RVSTWDT (3) (SEQ ID NO: 20) | LPSPIQK (2) (SEQ ID NO: 25) |
| PGPTVQG (2) (SEQ ID NO: 12) | DVSPAYH (3) (SEQ ID NO: 17) | PAPRWIH (3) (SEQ ID NO: 21) | |

The numeric coding illustrates the relative binding strengths of the selected clones in decreasing binding strength from highest (1) to lowest (4). All sequences bind significantly.

Example 9

Since the peptide sequences as displayed on the phage had a free N-terminus, it was not possible to use a typical synthesis route for the PAs. Therefore, an aspartic acid whose side chain was modified with dodecylamine was reacted with a Rink amide resin. (See, Scheme 2, above.) Subsequently, the remainder of the peptide could be synthesized using regular Fmoc-peptide synthesis techniques, yielding a PA with reverse polarity. The elected peptide sequences were $V_6K_3SG_3$YPVHPST (9) (SEQ ID NO:26) for BMP-2 and $V_3A_3K_3SG_3$LPLGNSH (10) (SEQ ID NO:27) for TGF-β1, respectively (Scheme 3). The $K_3$ segment was chosen to co-assemble with the charged $E_3$ head groups of the filler 2. The $SG_3$ (SEQ ID NO:28) sequence is a spacer unit and is the same spacer as was present on the phage. Binding constants of BMP-2 with, respectively, YPVHPST (SEQ ID NO: 7) and KQALTQT (SEQ ID NO:10) were $K_a$=1.9.+0.9 $10^6$ $M^{-1}$ and 2.1+0.85 $10^5$ $M^{-1}$ as determined by fluorescence depolarization, illustrating the tunability of binding strength.

Example 9a

Asp(CONHC$_{12}$)-Val-Val-Val-Val-Val-Val-Lys-Lys-Lys-Ser-Gly-Gly-Gly-Tyr-Pro-Val-His-Pro-Ser-Thr (9) (SEQ ID NO:26)

$^1$H NMR (d$_6$DMSO): δ 0.82 (br-s, 39H, Val H, +tail CH$_3$), 1.22 (br-s, 20H, C$_{10}$ aliphatic tail), 1.53 (m, 6H, Lys H$_\gamma$), 1.69 (m, 6H, Lys H$_\beta$), 1.93 (m, 16H, Lys H$_\delta$+Val H$_\beta$+Pro H$_\gamma$), 2.37 (m, 4H, Pro H$_\beta$), 2.74 (br-s, 6H, Lys H$_\epsilon$), 2.98 (m, 2H, tail CH$_2$NH), 3.45 (m, 8H, Pro H$_\delta$+His H$_\beta$+Tyr H$_\beta$), 3.72 (m, 3H, Thr H$_\alpha$+Thr H$_\beta$), 4.1-4.6 (m, 13H, H$_\alpha$+Ser H$_\beta$), 6.81 (m, 5H, Tyr Aromatic Hs+His H), 7.02-8.25 (Amide NH+His H). ESI MS (H$_2$O): 773.9 (M+3H)$^{+3}$.

Example 9b

Asp(CONHC$_{12}$)-Val-Val-Val-Ala-Ala-Ala-Lys-Lys-Lys-Ser-Gly-Gly-G-ly-Leu-Pro-Leu-Gly-Gln-Ser-His-NH$_2$ (10) (SEQ ID NO:27)

$^1$H NMR (d$_6$DMSO): δ 0.82 (br-s, 21H, Val H$_\gamma$+aliphatic tail CH$_3$), 1.22 (br-s, 20H, tail C$_{10}$), 1.32 (m, 9H, Ala H$_\beta$), 1.53 (m, 6H, Lys H$_\gamma$), 1.64 (m, 6H, Lys H$_\beta$), 1.84 (m, 4H, Leu H$_\beta$), 1.93 (m, 16H, Lys H$_\delta$+Val H$_\beta$+Pro H$_\gamma$), 2.37 (m, 2H, Pro H$_\beta$), 2.74 (br-s, 6H, Lys H$_\epsilon$), 2.97 (m, 2H, tail CH$_2$ CH$_2$CONH), 3.45 (m, 4H, Pro H$_\delta$+His H$_\beta$), 3.72 (m, 3H, His $\overline{H_\alpha}$+Ser H$_\beta$), 4.10-4.61 (m, 9H, H$_\alpha$), 6.81 (m, 2H, His H), 7.02-8.25 (Amide NH+His H). ESI MS (MeOH:H$_2$O 1:1 v:v): m/z=1086.7 (M+H)$^{+2}$.

Scheme 3:

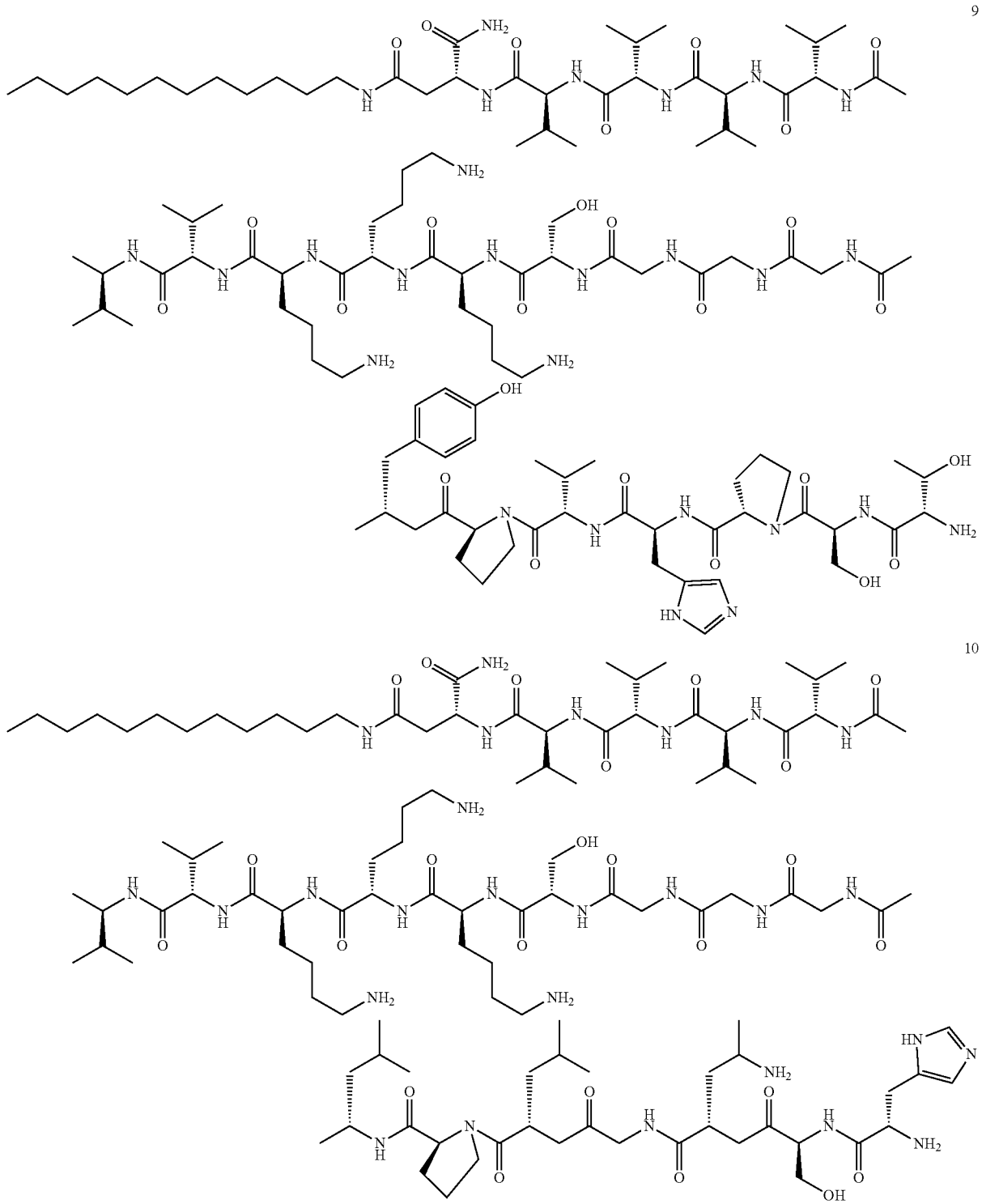

Example 10

Co-assembly of PA 9 with the filler PA 2 could be demonstrated utilizing circular dichroism (CD) spectroscopy. At a concentration of 0.13 mM, the CD spectrum of the individual PA nanofibers at this concentration have predominantly random-coil character. When mixed together, however, the CD-spectrum reflects a pure β-sheet, illustrating that the PAs co-assemble within one fiber rather than form individual homo-fibers consisting of only one PA molecule. Co-assembly is energetically favored since the electrostatic repulsions are reduced when the KKK and EEE part form a complex.

Additional evidence for co-assembly was obtained using Nuclear Overhauser Effect spectroscopy on 1.5 wt % solutions. Close contacts (<3 Å) were observed between the $E_\beta$ and $K_\epsilon$ protons and between the $E_\beta$ and $V_\delta$ protons and this distance would be significantly larger between homo-fibers. Other possible intermolecular contacts could not be attributed unambiguously. Finally, Fourier Transform infrared spectroscopy on lyophilized samples and 1 wt % solutions showed the presence of the 1630 cm$^{-1}$ peak typical of β-sheets. Similar results were obtained for 10/2 mixtures. Annealing of the samples for 24 h at 37° C. led to a significant increase in the strength of the CD effect. This increase is attributed to an increase in the size of the domain of perfectly coupled chromophores. Presumably, the initial mixing leads to the kinetic entrapment of a non-perfect mixed system and the annealing allows for the subsequent reorganization of amphiphiles to the thermodynamically most stable state. Even prolonged heating at 80° C., well above the expected melting temperatures for the hydrogen bonding network and the aliphatic tails, did not lead to any noticeable loss of supramolecular chirality, illustrating the high stability of the nanofibers.

Example 11

In order to test the physiological significance of this approach, mesenchymal stem cells were cultured in gels containing different levels of growth factors. For these cell experiments, the binding epitopes were diluted to a 50:1 (filler:binder) ratio to ensure recognition by the protein. Gels were prepared by mixing 50 μl of pre-mixed PA (2% by weight) containing the desired amount of growth factor and 50 μl mesenchymal stem cell suspension (100,000 cells) on glass cover slips, followed by the addition of 10 μl 30 mg/ml CaCl$_2$ solution. The gels were allowed to solidify for 1.5 hours after which 1 ml of mesenchymal stem cell media was added. In this way, gels were prepared consisting either of 9/2 or 2 alone and containing 0, 1 or 50 ng/ml of BMP-2. As a further control, 10,000 stem cells were plated on glass cover slips with BMP-2 added to the media in identical concentrations. The media was refreshed every fourth day and triplicate samples were isolated after 7 and 21 days of culture. Subsequently, the protein expression of lineage-specific markers osteocalcin (osteoblast), adiponectin (adipocytes), collagen II and aggrecan (chondrocytes) and α-smooth muscle actin and desmin (smooth muscle cells) was assessed by western blot.

Example 11a

Protocol for cell experiments: Human mesenchymal stem cells (Cambrex technologies) were plated at a density of 5,000 cells/cm$^2$ in four T75 culture flasks in 15 ml of mesenchymal stem cell media (Cambrex Technologies) and incubated at 37° C., 5% CO$_2$, 90% humidity. At 90% confluency, the cells were trypsinized with 2.5 ml 0.25% trypsin/EDTA for 5 minutes. Subsequently, 8 ml of media was added to quench the protease activity. The cell suspensions were combined and centrifuged at 850 rpm for 8 minutes. The cell pellet was re-suspended in 1 ml of media and 10 μl was used for cell counting. The cell suspension was diluted with media to a concentration of 2,000,000 cells/ml.

PAs 1 and 3 were dissolved at a concentration of 2 wt %. Subsequently, 50 μl of 1 was mixed with 1250 μl of 3. The mixture was split in 3 portions of 410 μl and in addition 3 portions of 410 μl 3 (2 wt %) was prepared. Then, 20 μl of 2 μg/ml BMP-2 (Peprotech) was added to one portion of 1/3 and 1 to a concentration of 100 ng/ml BMP-2. Similarly, 41 μl of 20 ng/ml BMP-2 was added to a final concentration of 2 ng/ml BMP-2.

Gels were prepared in triplo by mixing 50 μl PA solution with 50 μl cell suspension on a microscope glass cover slip. Then, 10 μl 30 mg/ml CaCl$_2$ was added and the gels were allowed to solidify at 37° C., 5% CO$_2$, 90% humidity for 90 minutes. The resulting concentrations are 1 wt % PA and 0, 1 or 50 ng/ml in BMP-2. Next, 1 ml media was added. Controls with growth factor in solution were prepared by placing 5 μl cell suspension on a glass cover slip followed by the addition of 1 ml of media. Then, 25 μl 2 μg/ml BMP-2 and 0.5 μl 2 μg/ml BMP-2 were added to obtain BMP-2 concentrations of 50 ng/ml and 1 ng/ml in solution, respectively. Half the media was refreshed every fourth day Example 12

Cell viability assays showed that the viability of the cells was >95% in all the gels after 3 weeks of culture. Expression of endoglin could not be detected by western blot at either time point, indicating that all cells had started to differentiate. No expression of adiponectin and aggrecan could be detected at any point either. The expression of osteocalcin showed a marked difference between the gels and the controls. Whereas no osteocalcin could be detected in the controls, all gels expressed significant levels of osteocalcin at 7 days already rather than the usual 2-3 weeks (FIG. 3a), but did not increase significantly at the 3 week time point (FIG. 3b). The comparable expression levels at 1 and 3 weeks then imply that the expression levels of osteocalcin are constant during the culture period. Surprisingly, the expression seems to be independent on the concentrations of BMP-2 and the ratio is 1:2 between binding and no binding PA-containing gels. Moreover, the gels to which no BMP-2 was added show similar levels. Apparently, the endogenous BMP-2 levels produced by the cells themselves are enough to stimulate osteoblastic differentiation, but the capability of the binding gels to bind some of the BMP-2 lowers the amount of expressed osteocalcin slightly. The expression of osteocalcin could also be visualized with immunocytochemistry.

In contrast, α-smooth muscle actin was not detected in gels containing 9, whereas it was expressed in the gels without the binder. However, it was expressed in either case after 3 weeks (FIG. 3b), but the expression in 9/2 gels was still slightly less than in the 2 gels and significantly lower than the controls. Furthermore, no desmin expression could be detected, which is the marker of terminally differentiated smooth muscle cells.

Example 12a

Western Blot protocol: After removal of the media, the gels were rinsed with 1 ml phosphate buffer saline and subsequently, the cells were lysed in 200 μl 2% sodium dodecyl sulfate, 0.08 M Tris, 10% glycerol. The three lysates were combined and protein concentrations were measured by mixing 10 μl lysate with 200 μl BCA protein assay reagent (Pierce) and reading the absorbance at 562 nm against a BSA standard series after 30 min. incubation at 37° C. Subsequently, 10 μg of protein, 3 μl β-mercapto-ethanol, 3 μl bromophenolblue were mixed and water was added to a total volume of 36 μl. The mixture was boiled for 5 minutes and loaded onto either a 4% (endoglin, aggrecan) or a 10-20% (osteocalcin, a-smooth muscle actin, adiponectin, desmin) Novex tris(glycine) gel (Invitrogen). The gels were run for 90 minutes in tris(glycine) running buffer (Invitrogen) at a constant voltage of 130 V. Then, the proteins were transferred to a nitrocellulose membrane (Bio-Rad) at a constant current of 190 mA for 90-120 minutes.

The membranes were blocked for 1 h in 5% non-fat milk (Bio-Rad) and probed for the respective markers at a 1:500 dilution in 1% milk for 2 h using the monoclonal antibodies for osteocalcin (clone 190125, R&D systems) endoglin (clone 166709, R&D systems), adiponectin (clone 166126, R&D systems), α-smooth muscle actin (clone 1A4, R&D systems) and polyclonal aggrecan (AF1220, R&D systems). The membranes were rinsed 3× for 15 minutes with tris buffer saline/0.1% tween-20 (TTBS). Then, secondary antibodies were equilibrated for 1 h at a 1:3,000 dilution in 1% milk followed by 3 rinsing steps with TTBS. The membranes were developed by 1 minute equilibration with ECL western blot analysis solution (Amersham Biosciences) and exposed to ECL hyperfilm (Amersham Biosciences).

Example 12b

Cells were fixed for 20 mins with 2% paraformaldehyde/ 0.2% glutaraldehyde/0.2M sodium calcodylate at 4° C. After rinsing with PBS (2×), the samples were incubated for 5 mins with 0.1% Triton-X in PBS. Subsequently, the samples were rinsed with PBS (2×). Next, human osteocalcin monoclonal antibody (R&D systems, 1:200) in 1% BSA/PBS was added and the samples were incubated overnight at 4° C. After triple rinsing with PBS, FITC-conjugated secondary antibody in 1% BSA/PBS was added and incubated for 2 h. The samples were visualized after triple PBS rinsing on a Nikon Eclipse TE2000 microscope at 10× magnification.

Example 13

A series of experiments were performed as for PA 10, binding TGF-β1, BMP-2 experiments, except that the highest TGF-β1 concentration is 20 ng/ml rather than 50 ng/ml. Samples were isolated after 10 days. Culturing in the presence of TGF-β1 leads to differentiation into the smooth muscle and cartilage lineages. Collagen II expression is higher for the binding gels and seems to increase with increasing TGF-β1. Surprisingly, osteocalcin and collagen X are expressed, which indicates that maturation to the stage of hypertrophic chondrocytes occurs, which is unexpected at this early time point. Similarly, α-smooth muscle actin expression increases with TGF-β1 concentration but is higher in the binding gels than in the nonbinding gels. It's even higher in the controls, but the expression levels of desmin show that these are mainly immature muscle cells.

Example 14

Numerous binding sequences were determined for vascular endothelial growth factor (VEGF), both with 7- and 12-mer phage display kit, basic fibroblast growth factor (FGF-2), neurotrophin-3 (NT-3) and laminin-5; * denotes the strongest binders:

| VEGF 7-mer | 12-mer |
|---|---|
| WPTWVNN (SEQ ID NO: 31) | PTPLKVRLHSYN* (SEQ ID NO: 63) |
| YYTVHHM (SEQ ID NO: 32) | VSILSTIPNSMT* (SEQ ID NO: 64) |
| WHWSLNH (SEQ ID NO: 33) | PLTPSALLPIFE* (SEQ ID NO: 65) |
| SWWAPFH (SEQ ID NO: 34) | LPQKNTIQYEKM (SEQ ID NO: 66) |
| FTEPLAS (SEQ ID NO: 35) | |
| THAFRVM (SEQ ID NO: 36) | |
| ASLFSSN (SEQ ID NO: 37) | |
| LLTVSSY (SEQ ID NO: 38) | |
| LPYPHYH (SEQ ID NO: 39) | |

| FGF-2 | |
|---|---|
| PMHHHKH | (SEQ ID NO: 40) |
| AQVRSGD | (SEQ ID NO: 41) |
| KHPPTNW | (SEQ ID NO: 42) |
| AMLSHLS | (SEQ ID NO: 43) |
| DFIQPYQ | (SEQ ID NO: 44) |
| VYWSRIE | (SEQ ID NO: 45) |
| AMPQRPL | (SEQ ID NO: 46) |
| HSRHFHH | (SEQ ID NO: 47) |
| RMTQVPL | (SEQ ID NO: 48) |
| LSTPPLR | (SEQ ID NO: 49) |
| NT-3 | |
| HTTEILH | (SEQ ID NO: 50) |
| PSNYQTS | (SEQ ID NO: 51) |
| SYFPSSA | (SEQ ID NO: 52) |
| EARQSYS | (SEQ ID NO: 53) |
| DEPQKAH | (SEQ ID NO: 54) |
| TLGLGLH | (SEQ ID NO: 55) |
| YMRRSLS | (SEQ ID NO: 56) |
| VVLYLPL | (SEQ ID NO: 57) |
| Laminin-5 | |
| SKLNTKS | (SEQ ID NO: 58) |
| PTYHHRH | (SEQ ID NO: 59) |
| LRHKSLH | (SEQ ID NO: 60) |
| RYHPHLH* | (SEQ ID NO: 61) |
| GRYHHYLH | (SEQ ID NO: 62) |

As illustrated by the preceding examples, this invention provides a synthetic strategy for peptide amphiphile molecules with free N-termini compatible with standard solid phase methodology. When mixed with free C-terminus PAs, these molecules self-assemble into nanofibers containing highly thermally stable β-sheet structures which appear to be more stable than co-assemblies of PAs with identical polarity. The new opportunity to create assemblies with free N-termini on their surfaces enables the design of bioactive nanofibers not accessible previously with nanostructures that expose the C-terminus of the peptide sequence.

Although the present invention has been described in considerable detail with reference to certain preferred embodiments thereof, other versions are possible. For example peptide or protein sequences derived from a phage display process may be used to form binding peptide amphiphiles that bind and retain proteins other than growth factors. Enzymes could be coupled to form binding peptide amphiphiles which can be self assembled and immobilized on the surfaces of nanofiber hydrogels. Such hydrogels may be used as a coating for sensor applications. Alternatively, the binding interaction of the phage display derived peptide coupled to the peptide amphiphile could be selected to strongly bind peptides such as HGF (hepatocyte growth factor) or VEGF and treat various diseases and conditions by removing them. Hydrogels formed from self assembly of these binding peptide amphiphiles could be molded for insertion into a site on a patient or for use in a filtration system. The hydrogels could be used to remove target peptides like HGF or VEGF from a site such as a joint or tumor on a patient or from a fluid in a patient.

We claim:

1. A binding peptide consisting of an amino acid sequence selected from the group consisting of: YPVHPST (SEQ ID NO:7), KVPPANT (SEQ ID NO:9), KQALTQT (SEQ ID NO:10), WPALFTH (SEQ ID NO:11), PGPTVQG (SEQ ID NO:12), LHYPFMT (SEQ ID NO:13), QQTQAQH (SEQ ID NO:14), PIQPDER (SEQ ID NO:15), PFDPPVR (SEQ ID NO:16), DVSPAYH (SEQ ID NO:17), LPLGNSH (SEQ ID NO:8), LRNYSHS (SEQ ID NO:18), VYRHLPT (SEQ ID NO:19), RVSTWDT (SEQ ID NO:20), PAPRWIH (SEQ ID NO:21), RTTSPTA (SEQ ID NO:22), GKYPPTS (SEQ ID NO:23), AWKSVTA (SEQ ID NO:24), and LPSPIQK (SEQ ID NO:25).

2. The binding peptide of claim 1, wherein said peptide binds the growth factor BMP-2.

3. The binding peptide of claim 2, wherein said peptide is YPVHPST (SEQ ID NO:7).

4. The binding peptide of claim 1, wherein said peptide binds the growth factor TGF-β1.

5. The binding peptide of claim 4, wherein said peptide is LPLGNSH (SEQ ID NO:8).

6. A compound having the formula $C_{15}H_{31}CO$-VVVAAAKKK (SEQ ID NO: 3).

7. A compound selected from $V_3A_3K_3SG_3$LPLGNSH (SEQ ID NO:27) and $V_6K_3SG_3$YPVHPST (SEQ ID NO:26).

8. A method of controlling the differentiation of stem cells into chondrocytes comprising contacting said stem cells with a composition comprising a micellar assembly comprising a peptide amphiphile having a hydrophobic component of an alkyl chain from six to twenty-two carbon atoms in length, a peptide component selected from YPVHPST (SEQ ID NO:7) and LPLGNSH (SEQ ID NO:8), and therebetween, a β-sheet forming unit selected from $V_3A_3K_3$ (SEQ ID NO:3), $V_3A_3E_3$ (SEQ ID NO:4), and $V_6K_3$.

9. The method of claim 8, wherein said peptide component is YPVHPST (SEQ ID NO:7).

10. The method of claim 8, wherein said peptide component is LPLGNSH (SEQ ID NO:8).

11. The method of claim 8, wherein said β-sheet forming unit is $V_3A_3K_3$ (SEQ ID NO:3) or $V_6K_3$.

12. The method of claim 8, wherein said peptide amphiphile comprises the formula $V_3A_3K_3SG_3$LPLGNSH (SEQ ID NO:27) or $V_6K_3SG_3$YPVHPST (SEQ ID NO:28).

13. The method of claim 8, wherein said composition further comprises the growth factor TGF-β1.

14. The method of claim 8, wherein said composition further comprises the growth factor BMP-2.

* * * * *

```
                         SEQUENCE LISTING

<160> NUMBER OF SEQ ID NOS: 69

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Leu Ser Leu
  1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Ala Ala Ala
  1

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Val Val Ala Ala Ala Lys Lys Lys
  1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Val Val Ala Ala Ala Glu Glu Glu
  1               5

<210> SEQ ID NO 5
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Val Val Val Val Val Lys Lys Lys
 1               5                  10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Val Val Val Ala Ala Ala Glu Glu Glu
 1               5                  10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Tyr Pro Val His Pro Ser Thr
 1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Pro Leu Gly Asn Ser His
 1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Val Pro Pro Ala Asn Thr
 1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Gln Ala Leu Thr Gln Thr
```

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Trp Pro Ala Leu Phe Thr His
 1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Pro Gly Pro Thr Val Gln Gly
 1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu His Tyr Pro Phe Met Thr
 1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Gln Thr Gln Ala Gln His
 1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Pro Ile Gln Pro Asp Glu Arg
 1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Pro Phe Asp Pro Pro Val Arg
 1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Val Ser Pro Ala Tyr His
 1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Arg Asn Tyr Ser His Ser
 1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Val Tyr Arg His Leu Pro Thr
 1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Val Ser Thr Trp Asp Thr
 1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Pro Ala Pro Arg Trp Ile His
 1               5

<210> SEQ ID NO 22
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 22

Arg Thr Thr Ser Pro Thr Ala
 1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Lys Tyr Pro Pro Thr Ser
 1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Trp Lys Ser Val Thr Ala
 1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Leu Pro Ser Pro Ile Gln Lys
 1               5

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Val Val Val Val Val Val Lys Lys Lys Ser Gly Gly Gly Tyr Pro Val
 1               5                  10                  15

His Pro Ser Thr
            20

<210> SEQ ID NO 27
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27
```

Val Val Val Ala Ala Ala Lys Lys Lys Ser Gly Gly Gly Leu Pro Leu
1               5                   10                  15

Gly Asn Ser His
            20

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ser Gly Gly Gly
1

<210> SEQ ID NO 29
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Val Val Val Val Val Lys Lys Lys Ser Gly Gly Gly Tyr Pro
1               5                   10                  15

Val His Pro Ser Thr
            20

<210> SEQ ID NO 30
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asp Val Val Val Ala Ala Ala Lys Lys Lys Ser Gly Gly Gly Leu Pro
1               5                   10                  15

Leu Gly Gln Ser His
            20

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Trp Pro Thr Trp Val Asn Asn
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Tyr Tyr Thr Val His His Met

```
                              1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Trp His Trp Ser Leu Asn His
  1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ser Trp Trp Ala Pro Phe His
  1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Phe Thr Glu Pro Leu Ala Ser
  1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Thr His Ala Phe Arg Val Met
  1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ala Ser Leu Phe Ser Ser Asn
  1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 38

Leu Leu Thr Val Ser Ser Tyr
 1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Leu Pro Tyr Pro His Tyr His
 1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Pro Met His His His Lys His
 1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ala Gln Val Arg Ser Gly Asp
 1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Lys His Pro Pro Thr Asn Trp
 1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ala Met Leu Ser His Leu Ser
 1               5

<210> SEQ ID NO 44
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 44

Asp Phe Ile Gln Pro Tyr Gln
 1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Val Tyr Trp Ser Arg Ile Glu
 1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Met Pro Gln Arg Pro Leu
 1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

His Ser Arg His Phe His His
 1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Met Thr Gln Val Pro Leu
 1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Leu Ser Thr Pro Pro Leu Arg
 1               5
```

```
<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

His Thr Thr Glu Ile Leu His
 1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Pro Ser Asn Tyr Gln Thr Ser
 1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ser Tyr Phe Pro Ser Ser Ala
 1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Glu Ala Arg Gln Ser Tyr Ser
 1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Glu Pro Gln Lys Ala His
 1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55
```

Thr Leu Gly Leu Gly Leu His
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Tyr Met Arg Arg Ser Leu Ser
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Val Val Leu Tyr Leu Pro Leu
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ser Lys Leu Asn Thr Lys Ser
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Pro Thr Tyr His His Arg His
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Leu Arg His Lys Ser Leu His
1               5

<210> SEQ ID NO 61
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 61

Arg Tyr His Pro His Leu His
 1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Arg Tyr His His Tyr Leu His
 1               5

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Pro Thr Pro Leu Lys Val Arg Leu His Ser Tyr Asn
 1               5                  10

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Val Ser Ile Leu Ser Thr Ile Pro Asn Ser Met Thr
 1               5                  10

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Pro Leu Thr Pro Ser Ala Leu Leu Pro Ile Phe Glu
 1               5                  10

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Leu Pro Gln Lys Asn Thr Ile Gln Tyr Glu Lys Met
 1               5                  10

<210> SEQ ID NO 67
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Val Val Val Val Val Val Lys Lys Lys Ser Gly Gly Gly Tyr Pro Val
 1               5                  10                  15

His Pro Ser Thr
            20

<210> SEQ ID NO 68
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Val Val Val Ala Ala Ala Lys Lys Lys Ser Gly Gly Gly Leu Pro Leu
 1               5                  10                  15

Gly Asn Ser His
            20

<210> SEQ ID NO 69
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Val Val Val Ala Ala Ala Lys Lys Lys Ser Gly Gly Gly
 1               5                  10
```